(12) United States Patent
Jacobs et al.

(10) Patent No.: US 7,148,242 B2
(45) Date of Patent: Dec. 12, 2006

(54) N-FORMYL HYDROXYLAMINE COMPOUNDS, COMPOSITIONS AND METHODS OF USE

(75) Inventors: Jeffrey Jacobs, San Mateo, CA (US); Rakesh K. Jain, Fremont, CA (US); Dinesh V. Patel, Fremont, CA (US); Zhengyu Yuan, Fremont, CA (US)

(73) Assignee: Novartis AG, Basel (CH)

( * ) Notice: Subject to any disclaimer, the term of this patent is extended or adjusted under 35 U.S.C. 154(b) by 406 days.

(21) Appl. No.: 10/171,706

(22) Filed: Jun. 14, 2002

(65) Prior Publication Data

US 2003/0045479 A1   Mar. 6, 2003

Related U.S. Application Data

(60) Provisional application No. 60/360,313, filed on Feb. 27, 2002, provisional application No. 60/298,419, filed on Jun. 15, 2001.

(51) Int. Cl.
*A61K 31/44* (2006.01)
*A61K 31/426* (2006.01)
*A61K 31/40* (2006.01)
*A61K 31/36* (2006.01)
*C07D 417/12* (2006.01)
*C07D 401/12* (2006.01)
*C07D 407/12* (2006.01)

(52) U.S. Cl. .................. 514/340; 514/342; 514/365; 514/422; 514/464; 546/269.7; 546/278.4; 546/279.1; 548/200; 548/518; 548/526; 549/439

(58) Field of Classification Search ............ 546/279.1, 546/347, 269.7, 278.4, 279.4; 514/343, 358, 514/340, 342, 365, 422, 464; 548/200, 518, 548/526; 549/439
See application file for complete search history.

(56) References Cited

U.S. PATENT DOCUMENTS

| | | | |
|---|---|---|---|
| 4,052,511 A | 10/1977 | Cushman et al. | 424/274 |
| 4,303,662 A | 12/1981 | Sprague | 424/256 |
| 4,311,705 A | 1/1982 | Ondetti et al. | 424/274 |
| 4,321,383 A | 3/1982 | Sprague | 546/113 |
| 4,599,361 A | 7/1986 | Dickens et al. | 514/575 |
| 4,804,676 A | 2/1989 | Inaoka et al. | 514/423 |
| 5,128,346 A | 7/1992 | Nadzan et al. | 514/307 |
| 5,256,657 A | 10/1993 | Singh et al. | 514/228.2 |
| 5,268,384 A | 12/1993 | Galardy | 514/419 |
| 5,447,929 A | 9/1995 | Broadhurst et al. | 514/228.2 |
| 5,453,423 A | 9/1995 | Long et al. | 514/211 |
| 5,552,419 A | 9/1996 | MacPherson et al. | 514/357 |
| 5,614,625 A | 3/1997 | Broadhurst et al. | 540/480 |
| 5,643,908 A | 7/1997 | Sugimura et al. | 514/247 |
| 5,712,300 A | 1/1998 | Jacobsen | 514/389 |
| 5,869,518 A | 2/1999 | Bedoya Zurita et al. | 514/412 |

FOREIGN PATENT DOCUMENTS

| | | |
|---|---|---|
| EP | 236 872 | 9/1987 |
| EP | 274 453 | 7/1988 |
| EP | 334 244 | 9/1989 |
| EP | 423 943 | 4/1991 |
| EP | 489 577 | 6/1992 |
| EP | 489 579 | 6/1992 |
| EP | 497 192 | 8/1992 |
| EP | 574 758 | 12/1993 |
| WO | WO 90/05716 | 5/1990 |
| WO | WO 90/05719 | 5/1990 |
| WO | WO 91/02716 | 3/1991 |
| WO | WO 92/13831 | 8/1992 |
| WO | WO 92/22523 | 12/1992 |
| WO | WO 93/09090 | 5/1993 |
| WO | WO 93/09097 | 5/1993 |
| WO | WO 93/20047 | 10/1993 |
| WO | WO 93/24449 | 12/1993 |
| WO | WO 93/24475 | 12/1993 |
| WO | WO 94/02446 | 2/1994 |
| WO | WO 94/02447 | 2/1994 |
| WO | WO 94/21612 | 9/1994 |
| WO | WO 94/25434 | 11/1994 |
| WO | WO 94/25435 | 11/1994 |
| WO | WO 95/33731 | 12/1995 |
| WO | WO 96/25156 | 8/1996 |
| WO | WO 96/26918 | 9/1996 |
| WO | WO 97/30707 | 8/1997 |
| WO | WO 97/49674 | 12/1997 |
| WO | WO 98/55449 | 12/1998 |
| WO | WO 99/02510 | 1/1999 |
| WO | WO 99/39704 | 8/1999 |
| WO | WO 9939704 A1 * | 8/1999 |

OTHER PUBLICATIONS

Bord et al., "Stromelysin-1 (MMP-3) and Stromelysin-2 (MMP-10) Expression in Developing Human Bone: Potential Roles in Skeletal Development", Bone, vol. 23, No. 1, pp. 7-12 (1998).

Chang et al., "Methionine Aminopeptidase Gene of *Escherichia coli* Is Essential for Cell Growth", J. Bacteriol., vol. 171, No. 7, pp. 4071-4072 (1989).

(Continued)

*Primary Examiner*—Kamal A. Saeed
*Assistant Examiner*—Joseph R. Kosack
(74) *Attorney, Agent, or Firm*—Regina BAutista

(57) ABSTRACT

N-[1-oxo-2-alkyl-3-(N-hydroxyformamido)-propyl]-(carbonylamino-aryl or -heteroaryl)-azacyclo$_{4-7}$alkanes or thiazacyclo$_{4-7}$alkanes or imidazacyclo$_{4-7}$alkanes have interesting properties, e.g., in the treatment or prevention of disorders amenable to treatment by peptidyl deformylase inhibitors such as treatment of bacterial infections.

40 Claims, No Drawings

OTHER PUBLICATIONS

Durand et al., "Peptide Aldehyde Inhibitors of Bacterial Peptide Deformylases", *Arch. Biochem. Biophys.*, vol. 367, No. 2, pp. 297-302 (1999).

Gearing et al., "Processing of Tumour Necrosis Factor-α Precursor by Metalloproteinasis", *Nature*, vol. 370, pp. 555-557 (1994).

Hao et al., "Structural Basis for the Design of Antibiotics Targeting Peptide Deformylase", *Biochemistry*, vol. 38, No. 15, pp. 4712-4719 (1999).

Hu et al., "H-Phosphonate Derivatives as Novel Peptide Deformylase Inhibitors", *Bioorg. Med. Chem. Letts.*, vol. 8, pp. 2479-2482 (1998).

Izquierdo-Martin et al., "Mechanistic Studies on the Inhibition of Thermolysin by a Peptide Hydroxamic Acid", *J. Am. Chem. Soc.*, vol. 114, No. 1, pp. 325-331 (1992).

Liu et al., "Distinct Expression of Gelatinase A [Matrix Metalloproteinase (MMP)-2], Collagenase-3 (MMP-13), Membrane Type MMP 1 (MMP-14), and Tissue Inhibitor of MMPs Type 1 Mediated by Physiological Signals During Formation and Regression of the Rat Corpus Luteum", *Endocrinology*, vol. 140, No. 11, pp. 5330-5338 (1999).

Mazel et al., Genetic Characterization of Polypeptide Deformylase, a Distinctive Enzyme of Eubacterial Translation, *EMBO J.*, vol. 13, No. 4, pp. 914-923 (1994).

McGeehan et al., "Regulation of Tumour Necrosis Factor-a Processing by a Metalloproteinase Inhibitor", *Nature*, vol. 370, pp. 558-561 (1994).

Meinnel et al., "Characterization of the *Thermus thermophilus* Locus Encoding Peptide Deformylase and Methionyl-tRNA$_f^{Met}$ Formyltransferase", *J. Bacteriol.*, vol. 176, No. 23, pp. 7387-7390 (1994).

Meinnel et al., "Structure-Function Relationships within the Peptide Deformylase Family. Evidence for a Conserved Architecture of the Active Site Involving Three Conserved Motifs and a Metal Ion", *J. Mol. Biol.*, vol. 267, pp. 749-761 (1997).

Meinnel et al., "Design and Synthesis of Substrate Analogue Inhibitors of Peptide Deformylase", *Biochemistry*, vol. 38, No. 14, pp. 4287-4295 (1999).

Mohler et al., "Protection Against a Lethal Dose of Endotoxin by an Inhibitor of Tumour Necrosis Factor Processing", *Nature*, vol. 370, pp. 218-220 (1994).

O'Connell et al., "A High Quality Nuclear Magnetic Resonance Solution Structure of Peptide Deformylase from *Escherichia coli*: Application of an Automated Assignment Strategy Using GARANT", *J. Biomol. NMR*, vol. 13, No. 4, pp. 311-324 (1999).

Rajagopalan et al., "Purification, Characterization, and Inhibition of Peptide Deformylase from *Escherichia coli*", *Biochemistry*, vol. 36, No. 45, pp. 13910-13918 (1997).

Yamagiwa et al., "Expression of Metalloproteinase-13 (Collagenase-3) Is Induced During Fracture Healing in Mice", *Bone*, vol. 25, No. 2, pp. 197-203 (1999).

\* cited by examiner

N-FORMYL HYDROXYLAMINE COMPOUNDS, COMPOSITIONS AND METHODS OF USE

FIELD OF INVENTION

This invention is directed to novel N-formyl hydroxylamine compounds, to the uses of these compounds in various medicinal applications, including treating disorders amenable to treatment by peptidyl deformylase inhibitors such as treatment of bacterial infections, and to pharmaceutical compositions comprising these compounds.

BACKGROUND OF THE INVENTION

Treatment of microbial infection in host organisms requires an effective means to kill the microbe while doing as little harm to the host as possible. Accordingly, agents which target characteristics unique to a pathology-causing microorganism are desirable for treatment. Penicillin is an extremely well-known example of such an agent. Penicillin acts by inhibiting biosynthesis of bacterial cell walls. Since mammalian cells do not require cell walls for survival, administration of penicillin to a human infected with bacteria may kill the bacteria without killing human cells.

However, the use of antibiotics and antimicrobials has also resulted in increased resistance to these agents. As bacteria become resistant to older, more widely used antimicrobial agents, new antimicrobials must be developed in order to provide effective treatments for human and non-human animals suffering from microbial infection.

Peptide deformylase is a metallopeptidase found in prokaryotic organisms such as bacteria. Protein synthesis in prokaryotic organisms begins with N-formyl methionine (fMet). After initiation of protein synthesis, the formyl group is removed by the enzyme peptide deformylase (PDF); this activity is essential for maturation of proteins. It has been shown that PDF is required for bacterial growth (see Chang et al., J. Bacteriol., Vol. 171, pp. 4071–4072 (1989); Meinnel et al., J. Bacteriol., Vol. 176, No. 23, pp. 7387–7390 (1994); and Mazel et al., EMBO J., Vol. 13, No. 4, pp. 914–23 (1994)). Since protein synthesis in eukaryotic organisms does not depend on fMet for initiation, agents that will inhibit PDF are attractive candidates for development of new antimicrobial and antibacterial drugs. Prokaryotic organisms, including disease-causing prokaryotes, are described in Balows, Truper, Dworkin, Harder and Schleifer, Eds., "The Prokaryotes", $2^{nd}$ Ed., Springer-Verlag, NY (1992); and Holt (Editor-in-Chief), "Bergey's Manual of Systematic Bacteriology", Vols. 1–4, Williams & Wilkins, Baltimore (1982, 1986, 1989).

PDF is part of the metalloproteinase superfamily. While PDF clearly shares many of the features which characterize metalloproteinases, it differs from other members of the superfamily in several important respects. First, the metal ion in the active enzyme appears to be Fe (II), or possibly another divalent cationic metal, instead of the zinc ion more commonly encountered (see Rajagopalan et al., J. Am. Chem. Soc., Vol. 119, pp. 12418–12419 (1997)). Second, the divalent ion appears to play an important role, not only in catalysis, but also in the structural integrity of the protein. Third, the third ligand of the divalent ion is a cysteine, rather than a histidine or a glutamate, as in other metalloproteinases and is not located at the C-terminal side of the HEXXH motif but far away along the amino acid sequence and N-terminal to the motif. Finally, the solution structure shows significant differences in the secondary and tertiary structure of PDF compared to other prototypical metalloproteinases (see Meinnel et al., J. Mol. Biol., Vol. 262, pp. 375–386 (1996)). PDF from E. coli, Bacillus stearothermophilus and Thermus thermophilus have been characterized (see Meinnel et al., J. Mol. Biol., Vol. 267, pp. 749–761 (1997)). The enzyme studied by Meinnel et al. contained a zinc ion as the divalent ion and the structural features summarized above were obtained from zinc-containing proteins. The structure of the protein has also been determined by NMR (see O'Connell et al., J. Biomol. NMR, Vol. 13, No. 4, pp. 311–324 (1999)).

Metalloproteinases are critical to many aspects of normal metabolism. The class known as matrix metalloproteinases (MMPs) are involved in tissue remodeling, such as degradation of the extracellular matrix. These enzymes are believed to play a role in normal or beneficial biological events such as the formation of the corpus luteum during pregnancy (see Liu et al., Endocrinology, Vol. 140, No. 11, pp. 5330–5338 (1999)), wound healing (see Yamagiwa et al., Bone, Vol. 25, No. 2, pp. 197–203 (1999)), and bone growth in healthy children (see Bord et al., Bone, Vol. 23, No. 1, pp. 7–12 (1998)). Disorders involving metalloproteinases have been implicated in several diseases such as cancer, arthritis and autoimmune diseases.

Because of the importance of MMPs in normal physiological processes, it would be preferable to develop agents that inhibit PDF, a metalloproteinase present only in prokaryotes, while avoiding significant inhibition of MMPs. Alternatively, PDF inhibitors which also inhibit MMPs may be of use where the therapeutic benefits of inhibiting PDF outweigh the risk of side effects from MMP inhibition.

A wide variety of compounds have been developed as candidate inhibitors of MMPs and other metalloproteinases, and much effort has also been directed at synthetic methods for these compounds and related compounds (see Izquierdo-Martin et al., J. Am. Chem. Soc., Vol. 114, pp. 325–331 (1992); Cushman et al., Chapter 5, "Specific Inhibitors of Zinc Metallopeptidases", Topics in Molecular Pharmacology, Burgen & Roberts, Eds. (1981); Mohler et al., Nature, Vol. 370, pp. 218–220 (1994); Gearing et al., Nature, Vol. 370, pp. 555–557 (1994); McGeehan et al., Nature, Vol. 370, pp. 558–561 (1994); U.S. Pat. Nos. 4,052,511, 4,303,662, 4,311,705, 4,321,383, 4,599,361, 4,804,676, 5,128,346, 5,256,657, 5,268,384, 5,447,929, 5,453,423, 5,552,419, 5,614,625, 5,643,908, 5,712,300, and 5,869,518; European patent publications EP 236872, EP 274453, EP 334244, EP 423943, EP 489577, EP 489579, EP 497192, EP 574758; and International PCT Patent Applications Publication Nos. WO 90/05716, WO 90/05719, WO 91/02716, WO 92/13831, WO 92/22523, WO 93/09090, WO 93/09097, WO 93/20047, WO 93/24449, WO 93/24475, WO 94/02446, WO 94/02447, WO 94/21612, WO 94/25434, WO 94/25435, WO 95/33731, WO 96/25156, WO 96/26918 WO 97/30707, WO 97/49674, WO 98/55449, and WO 99/02510).

Research on inhibitors of PDF is much less extensive than that for inhibitors of MMPs. N-formyl hydroxylamine derivatives are described in International Patent Application WO 99/39704. Peptide aldehyde inhibitors of PDFs are described in Durand et al., Arch. Biochem. Biophys., Vol. 367, No. 2, pp. 297–302 (1999). The PDF inhibitor (S)-2-O—(H-phosphonoxy)-L-caproyl-L-leucyl-p-nitroanilide is described in Hao et al., Biochemistry, Vol. 38, pp. 4712–4719 (1999), and peptidyl H-phosphonate inhibitors of PDF are discussed in Hu et al., Bioorg. Med. Chem. Lett., Vol. 8, pp. 2479–2482 (1998). Formylated peptides and pseudopeptides are described in Meinnel et al., Biochemistry, Vol. 38, No. 14, pp. 4288–4295 (1999) as inhibitors of PDF.

In view of the importance of identifying new antibiotics to treat bacteria resistant to existing antibiotics, it is desirable to develop novel inhibitors of PDF for evaluation and use as antibacterial and antimicrobial agents. The present invention fulfills this need.

SUMMARY OF THE INVENTION

In particular, the present invention provides a N-[1-oxo-2-alkyl-3-(N-hydroxyformamido)-propyl]-(carbonylaminoaryl or -heteroaryl)-azacyclo$_{4-7}$alkane or thiazacyclo$_{4-7}$alkane or imidazacyclo$_{4-7}$alkane (referred to herein collectively as "compounds of the invention"), a salt thereof or a prodrug thereof, e.g., a compound of formula (I)

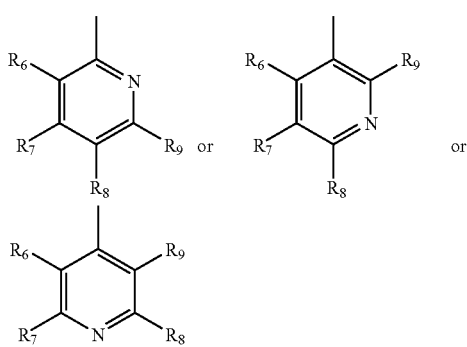

wherein X is —CH$_2$—, —S—, —CH(OH)—, —CH(OR)—, —CH(SH)—, —CH(SR)—, —CF$_2$—, —C=N(OR)— or —CH(F)—; wherein R is alkyl;

R$_1$ is aryl or heteroaryl;

each of R$_2$, R$_3$, R$_4$ and R$_5$ independently is hydrogen or alkyl, or (R$_2$ or R$_3$) and (R$_4$ or R$_5$) collectively form a C$_{4-7}$cycloalkyl; and n is 0 to 3, provided that when n is 0, X is —CH$_2$—; or a salt thereof or a prodrug thereof.

DETAILED DESCRIPTION OF THE INVENTION

In one embodiment, R$_1$ is a heteroaryl of formula (II)

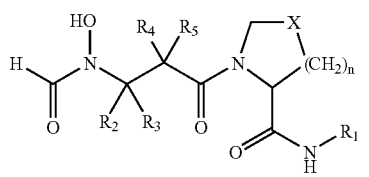

wherein each of R$_6$, R$_7$, R$_8$ and R$_9$ independently is hydrogen, alkyl, substituted alkyl, hydroxy, alkoxy, acyl, acyloxy, SCN, halogen, cyano, nitro, thioalkoxy, phenyl, heteroalkylaryl, alkylsulfonyl, or formyl;

In another embodiment, R$_1$ is preferably a heteroaryl of formula (II.1)

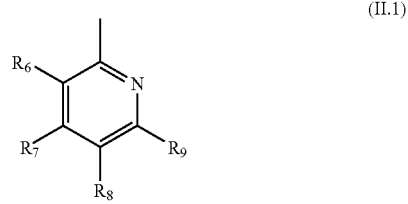

wherein R$_6$, R$_7$, R$_8$ and R$_9$ are as defined above for formula (II), e.g., wherein a) R$_6$ is nitro, alkyl, substituted alkyl, phenyl, hydroxy, formyl, heteroalkylaryl, alkoxy, acyl or acyloxy; preferably alkyl, especially C$_{1-7}$alkyl; hydroxyl; or alkoxy, especially a C$_{1-7}$alkoxy; and R$_7$, R$_8$ and R$_9$ are hydrogen; or b) R$_6$, R$_8$ and R$_9$ are hydrogen, and R$_7$ is alkyl, substituted alkyl, phenyl, halogen, alkoxy or cyano, preferably alkyl, especially C$_{1-7}$alkyl; substituted alkyl, especially substituted C$_{1-7}$alkyl such as —CF$_3$; or alkoxy, especially C$_{1-7}$alkoxy; or c) R$_6$, R$_7$ and R$_9$ are hydrogen and R$_8$ is alkyl, substituted alkyl, halogen, nitro, cyano, thioalkoxy, acyloxy, phenyl, alkylsulfonyl or carboxyalkyl, preferably alkyl, especially C$_{1-7}$alkyl; substituted alkyl, especially —CF$_3$; halogen; or carboxyalkyl; or d) R$_6$, R$_7$ and R$_8$ are hydrogen and R$_9$ is alkyl, halogen or hydroxy; or e) R$_7$ and R$_9$ are hydrogen, and each of R$_6$ and R$_8$ independently is halogen, alkyl, substituted alkyl, phenyl or cyano; or f) each of R$_7$ and R$_9$ is alkyl or substituted alkyl and R$_6$ and R$_8$ are hydrogen; or g) R$_6$ and R$_9$ are hydrogen, R$_7$ is alkyl or substituted alkyl and R$_8$ is nitro; or h) R$_8$ and R$_9$ are hydrogen, R$_6$ is cyano, and R$_7$ is alkoxy; or i) R$_7$ and R$_8$ are hydrogen and R$_6$ is alkyl, substituted alkyl, alkoxy or SCN and R$_9$ is alkyl or substituted alkyl; or j) R$_6$ and R$_7$ are hydrogen, R$_8$ is nitro or halogen and R$_9$ is alkyl or substituted alkyl; or k) R$_6$, R$_7$, R$_8$ and R$_9$ are hydrogen; or l) R$_6$ and R$_7$ together with the carbon atoms to which they are attached form a phenyl group, preferably substituted with hydroxy, and R$_8$ and R$_9$ are hydrogen; or m) R$_6$ and R$_7$ are hydrogen and R$_8$ and R$_9$ together with the carbon atoms to which they are attached form a phenyl group; or n) n is 0; or o) n is 0, and each of R$_6$, R$_7$, R$_8$ and R$_9$ independently is hydrogen, alkyl or halogen and more particularly R$_6$, R$_7$, R$_8$ and R$_9$ are hydrogen; or p) n is 0, and R$_6$, R$_8$ and R$_9$ are hydrogen and R$_7$ is alkyl; or q) n is 0, and R$_6$, R$_7$ and R$_9$ are hydrogen and R$_8$ is alkyl or halogen.

In another embodiment, $R_1$ is of formula (II.2)

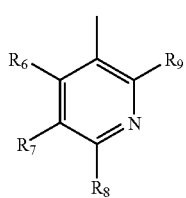

(II.2)

wherein $R_6$, $R_7$, $R_8$ and $R_9$ are as defined above for formula (II); in particular, $R_7$ and $R_8$ together with the carbon atoms to which they are attached form a phenyl group and $R_6$ and $R_9$ are hydrogen.

In yet another embodiment, the $R_1$ is of formula (III)

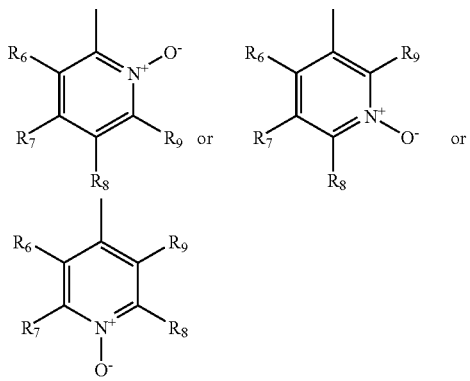

(III)

wherein each of $R_6$, $R_7$, $R_8$ and $R_9$ independently is hydrogen, alkyl, substituted alkyl, phenyl, halogen, hydroxy or alkoxy, e.g., wherein a) $R_6$ and $R_8$ are hydrogen, $R_9$ is hydrogen or alkyl and $R_7$ is alkyl, substituted alkyl or phenyl;

b) $R_6$, $R_7$ and $R_9$ are hydrogen and $R_8$ is halogen, alkyl or substituted alkyl;

c) $R_7$, $R_8$ and $R_9$ are hydrogen and $R_6$ is hydroxy.

In a particularly useful embodiment the heteroaryl is of the formula (III.1)

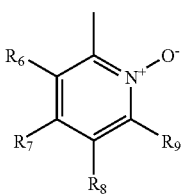

(III.1)

wherein $R_6$, $R_7$, $R_8$ and $R_9$ are as defined above for formula (III).

In another embodiment, $R_1$ is an unsubstituted phenyl or the phenyl is substituted with alkoxy, e.g., methoxy; or aryloxy, e.g., phenoxy.

In another embodiment, the $R_1$ is of formula (IV)

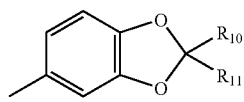

(IV)

wherein each of $R_{10}$ and $R_{11}$ independently is hydrogen or halogen. In particular, $R_{10}$ and $R_{11}$ are both either hydrogen or both halogen.

Unless otherwise stated, the following terms as used in the specification have the following meaning.

The term "cycloalkane" or "cycloalkyl" contains from 3- to 7-ring carbon atoms, and is, e.g., cyclopropyl, cyclobutyl, cyclopentyl and cyclohexyl.

The term "azacyclo$_{4-7}$alkane" contains 1-ring heteroatom which is a nitrogen. It contains from 4–7, and especially 4- or 5-ring atoms including the heteroatom.

The term "thiazacyclo$_{4-7}$alkane" contains 2-ring heteroatoms, nitrogen and sulfur. It contains from 4–7, and especially 5-ring atoms including the heteroatoms.

The term "imidazacyclo$_{4-7}$alkane" contains 2-ring heteroatoms which are both nitrogen. It contains from 4–7, and especially 5-ring atoms including the heteroatoms.

The term "alkyl" refers to saturated or unsaturated aliphatic groups, such as alkenyl or alkynyl, cycloalkyl or substituted alkyl including straight-chain, branched-chain and cyclic groups having from 1–10 carbons atoms. Preferably "alkyl" or "alk", whenever it occurs, is a saturated aliphatic group or cycloalkyl, more preferably $C_{1-7}$alkyl, particularly $C_{1-4}$alkyl. Examples of "alkyl" or "alk" include, but are not limited to, methyl, ethyl, n-propyl, isopropyl, n-butyl, isobutyl, sec-butyl, t-butyl, n-pentyl, neopentyl, n-hexyl or n-heptyl, cyclopropyl, and especially n-butyl.

The term "substituted alkyl" refers to an alkyl group that is substituted with one or more substitutents preferably 1–3 substitutents including, but not limited to substituents, such as halogen, lower alkoxy, hydroxy, mercapto, carboxy, cycloalkyl, aryl, heteroaryl and the like. Examples of substituted alkyl groups include, but are not limited to, —CF$_3$, —CF$_2$—CF$_3$, hydroxymethyl, 1- or 2-hydroxyethyl, methoxymethyl, 1- or 2-ethoxyethyl, carboxymethyl, 1- or 2-carboxyethyl and the like.

The term "aryl" or "Ar" refers to an aromatic carbocyclic group of 6–14 carbon atoms having a single ring including, but not limited to, groups, such as phenyl or multiple condensed rings, including, but not limited to, groups, such as naphthyl or anthryl, and is especially phenyl.

The term "heteroaryl" or "HetAr" refers to a 4- to 7-membered, monocyclic aromatic heterocycle or a bicycle that is composed of a 4- to 7-membered, monocyclic aromatic heterocycle and a fused-on benzene ring. The heteroaryl has at least one hetero atom, preferably one or two heteroatoms including, but not limited to, heteroatoms, such as N, O and S, within the ring. A preferred heteroaryl group is pyridinyl, pyrimidinyl or benzdioxolanyl.

The aryl or heteroaryl may be unsubstituted or substituted by one or more substitutents including, but not limited to $C_{1-7}$alkyl, particularly $C_{1-4}$alkyl such as methyl, hydroxy, alkoxy, acyl, acyloxy, SCN, halogen, cyano, nitro, thioalkoxy, phenyl, heteroalkylaryl, alkylsulfonyl and formyl.

The term "carbonylamine" as used herein refers to a —NHC(O)— group wherein the amino portion of the group is linked to the aryl/heteroaryl and the carbonyl portion of the group is linked to the azacyclo$_{4-7}$alkane, thiazacyclo$_{4-7}$alkane or imidazacyclo$_{4-7}$alkane.

The term "heteroalkyl" refers to saturated or unsaturated $C_{1-10}$alkyl as defined above, and especially $C_{1-4}$heteroalkyl which contain one or more heteroatoms, as part of the main, branched, or cyclic chains in the group. Heteroatoms may independently be selected from the group consisting of —NR— where R is hydrogen or alkyl, —S—, —O— and —P—; preferably —NR— where R is hydrogen or alkyl, and/or —O—. Heteroalkyl groups may be attached to the remainder of the molecule either at a heteroatom (if a valence is available) or at a carbon atom. Examples of heteroalkyl groups include, but are not limited to, groups, such as —O—CH$_3$, —CH$_2$—O—CH$_3$, —CH$_2$—CH$_2$—O—CH$_3$, —S—CH$_2$—CH$_2$—CH$_3$, —CH$_2$—CH(CH$_3$)—S—CH$_3$ and —CH$_2$—CH$_2$—NH—CH$_2$—CH$_2$—.

The heteroalkyl group may be unsubstituted or substituted with one or more substituents, preferably 1–3 substituents, including but not limited to, alkyl, halogen, alkoxy, hydroxyl, mercapto, carboxy and especially phenyl. The heteroatom(s) as well as the carbon atoms of the group may be substituted. The heteroatom(s) may also be in oxidized form.

The term "alkoxy" as used herein refers to a $C_{1-10}$alkyl linked to an oxygen atom, or preferably $C_{1-7}$alkoxy, more preferably $C_{1-4}$alkoxy. Examples of alkoxy groups include, but are not limited to, groups, such as methoxy, ethoxy, n-butoxy, tert-butoxy and allyloxy.

The term "acyl" as used herein refers to the group —(O)CR where R is alkyl, especially $C_{1-7}$alkyl, such as methyl. Examples of acyl groups include, but are not limited to, acetyl, propanoyl and butanoyl.

The term "acyloxy" as used herein refers to the group —OC(O)R, wherein R is hydrogen, alkyl, especially $C_{1-7}$alkyl, such as methyl or ethyl, or phenyl or substituted alkyl as defined above.

The term "alkoxycarbonyl" as used herein refers to the group —COOR, wherein R is alkyl, especially $C_{1-7}$alkyl, such as methyl or ethyl.

The term "halogen" or "halo" as used herein refer to chlorine, bromine, fluorine, iodine and is especially fluorine.

The term "thioalkoxy" as used herein means a group —SR where R is an alkyl as defined above, e.g., methylthio, ethylthio, propylthio, butylthio and the like.

The term "heteroalkylaryl" as used herein means a heteroalkyl group, e.g., —O—CH$_2$— substituted with an aryl group, especially phenyl. The phenyl group itself may also be substituted with one or more substituents, such as halogen, especially fluoro and chloro, and alkoxy, such as methoxy.

The term "alkylsulfonyl" as used herein means a group —SO$_2$R wherein R is alkyl, especially $C_{1-7}$alkyl, such as methyl sulfonyl.

"Protecting group" refers to a chemical group that exhibits the following characteristics: 1) reacts selectively with the desired functionality in good yield to give a protected substrate that is stable to the projected reactions for which protection is desired; 2) is selectively removable from the protected substrate to yield the desired functionality; and 3) is removable in good yield by reagents compatible with the other functional group(s) present or generated in such projected reactions. Examples of suitable protecting groups may be found in Greene et al., "Protective Groups in Organic Synthesis", 2$^{nd}$ Ed., John Wiley & Sons, Inc., NY (1991). Preferred amino protecting groups include, but are not limited to, benzyloxycarbonyl (CBz), t-butyl-oxycarbonyl (Boc), t-butyldimethylsilyl (TBDMS), 9-fluorenylmethyl-oxycarbonyl (Fmoc), or suitable photolabile protecting groups, such as 6-nitroveratryloxy carbonyl (Nvoc), nitropiperonyl, pyrenylmethoxycarbonyl, nitrobenzyl, dimethyl dimethoxybenzyl, 5-bromo-7-nitroindolinyl and the like. Preferred hydroxy protecting groups include Fmoc, TBDMS, photolabile protecting groups, such as nitroveratryl oxymethyl ether (Nvom), methoxy methyl ether (Mom) and methoxy ethoxy methyl ether (Mem). Particularly preferred protecting groups include NPEOC (4-nitrophenethyloxycarbonyl) and NPEOM (4-nitrophenethyloxy-methyloxycarbonyl).

It will be appreciated that the compounds of formula (I) may exist in the form of optical isomers, racemates or diastereoisomers. For example, a compound of formula (I) wherein $R_2$ and $R_3$ are different residues or wherein $R_4$ and $R_5$ are different residues, is asymmetric and may have the R- or S- configuration. It is to be understood that the present invention embraces all enantiomers and their mixtures. Similar considerations apply in relation to starting materials exhibiting asymmetric carbon atoms as mentioned.

The compounds of the invention, e.g., the compounds of formula (I), may exist in free form or in salt form, e.g., in form of a pharmaceutically acceptable salt. A "pharmaceutically acceptable salt" of a compound means a physiologically and pharmaceutically acceptable salt that possesses the desired pharmacological activity of the parent compound and does not impart undesired toxicological effects. Such salts include:

1. acid addition salts, formed with inorganic acids, such as hydrochloric acid, hydrobromic acid, sulfuric acid, nitric acid, phosphoric acid and the like; or formed with organic acids, such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-napthalenesulfonic acid, 4-toluenesulfonic acid, camphorsulfonic acid, 3-phenylpropionic acid, trimethylacetic acid, tertiary butylacetic acid, lauryl sulfuric acid, gluconic acid, glutamic acid, hydroxynapthoic acid, salicylic acid, stearic acid, muconic acid and the like; or 2. salts formed when an acidic proton present in the parent compound either is replaced by a metal ion, e.g., an alkali metal ion, an alkaline earth ion, or an aluminum ion; or coordinates with an organic base, such as ethanolamine, diethanolamine, triethanolamine, tromethamine, N-methylglucamine and the like.

A compound of the invention, e.g., the compounds of formula (I), may act as a prodrug. "Prodrug" means any compound which releases an active parent drug according to formula (I) in vivo when such prodrug is administered to a mammalian subject. Prodrugs of a compound of formula (I) are prepared by modifying functional groups present in the compound of formula (I) in such a way that the modifications may be cleaved in vivo to release the parent compound. Prodrugs include compounds of formula (I) wherein a hydroxy, amino or sulfhydryl group is bonded to any group that may be cleaved in vivo to regenerate the free hydroxyl, amino or sulfhydryl group, respectively. Examples of prodrugs include, but are not limited to esters, e.g., acetate, formate and benzoate derivatives; carbamates, e.g., N,N-dimethylamino-carbonyl, of hydroxy functional groups in compounds of formula (I); and the like.

In the compounds of formula (I), the following significances are preferred individually or in any subcombination:

1. $R_1$ is a heteroaryl of formula (II.1) wherein $R_6$, $R_7$ and $R_9$ are hydrogen and $R_8$ is methyl or trifluoromethyl; or $R_6$, $R_7$ and $R_8$ are hydrogen and $R_9$ is fluoro; or $R_6$, $R_8$ and $R_9$ are hydrogen and $R_7$ is ethyl or methoxy; or $R_7$, $R_8$ and $R_9$ are hydrogen and $R_6$ is hydroxy; or $R_7$ and $R_8$ are hydrogen, $R_6$ is methoxy and $R_9$ is methyl; or $R_1$ is a heteroaryl of formula (III.1) wherein $R_6$, $R_7$ and $R_9$ are hydrogen and $R_8$ is fluoro or trifluoromethyl; or $R_6$, $R_8$ and $R_9$ are hydrogen and $R_7$ is ethyl; preferably $R_1$ is a heteroaryl of formula (II.1) wherein $R_6$, $R_8$ and $R_9$ are hydrogen and $R_7$ is ethyl or a heteroaryl of formula (III.1) wherein $R_6$, $R_7$ and $R_9$ are hydrogen and $R_8$ is fluoro.
2. X is —$CH_2$—, —CH(OH)—, —CH(OR)—, —$CF_2$— or —CH(F)—, preferably X is —$CH_2$—.
3. $R_2$, $R_3$ and $R_4$ are hydrogen.
4. $R_5$ is alkyl, preferably $C_{1-7}$alkyl such as n-butyl.
5. n is 1.

The present invention also provides a process for preparing a compound of the invention, e.g., a compound of formula (I) which process comprises reacting a compound of formula (V)

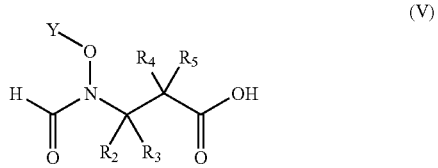

(V)

wherein $R_2$, $R_3$, $R_4$ and $R_5$ are as defined above and Y is a hydroxy protecting group, or a functional derivative thereof, with a compound of formula (VI)

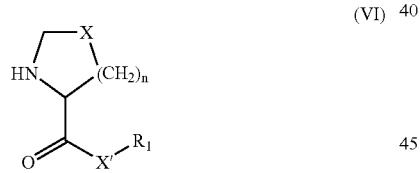

(VI)

wherein $R_1$, X and n are as defined above, and X' is NH or O, and where required, converting the resulting compounds obtained in free form into salt forms or vice versa.

Functional derivatives of compounds of formula (V) include, e.g., halogenides, such as acid chloride, acid anhydride or an activated ester.

Above reactions may be carried out according to methods known in the art or as disclosed in the Examples below. The reaction may conveniently be carried out in the presence of a base and then followed by hydrogenation, prefereably in the presence of a hydrogenation catalyst. Suitable bases include, e.g., Hunig base, such as diisopropylethylamine and inorganic bases, such as sodium bicarbonate. The hydrogenation catalyst, preferably a palladium catalyst, e.g., palladium on carbon or palladium black, may then be added to the resulting product, e.g., after concentration and stirred under a hydrogen atmosphere, e.g., for about 16 to about 24 hours. The palladium catalyst may be added preferably from about 5 mol % to about 10 mol % of the concentrated product.

Compounds of formula (V), used as starting materials, may be prepared, e.g., by reacting a compound of formula (VII)

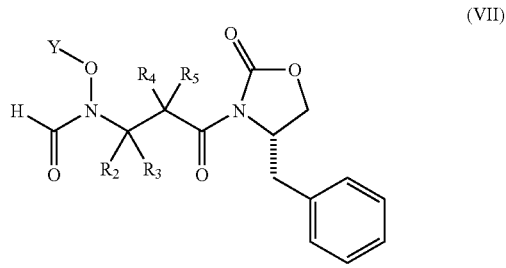

(VII)

wherein $R_2$, $R_3$, $R_4$, $R_5$ and Y are as defined above, e.g., under mild basic conditions, e.g., as known in the art. Typically, this reaction may be carried out by dissolving the compound of formula (VII), e.g., in a mixture of an inert solvent, such as THF, DMF, toluene, dioxane or $CH_2Cl_2$, and water, and adding hydrogen peroxide and then an aqueous solution of the base in water to the cooled mixture. Examples of base include, e.g., sodium bicarbonate, lithium hydroxide, sodium hydroxide and the like. The base may be used preferably at from about 1.1 equivalents to about 1.5 equivalents to the compound of formula (VII).

Compounds of formula (VII) may be produced, e.g., by reacting a compound of formula (VIII) wherein $R_2$, $R_3$, $R_4$, $R_5$ and Y are as defined above, with formic acid as known in the art. The reaction may typically be carried out, e.g., at 0° C., by adding a solution of acetic anhydride in formic acid to a solution of a compound of formula (VIII) in formic acid.

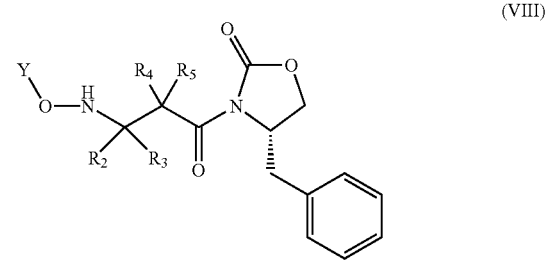

(VIII)

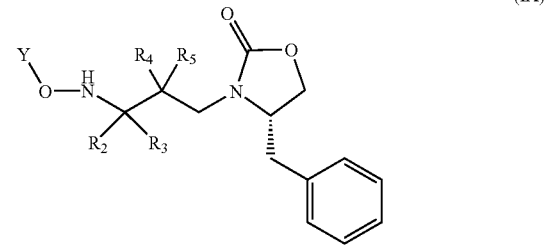

(IX)

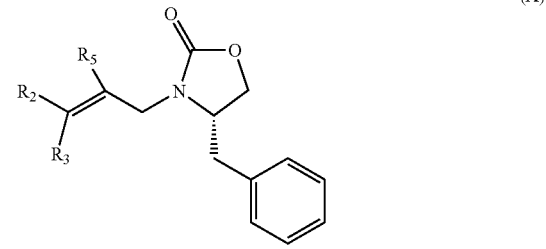

(X)

-continued

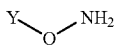
(XI)

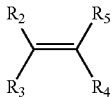
(XII)

Compounds of formula (VIII) may be prepared e.g. by reacting a compound of formula (IX) wherein $R_2$, $R_3$, $R_4$ and $R_5$ are as defined above, with a solution of p-toluenesulfonic acid in an inert organic solvent, and a solution of $Na_2CO_3$, e.g., 1 M, as known in the art.

Compounds of formula (IX) may be prepared, e.g., by reacting a compound of formula (X) wherein $R_2$, $R_3$ and $R_5$ are as defined above, with a hydroxy protected compound of formula (XI) wherein Y is aryl, alkyl, aralkyl or silyl, as known in the art.

The compound of formula (X) may be produced, e.g., by reacting a compound of formula (XII) with pivaloyl chloride, wherein $R_4$ is as defined above, as known in the art.

Insofar as the production of starting materials is not particularly described, the compounds are known or may be prepared analogously to methods known in the art or as disclosed in the examples hereinafter.

The following abbreviations are used:
DIEA=diisopropylethylamine
DMF=dimethylformamide
DMSO=dimethylsulfoxide
EtOAc=ethyl acetate
FC=flash chromatography
HATU=O-(7-aza-benzotriazol-1-yl)-N,N,N',N'-tetramethyluronium hexafluorophosphate
MCPBA=meta-chloroperoxy-benzoic acid
PFP=pentafluorophenyl
p-TSA=p-toluenesulfonic acid
rt=room temperature
TFA=trifluoroacetic acid
THF=tetrahydrofuran General Procedure A Synthesis of 1-{2(R)-[(formylhydroxyamino)-methyl]-alkanoyl}-pyrrolidine-2(S)-carboxylic acid amide (Scheme)

Step 1: 2-n-butyl acrylic acid (A-2)

To a solution of alkyl malonic acid A-1 (R=n-butyl (107.4 mmol) in ethanol (200 mL) is added piperidine (12.7 mL, 128.8 mmol, 1.2 equiv.) and 37% aqueous formaldehyde (40.0 mL, 536.9 mmol, 5 equiv.). The solution is heated to 80° C. during which time a precipitate appears, and then gradually re-dissolves over 1 hour. The reaction mixture is stirred at 80° C. overnight then cooled to rt. The solvents are removed under reduced pressure, and the residue is dissolved in EtOAc, washed successively with 1 M HCl and brine, dried over anhydrous $Na_2SO_4$ and filtered. The filtrate is concentrated to give the title compound A-2 as a clear oil.

Step 2: 4-benzyl-3-(2-butyl-acryloyl)-oxazolidin-2-one (A-3)

2-n-butyl acrylic acid (9.90 g, 77.2 mmol, and 1 equiv.) is dissolved in dry THF (260 mL) and cooled to −78° C. under nitrogen. Hunig's base (17.5 mL, 100.4 mmol, 1.3 equiv.) and pivaloyl chloride (9.5 mL, 77.2 mmol, 1 equiv.) are added at such a rate that the temperature remains below −60° C. The mixture is stirred at −78° C. for 30 minutes, warmed to rt for 2 hours, and finally cooled back to −78° C. In a separate flask, (S)-(−)-4-benzyl-2-oxazolidinone (13.49 g, 77.24 mmol) is dissolved in dry THF (150 mL) and cooled to −78° C. under nitrogen. n-butyllithium (2.5 M solution in hexanes, 30.9 mL, 77.2 mmol, 1 equiv.) is added slowly at −78° C., and the mixture is stirred for 30 minutes at rt. The resulting anion is slowly transferred via a cannula into the original reaction vessel. The mixture is allowed to warm to rt and is stirred overnight at rt. The reaction is quenched with 1 M $KHCO_3$, and the solvents are removed under reduced pressure. The residue is partitioned between EtOAc and water. The organic layer is washed with brine, dried over anhydrous $Na_2SO_4$, filtered and concentrated to give a yellow oil which is purified by FC (hexane:EtOAc=4:1) to yield the title compound A-3 as a white solid.

1H NMR ($CDCl_3$): δ 7.39–7.20 (m, 5H), 5.42–5.40 (d, J=7.14 Hz, 2H), 4.76–4.68 (m, 1H), 4.29–4.16 (m, 2H), 3.40–3.35 (dd, J=3.57, 13.46 Hz, 1H), 2.86–2.79 (dd, J=9.34, 13.46 Hz, 1H), 2.42–2.37 (t, J=7.69 Hz, 2H), 1.55–1.30 (m, 4H), 0.95–0.90 (t, J=7.14 Hz, 3H). ES-MS: calcd. For $C_{17}H_{21}NO_3$ (287.35); found: 288.5 [M+H].

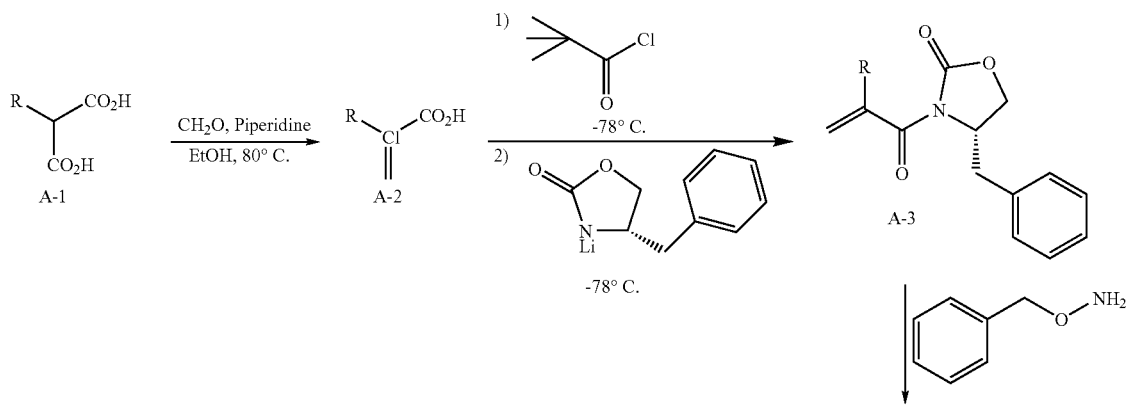

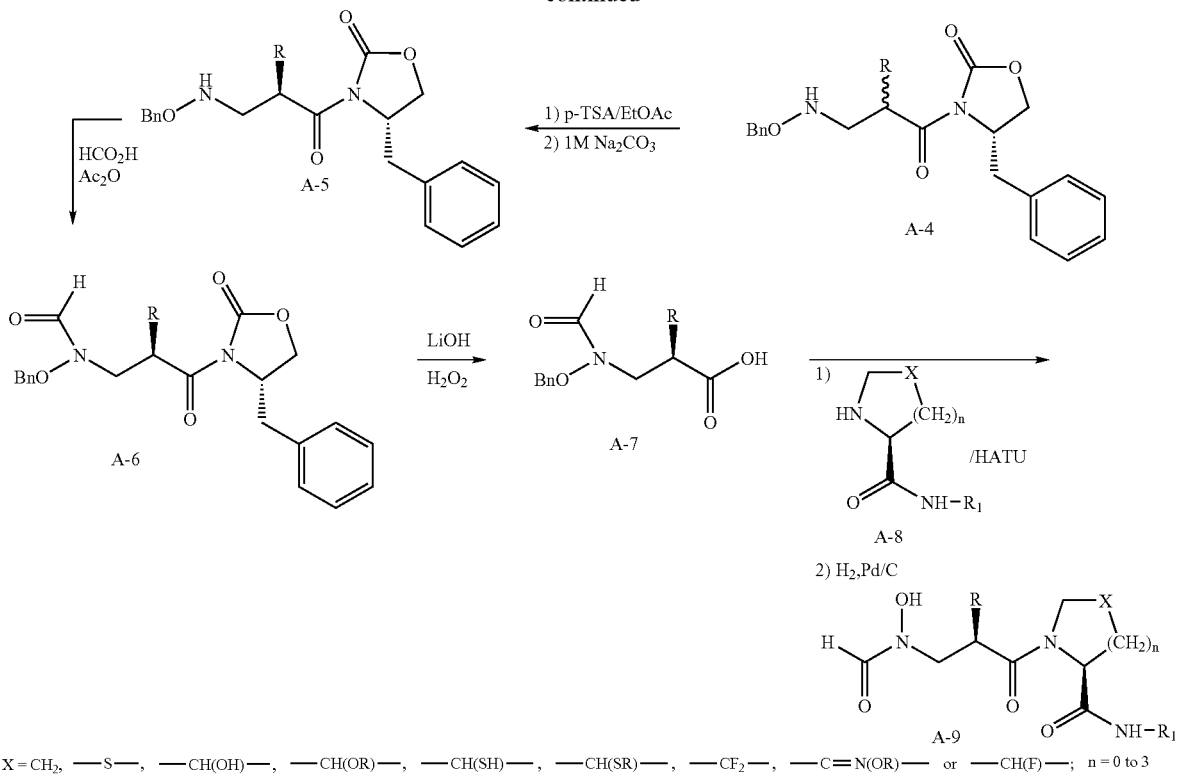

X = CH$_2$, —S—, —CH(OH)—, —CH(OR)—, —CH(SH)—, —CH(SR)—, —CF$_2$—, —C=N(OR)— or —CH(F)—; n = 0 to 3

Step 3: 4-benzyl-3-[2-(benzyloxyamino-methyl)-hexanoyl]-oxazolidin-2-one (p-toluenesulfonic acid salt)

Compound A-3 (8.25 g, 28.7 mmol) is mixed with O-benzylhydroxylamine (7.07 g, 57.4 mmol, 2 equiv.) and stirred for 40 hours at rt under nitrogen. The mixture is dissolved in EtOAc and p-TSA (21.84 g, 114.8 mmol, and 4 equiv.) is added to precipitate excess O-benzylhydroxylamine as a white solid. The white solid is filtered off, and the filtrate is concentrated to give a crude yellow oil (HPLC analysis indicated a small trace of starting material). Charging the crude yellow oil with excess diethyl ether and cooling to 0° C. for 30 minutes gives a solid which is collected by filtration and dried in vacuo to afford the title compound as a white crystalline solid (single diastereomer).

1H NMR (CDCl$_3$): δ 8.07–8.04 (d, J=8.24, 2H), 7.59–7.39 (m, 10H), 7.18–7.15 (d, J=7.69 Hz, 2H), 5.49–5.40 (q, J=8.61 Hz, 2H), 4.65–4.56 (m, 1H), 4.25–4.08 (m, 3H), 3.83–3.79 (d, J=13.46 Hz, 1H), 3.15–3.11 (d, J=13.46 Hz, 1H), 2.56 (s, 3H), 1.83–1.67 (m, 4H), 1.40 (bs, 4H), 1.00–0.951 (t, J=6.87, 3H). ES-MS: calcd. For C$_{24}$H$_{30}$N$_2$O$_4$*C$_7$H$_8$O$_3$S (582.71); found: 411.7 [M+H] free base.

Step 4: 4-benzyl-3-[2-(benzyloxyamino-methyl)-hexanoyl]-oxazolidin-2-one (A-5)

To a solution of p-TSA (22.9 g, 39.3 mmol) dissolved in EtOAc (400 mL), is added 1 M Na$_2$CO$_3$ (200 mL, 5 equiv.) and stirred at rt for 30 minutes. The layers are separated, and the aqueous layer extracted with EtOAc. The combined organic layers are dried over anhydrous Na$_2$SO$_4$, filtered and concentrated to give the title compound as a pale opaque oil.

1H NMR (CDCl$_3$): δ 7.57–7.38 (m, 10H), 4.98–4.90 (m, 2H), 4.87–4.79 (m, 1H), 4.38–4.28 (m, 3H), 3.64–3.57 (dd, J=9.21, 12.64 Hz, 1H), 3.46–3.36 (td, J=3.76, 13.05 Hz, 2H), 2.68–2.60 (dd, J=10.03, 13.46 Hz, 1H), 1.90–1.88 (m, 1H), 1.78–1.71 (m, 1H), 1.51–1.44 (m, 4H), 1.10–1.06 (t, J=6.73 Hz, 3H). ES-MS: calcd. For C$_{24}$H$_{30}$N$_2$O$_4$ (410.51); found: 411.7 [M+H].

Step 5: N-[2-(4-benzyl-2-oxo-oxazolidine-3-carbonyl)-hexyl]-N-benzyloxy-formamide (A-6)

A solution of compound A-5 (5.38 g, 13.1 mmol, 1 equiv.) in formic acid (7.4 mL, 196.6 mmol, 15 equiv.) is cooled to 0° C. under nitrogen. In a separate flask, formic acid (7.4 mL, 196.6 mmol, 15 equiv.) is cooled to 0° C. under nitrogen, and acetic anhydride (2.47 mL, 26.2 mmol, 2 equiv.) is added dropwise. The solution is stirred at 0° C. for 15 minutes. The resulting mixed anhydride is slowly transferred via syringe into the original reaction vessel. The mixture is stirred at 0° C. for 1 hour, then at rt for 3 hours. The mixture is concentrated, taken up in CH$_2$Cl$_2$, and washed successively with saturated NaHCO$_3$ and brine. The organic layer is dried over anhydrous Na$_2$SO$_4$, filtered and concentrated to give an opaque oil which is purified by FC (hexane:EtOAc=2:1 then CH$_2$Cl$_2$:acetone=9:1) to yield the title compound as a colorless oil.

1H NMR (CDCl$_3$, rotamers): δ 8.38 (s, 0.7H), 8.21 (s, 0.3H), 7.54–7.35 (m, 10H), 5.0–5.00 (m, 2H), 4.88–4.81 (m, 1H), 4.39–4.29 (m, 4H), 4.07–4.03 (m, 1H), 3.43–3.39 (m, 1H), 2.66–2.58 (m, 1H), 1.89 (bs, 1H), 1.73 (bs, 1H), 1.49–1.44 (m, 3H), 1.10–1.06 (t, J=6.73 Hz, 3H). ES-MS: calcd. For C$_{25}$H$_{30}$N$_2$O$_5$ (438.52); found: 439.7 [M+H].

Step 6: 2-[(benzyloxy-formyl-amino)-methyl]-hexanoic acid (A-7)

Compound A-6 (0.163 g, 0.372 mmol, 1 equiv.) is dissolved in THF (4.5 ml) and water (1.5 mL) and cooled to 0°

C. Hydrogen peroxide (30% in water, 228 μL, 2.23 mmol, 6 equiv.) is added dropwise followed by the slow addition of a solution of lithium hydroxide (0.019 g, 0.446 mmol, 1.2 equiv.) in water (350 μL). The resulting mixture is stirred at 0° C. for 1.5 hours. The basic reaction mixture is quenched with Amberlite IR-120 resin (H+) to pH 4–5 at 0° C. The resin is filtered off and rinsed with EtOAc. The mixture is concentrated to remove THF, and then taken up in EtOAc. The aqueous layer is separated, and the organic layer dried over anhydrous $Na_2SO_4$, filtered and concentrated to give an opaque oil which is purified by FC ($CH_2Cl_2$:acetone=4:1 then acetone:methanol=99:1) to yield the title compound A-7 as a colorless oil.

1H NMR (DMSO-$d_6$, rotamers): δ 11.2 (s, 1H), 8.20 (s, 0.2H), 7.95 (s, 0.8H), 7.33–7.41 (m, 5H), 4.87 (s, 2H), 3.71 (bs, 2H), 2.50 (bs, 1H), 1.35–1.45 (m, 2H), 1.14–1.28 (m, 4H), 0.857–0.813 (t, J=13.1 Hz, 3H). ES-MS: calcd. For $C_{15}H_{21}NO_4$ (279.33); found: 278.5 [M−H], 302.5 [M+Na].

Step 7: 1-{2-[(benzyloxy-formyl-amino)-methyl]-hexanoyl}-pyrrolidine-2-carboxylic acid amide To a solution of compound A-7 (0.190 g, 0.680 mmol, 1 equiv.) in dry dioxane (4 mL) at rt under nitrogen is added successively Hunig's base (391 μL, 2.24 mmol, 3.3 equiv.), amine A-8 (0.748 mmol, 1.1 equiv.) and HATU (0.284 g, 0.748 mmol, 1.1 equiv.). The resulting mixture is stirred at rt for 22 hours. The mixture is partitioned between EtOAc and 10% citric acid. The organic layer is washed with brine and saturated $NaHCO_3$, dried over anhydrous $Na_2SO_4$, filtered and concentrated. The residue is purified by FC ($CH_2Cl_2$:acetone=3:1) to give the title compound as a colorless oil.

Step 8: 1-{2-[(formyl-hydroxy-amino)-methyl]-hexanoyl}-pyrrolidine-2-carboxylic acid amide (A-9)

Pd—C (0.059 g, 0.1 equiv.) is added to a solution of above compound (0.550 mmol, 1 equiv.) in a 1:1 EtOAc/ethanol solution (12 mL) under nitrogen. The mixture is stirred under hydrogen atmosphere for 36 hours. The catalyst is removed by filtration through a pad of Celite. The filtrate is concentrated, and the residue is purified by preparative TLC ($CH_2Cl_2$:acetone=2:1) to give the title compound as an amorphous solid.

General Procedure B

Synthesis of 1-{2(R)-[(formylhydroxyamino)-methyl]-alkanoyl}-pyrrolidine-2(S)-carboxylate ester

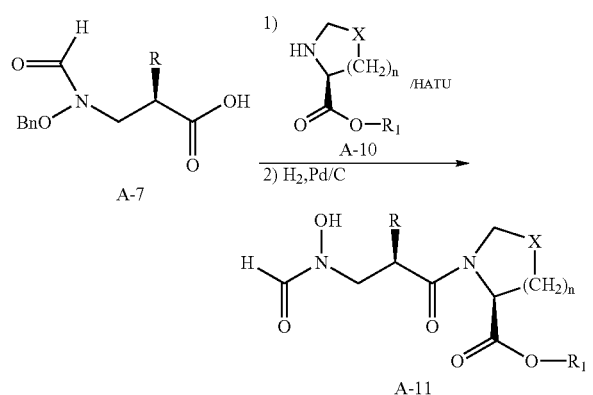

X=$CH_2$, —S—, —CH(OH)—, —CH(OR)—, —CH(SH)—, —CH(SR)—, —$CF_2$—, —C=N(OR)— or —CH(F)—; n=0 to 3

Step 1: 1-{2-[(benzyloxy-formyl-amino)-methyl]-hexanoyl}-pyrrolidine-2-carboxylic acid ester To a solution of compound A-7 (0.680 mmol, 1 equiv.) in dry dioxane (4 mL) at rt under nitrogen is added successively Hunig's base (391 μL, 2.24 mmol, 3.3 equiv.), amine A-10 (0.748 mmol, 1.1 equiv.) and HATU (0.284 g, 0.748 mmol, 1.1 equiv.). Usual work-up and purification provides the title compound.

Step 8: 1{2-[(formyl-hydroxy-amino)-methyl]-hexanoyl}-pyrrolidine-2-carboxylic acid ester (A-11)

Pd—C (0.059 g, 0.1 equiv.) is added to a solution of above compound (0.550 mmol) in a 1:1 EtOAc/ethanol solution (12 mL) under nitrogen. The mixture is stirred under hydrogen atmosphere for 36 hours. By following the same procedure as disclosed above, the title compound is obtained.

The following examples are to illustrate the invention but should not be interpreted as a limitation thereon.

EXAMPLE 1

1-{2-R-[(formyl-hydroxy-amino)-methyl]-hexanoyl}-pyrrolidine-2-S-carboxylic acid pyridin-2-ylamide

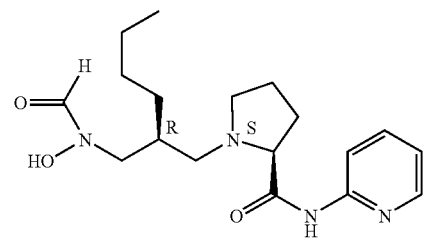

The title compound is prepared according to General Procedure A from 2-[(benzyloxy-formyl-amino)-methyl]-hexanoic acid A-7 (R=n-butyl) and pyrrolidine-2-carboxylic acid pyridin-2-ylamide A-8 (X=$CH_2$, n=1, $R_1$=2-pyridyl).

1H NMR (DMSO-$d_6$): δ 10.7 (s, 1H), 9.89 (s, 1H), 8.50–8.44 (m, 1H), 8.23–8.17 (m, 1H), 7.97–7.92 (m, 2H), 7.29–7.25 (m, 1H), 4.83–4.71 (m, 1H), 3.91–3.51 (m, 4H), 3.30–3.15 (m, 1H), 2.46–1.83 (m, 4H), 1.52–1.31 (m, 6H), 1.11–0.93 (m, 3H). ES-MS: calcd. for $C_{18}H_{26}N_4O_4$ (362.42); found: 363.6 [M+H], 385.5 [M+Na].

Preparation of pyrrolidine-2-S-carboxylic acid (pyridin-2-yl) amide A-8 (X=$CH_2$, n=1, $R_1$=2-pyridyl)

2-S-(pyridin-2-ylcarbamoyl)-pyrrolidine-1-carboxylic acid benzyl ester

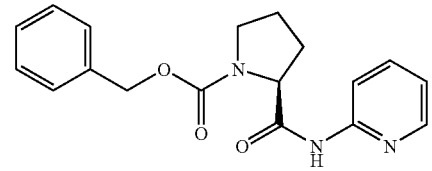

A solution of 2-S-(chlorocarbonyl)-pyrrolidine-1-carboxylic acid benzyl ester (5.0 g, 18.7 mmol, 1 equiv.) in pyridine (40 mL) is cooled to 0° C. under nitrogen. 2-aminopyridine (5.27 g, 56.0 mmol, 3 equiv.) in pyridine (10 mL) is added dropwise. The resulting mixture is stirred at rt for 4 hours, then concentrated. The residual oil is dissolved in EtOAc and washed successively with water, 10% citric acid, saturated NaHCO$_3$ and brine. The organic layer is dried over anhydrous Na$_2$SO$_4$, filtered and concentrated to give the title compound as an opaque solid.

1H NMR (DMSO-d$_6$): δ 10.8–10.7 (d, J=15.6 Hz, 1H), 8.51–8.49 (m, 1H), 8.29–8.24 (m, 1H), 8.01–7.93 (m, 1H), 7.57–7.48 (m, 3H), 7.40–7.25 (m, 3H), 5.31–0.22 (m, 2H), 4.76–4.68 (m, 1H), 3.72–3.58 (m, 2H), 2.50–2.31 (m, 1H), 2.14–1.95 (m, 3H).

Pyrrolidine-2-S-carboxylic Acid (pyridin-2-yl) amide hydrobromic acid salt

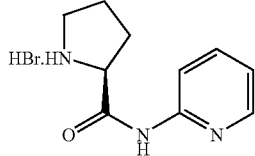

A solution of above compound (4.21 g, 13.0 mmol, 1 equiv.) in AcOH (65 mL) at rt is treated with HBr (5.7 M, 33% in AcOH, 110 mL, 649 mmol, 50 equiv.), and the mixture is stirred at rt for 2 hours. Charging the reaction mixture with excess diethyl ether and cooling to 0° C. for 30 minutes gives a solid which is collected by filtration and dried in vacuo to afford the title compound as a brownish powder.

1H NMR (DMSO-d$_6$): δ 11.3 (s, 1H), 8.89 (bs, 1H), 8.57–8.5 (m, 1H), 8.24–8.22 (m, 1H), 8.08–8.03 (m, 1H), 7.40–7.36 (m, 1H), 4.61 (bs, 1H), 3.47–3.45 (m, 2H), 2.65–2.55 (m, 1H), 2.21–2.07 (m, 3H). ES-MS: calcd. for C$_{10}$H$_{13}$N$_3$O*2HBr (353.05); found: 192.4 [M+H] free base.

EXAMPLE 2

1-{2-R-[(formyl-hydroxy-amino)-methyl]-hexanoyl}-pyrrolidine-2-S-carboxylic acid-(3-methyl-pyridin-2-yl)-amide

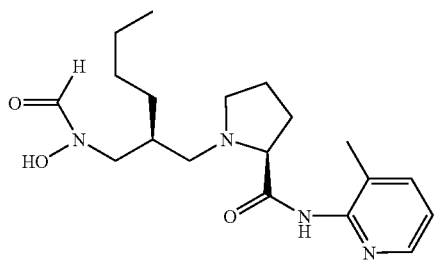

The title compound is prepared according to General Procedure A from 2-[(benzyloxy-formyl-amino)-methyl]-hexanoic acid A-7 (R=n-butyl) and pyrrolidine-2-carboxylic acid (3-methyl-pyridin-2-yl)-amide A-8 [X=CH$_2$, n=1, R$_1$=2-(3-methyl)pyridyl]. A-8 is prepared from 2-chlorocarbonyl-pyrrolidine-1-carboxylic acid benzyl ester and 3-picoline as described for the synthesis of pyrrolidine-2-carboxylic acid pyridin-2-yl-amide (hydrobromic acid salt) in Example 1.

1H NMR (DMSO-d$_6$): δ 8.45–8.42 (m, 1H), 8–7.8 (m, 1H), 7.4–7.36 (dd, 1H), 4.7 (bs, 1H), 3.8 (m, 4H), 3.15–3.3 (m, 1H), 2.37–2.3 (bs, 3H), 2.12 (bs, 4H), 1.65–1.43 (m, 6H), 1.03–1 (d, J=6.2 Hz, 3H). ES-MS: calcd. for C$_{19}$H$_{28}$N$_4$O$_4$ (376.45); found: 377.7 [M+H].

EXAMPLE 3

1-{2-R-[(formyl-hydroxy-amino)-methyl]-hexanoyl}-pyrrolidine-2-S-carboxylic acid-(6-methyl-pyridin-2-yl)-amide

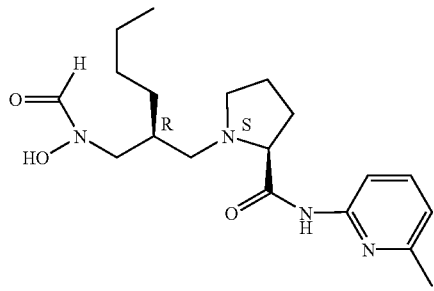

The title compound is prepared according to General Procedure A from 2-[(benzyloxy-formyl-amino)-methyl]-hexanoic acid A-7 (R=n-butyl) and pyrrolidine-2-carboxylic acid (6-methyl-pyridin-2-yl)-amide A-8 (X=CH$_2$, n=1, R$_1$=2-(6-methyl)pyridyl). A-8 is prepared from 2-chlorocarbonyl-pyrrolidine-1-carboxylic acid benzyl ester and 6-picoline as described for the synthesis of pyrrolidine-2-carboxylic acid pyridin-2-yl-amide (hydrobromic acid salt) in Example 1.

1H NMR (DMSO-d$_6$): δ 8.04–7.8 (m, 1H), 7.2–7.12 (d, J=7.42 Hz, 1H), 4.75–4.73 (d, J=4.4 Hz, 1H), 3.85–3.71 (m, 4H), 3.21 (bs, 1H), 2.58 (bs, 3H), 2.3–2.1 (m, 4H), 1.67–1.42 (m, 6H), 1.06–1.04 (d, J=6.3 Hz, 3H). ES-MS: calcd. for C$_{19}$H$_{28}$N$_4$O$_4$ (376.45); found: 377.7 [M+H].

EXAMPLE 4

1-{2-R-[(formyl-hydroxy-amino)-methyl]-hexanoyl}-pyrrolidine-2-S-carboxylic Acid-(4-methyl-pyridin-2-yl)-amide

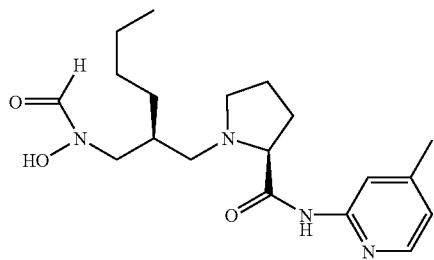

The title compound is prepared according to General Procedure A from 2-[(benzyloxy-formyl-amino)-methyl]- hexanoic acid A-7 (R=n-butyl) and pyrrolidine-2-carboxylic acid (4-methyl-pyridin-2-yl)-amide A-8 (X=CH$_2$, n=1, R$_1$=2-(4-methyl)pyridyl).

1H NMR (DMSO-d$_6$): δ 8.35–8.34 (d, J=4.67 Hz, 1H), 8.08–7.98 (d, 1H), 4.75–4.73 (d, J=4.67 Hz, 1H), 4.74 (bs, 1H), 3.73 (bs, 2H), 3.52 (bs, 2H), 2.49 (bs, 3H), 2.27–2.05 (m, 4H), 1.66–1.46 (m, 6H), 1.05 (bs, 3H). ES-MS: calcd. for C$_{19}$H$_{28}$N$_4$O$_4$ (376.46); found: 377.7 [M+H].

A-8 is prepared from 2-chlorocarbonyl-pyrrolidine-1-carboxylic acid benzyl ester and 4-picoline as described for the synthesis of pyrrolidine-2-carboxylic acid pyridin-2-yl-amide (hydrobromic acid salt) in Example 1.

2-S-(4-methyl-pyridin-2-ylcarbamoyl)-pyrrolidine-1-carboxylic acid benzyl ester

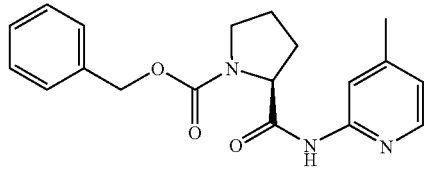

1H NMR (DMSO-d$_6$): δ 8.33 (bs, 1H), 8.17–8.13 (m, 1H), 7.81–7.77 (m, 1H), 7.6–7.3 (m, 4H), 5.9–5.11 (m, 2H), 4.72–4.66 (m, 1H), 3.68–3.61 (m, 2H), 2.44 (bs, 3H), 2.34–1.98 (m, 4H). ES-MS: calcd. for C$_{19}$H$_{21}$N$_3$O$_3$ (339.39); found: 340.6 [M+H].

Pyrrolidine-2-S-carboxylic Acid (4-methyl-pyridin-2-yl) amide hydrobromic acid salt

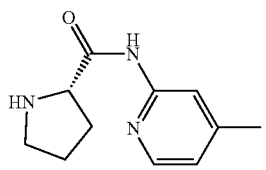

1H NMR (DMSO-d$_6$): δ 8.45–8.43 (d, 1H, J=5.2 Hz), 8.03 (bs, 1H), 7.29–7.28 (d, J=5.2 Hz, 1H), 4.64 (bs, 1H), 3.47 (bs, 2H), 2.63 (bs, 3H), 2.56–2.07 (m, 4H). ES-MS: calcd. for C$_{11}$H$_{15}$N$_3$O (205.12); found: 206.4 [M+H].

EXAMPLE 5

1-{2-R-[(formyl-hydroxy-amino)-methyl]-hexanoyl}-pyrrolidine-2-S-carboxylic acid-(5-fluoro-pyridin-2-yl)-amide

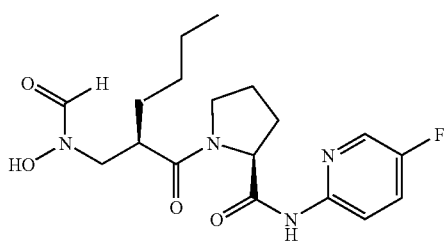

The title compound is prepared according to General Procedure A from 2-[(benzyloxy-formyl-amino)-methyl]-hexanoic acid A-7 (R=n-butyl) and pyrrolidine-2-carboxylic acid (5-fluoro-pyridin-2-yl)-amide A-8 (X=CH$_2$, n=1, R$_1$=2-(5-fluoro)pyridyl).

1H NMR (DMSO-d$_6$): δ 8.51–8.44 (m, 1H), 8.3–8.25 (m, 1H), 7.97–7.88 (m, 1H), 4.75 (bs, 1H), 3.82–3.72 (m, 2H), 3.65–3.52 (m, 2H), 3.21 (bs, 1H), 2.7–2.68 (m, 4H), 2.3–1.45 (m, 6H), 1.04 (d, 3H). ES-MS: calcd. for C$_{18}$H$_{25}$FN$_4$O$_4$ (380.42); found: 381.7 [M+H].

A-8 is prepared from 2-chlorocarbonyl-pyrrolidine-1-carboxylic acid benzyl ester and 5-fluoro-pyridin-2-ylamine as described for the synthesis of pyrrolidine-2-carboxylic acid pyridin-2-yl-amide (hydrobromic acid salt) in Example 1.

Pyrrolidine-2-S-carboxylic acid (5-fluoro-pyridin-2-yl) amide hydrobromic acid salt

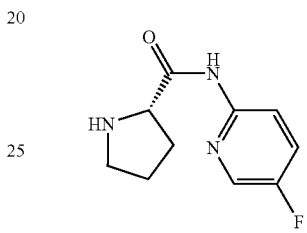

1H NMR (DMSO-d$_6$): δ 8.58–8.57 (d, J=3.02 Hz, 1H), 8.3–8.25 (m, 1H), 8.05–7.83 (m, 1H), 4.62–4.59 (d, J=7.87 Hz, 1H), 3.46 (bs, 2H), 2.69–2.55 (m, 1H), 2.21–2.06 (m, 3H). ES-MS: calcd. for C$_{10}$H$_{12}$FN$_3$O (209.1); found: 210.4 [M+H].

EXAMPLE 6

1-{2-R-[(formyl-hydroxy-amino)-methyl]-hexanoyl}-pyrrolidine-2-S-carboxylic acid-(5-methyl-pyridin-2-yl)-amide

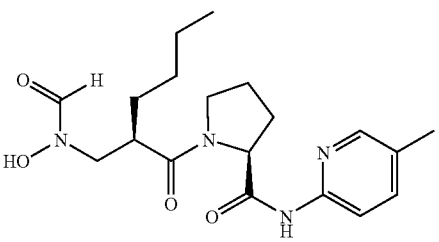

The title compound is prepared according to General Procedure A from 2-[(benzyloxy-formyl-amino)-methyl]-hexanoic acid A-7 (R=n-butyl) and pyrrolidine-2-carboxylic acid (5-methyl-pyridin-2-yl)-amide A-8 (X=CH$_2$, n=1, R$_1$=2-(5-methyl)pyridyl).

1H NMR (DMSO-d$_6$): δ 7.95–7.92 (d, J=8.52 Hz, 1H), 7.78 (bs, 1H), 7.6–7.58 (m, 1H), 4.55 (bs, 1H), 3.88–3.54 (bs, 2H), 3.33–3.29 (bs, 2H), 3.1–2.9 (m, 1H), 2.24 (bs, 3H), 2.11–1.87 (m, 4H), 1.48–1.26 (m, 6H), 0.87–0.85 (d, 3H). ES-MS: calcd. for C$_{19}$H$_{28}$N$_4$O$_4$ (376.46); found: 377.7 [M+H].

A-8 is prepared from 2-chlorocarbonyl-pyrrolidine-1-carboxylic acid benzyl ester and 5-methyl-pyridin-2-ylamine as described for the synthesis of pyrrolidine-2-carboxylic acid pyridine-2-yl-amide (hydrobromic acid salt) in Example 1.

2-S-(5-methyl-pyridin-2-ylcarbamoyl)-pyrrolidine-1-carboxylic acid benzyl ester

1H NMR (DMSO-$d_6$): δ 8.36–8.35 (d, J=4.7 Hz, 1H), 8.12 (bs, 1H), 7.57–7.14 (m, 5H), 5.3–5.11 (m, 2H), 4.74–4.68 (t, J=9.34 Hz, 1H), 3.7–3.62 (m, 2H), 2.52 (bs, 3H), 2.41–2.06 (m, 4H). ES-MS: calcd. for $C_{19}H_{21}N_3O_3$ (339.39); found: 340.6 [M+H].

Pyrrolidine-2-S-carboxylic acid (5-methyl-pyridin-2-yl) Amide Hydrobromic acid salt

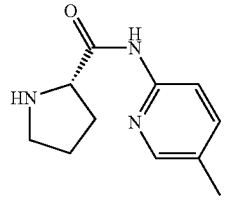

1H NMR (DMSO-$d_6$): δ 8.45–8.43 (d, 1H, J=5.2 Hz), 8.03 (bs, 1H), 7.29–7.28 (d, J=5.2 Hz, 1H), 4.64 (bs, 1H), 3.47 (bs, 2H), 2.63 (bs, 3H), 2.56–2.07 (m, 4H). ES-MS: calcd. for $C_{11}H_{15}N_3O$ (205.12); found: 206.4 [M+H].

EXAMPLE 7

1-{2-R-[(formyl-hydroxy-amino)-methyl]-hexanoyl}-pyrrolidine-2-S-carboxylic acid-(6-ethyl-pyridin-2-yl)-amide

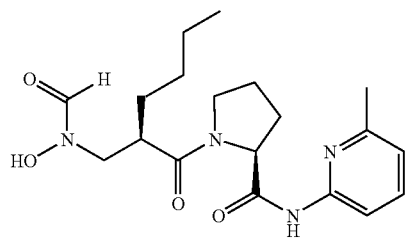

The title compound is prepared according to General Procedure A from 2-[(benzyloxy-formyl-amino)-methyl]-hexanoic acid A-7 (R=n-butyl) and pyrrolidine-2-carboxylic acid (6-ethyl-pyridin-2-yl)-amide A-8 [X=CH$_2$, n=1, R$_1$=2-(6-ethyl)pyridyl].

1H NMR (DMSO-$d_6$): δ 8.06–7.83 (m, 2H), 7.17–7.14 (d, J=7.69 Hz, 1H), 4.77 (bs, 1H), 3.83–3.78 (m, 2H), 3.58–3.32 (m, 2H), 3.05 (bs, 1H), 2.87–2.83 (m, 2H), 2.3–2.07 (m, 3H), 1.65–1.38 (m, 10H), 1.04 (bs, 3H). ES-MS: calcd. for $C_{20}H_{30}N_4O_4$ (390.48); found: 391.4 [M+H].

A-8 is prepared from 2-chlorocarbonyl-pyrrolidine-1-carboxylic acid benzyl ester and 6-ethyl-pyridin-2-ylamine as described for the synthesis of pyrrolidine-2-carboxylic acid pyridine-2-yl-amide (hydrobromic acid salt) in Example 1.

Pyrrolidine-2-S-carboxylic acid (6-ethyl-pyridin-2-ylamide (hydrobromic acid salt)

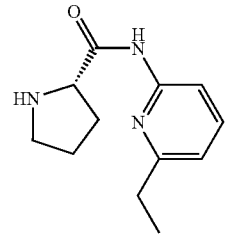

1H NMR (DMSO-$d_6$): δ 8.07–7.94 (m, 2H), 7.27–7.25 (d, J=7.42 Hz, 1H), 4.61 (bs, 1H), 3.46 (bs, 2H), 2.93–2.85 (m, 2H), 2.61–2.56 (m, 1H), 2.18–2.09 (m, 3H), 1.44–1.39 (m, 3H). ES-MS: calcd. for $C_{12}H_{17}N_3O$ (219.1); found: 220.2 [M+H].

EXAMPLE 8

1-{2-R-[(formyl-hydroxy-amino)-methyl]-hexanoyl}-pyrrolidine-2-S-carboxylic acid-(5-trifluoromethyl-pyridin-2-yl)-amide

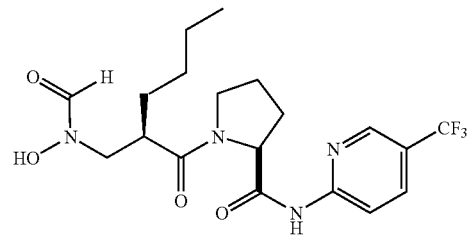

The title compound is prepared according to General Procedure A from 2-[(benzyloxy-formyl-amino)-methyl]-hexanoic acid A-7 (R=n-butyl) and pyrrolidine-2-carboxylic acid (5-trifluoromethyl-pyridin-2-yl)-amide A-8 [X=CH$_2$, n=1, R$_1$=2-(5-trifluoromethyl)pyridyl].

1H NMR (DMSO-$d_6$): δ 8.45–8.35 (m, 2H), 7.98 (bs, 1H), 4.8–4.78 (d, J=4.4 Hz, 1H), 3.84–3.73 (m, 2H), 3.54 (bs, 2H), 3.2 (bs, 1H), 2.34–2.1 (m, 4H), 1.65–1.46 (m, 6H), 1.05 (bs, 3H). ES-MS: calcd. for $C_{19}H_{25}F_3N_4O_4$ (430.43); found: 431.3 [M+H].

A-8 is prepared from 2-chlorocarbonyl-pyrrolidine-1-carboxylic acid benzyl ester and 5-trifluoromethyl-pyridin-2-ylamine as described for the synthesis of pyrrolidine-2-carboxylic acid pyridine-2-yl-amide (hydrobromic acid salt) in Example 1.

Pyrrolidine-2-S-carboxylic acid (5-trifluoromethyl-pyridin-2-ylamide (hydrobromic acid salt)

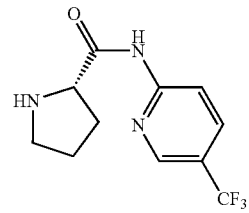

1H NMR (DMSO-d$_6$): δ 8.98 (bs, 1H, 8.49–8.40 (m, 2H), 4.67 (bs, 1H), 3.49–3.47 (d, 2H), 2.64–2.57 (m, 1H), 2.22–2.09 (m, 3H). ES-MS: calcd. for C$_{11}$H$_{12}$F$_3$N$_3$O (259.1); found: 260.2 [M+H].

EXAMPLE 9

1-{2-R-[(formyl-hydroxy-amino)-methyl]-hexanoyl}-pyrrolidine-2-S-carboxylic acid-(6-fluoro-pyridin-2-yl)-amide

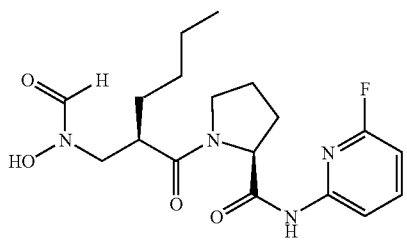

The title compound is prepared according to General Procedure A from 2-[(benzyloxy-formyl-amino)-methyl]-hexanoic acid A-7 (R=n-butyl) and pyrrolidine-2-carboxylic acid (6-fluoro-pyridin-2-yl)-amide A-8 [X=CH$_2$, n=1, R$_1$=2-(5-trifluoromethyl)pyridyl].

1H NMR (DMSO-d$_6$): δ 8.14 (bs, 1H), 8.04–7.97 (m, 1H), 7.04–7.02 (m, 1H), 4.70 (bs, 1H), 3.85–3.78 (m, 2H), 3.72–3.47 (m, 2H), 3.24 (bs, 1H), 2.3–2.06 (m, 4H), 1.64–1.45 (m, 6H), 1.04 (d, 3H). ES-MS: calcd. for C$_{18}$H$_{25}$FN$_4$O$_4$ (380.42); found: 381.3 [M+H].

A-8 is prepared from 2-chlorocarbonyl-pyrrolidine-1-carboxylic acid benzyl ester and 6-fluoro-pyridin-2-ylamine as described for the synthesis of pyrrolidine-2-carboxylic acid pyridine-2-yl-amide (hydrobromic acid salt) in Example 1.

(6-fluoro-pyridin-2-yl)-(4-methoxy-benzyl)-amine

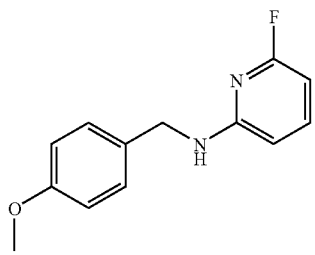

To a solution of 2,6-di-fluoro-pyridine (2.2 g, 1 equiv.) in DMF (20 mL) is added 4-methoxy-benzylamine (5.6 g, 2.2 equiv.) and potassium carbonate (12 g, 4.4 equiv.). After heating at 50° C. for 16 hours, the solution is cooled to rt and filtered through Celite. The filtrate is concentrated under reduced pressure. The residue is purified by silica gel column chromatography using a gradient of hexane:EtOAc (19:1→4:1) to give the title compound.

1H NMR (CDCl$_3$): δ 7.49–7.41 (dd, J=7&8 Hz, 1H), 7.24–7.28 (m, 2H), 6.90–6.85 (m, 2H), 6.19–6.13 (m, 2H), 4.40 (d, J=6 Hz, 2H), 3.80 (s, 3H). ES-MS: calcd. for C$_{13}$H$_{13}$FN$_2$O (232.25); found: 233.4 [M+H].

2-S-(6-fluoro-pyridin-2-yl-carbamoyl)-pyrrolidine-1-carboxylic acid benzyl ester

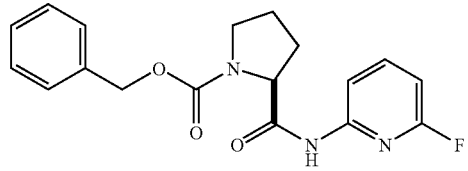

2-chlorocarbonyl-pyrrolidine-1-carboxylic acid benzyl ester and (3-fluoro-phenyl)-(4-methoxy-benzyl)-amine is reacted to give amide intermediate as described for the synthesis of 2-S-(pyridin-2-yl-carbamoyl)-pyrrolidine-1-carboxylic acid benzyl ester in Example 1. This intermediate is treated with 90% aq. TFA to give the title compound.

1H NMR (CDCl$_3$): δ 8.06 (d, J=8.2 Hz, 1H), 7.82–7.74 (dd, J=8 Hz, 1H), 7.38–7.26 (m, 5H), 6.66 (d, J=7.5 Hz, 1H), 5.30–5.18 (m, 3H), 3.60–3.59 (m, 2H), 2.05–1.92 (m, 4H). ES-MS: calcd. for C$_{18}$H$_{18}$FN$_3$O$_3$ (343.35); found: 344.3 [M+H].

Pyrrolidine-2-S-carboxylic acid (6-fluoro-pyridin-2-yl) amide hydrobromic acid salt

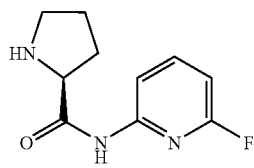

Title compound is prepared from above intermediate as described for the synthesis of pyrrolidine-2-carboxylic acid pyridine-2-yl-amide (hydrobromic acid salt) in Example 1.

1H NMR (DMSO-d$_6$): δ 7.4–7.3 (m, 1H), 6.21–6.17 (m, 1H), 4.88–4.87 (d, 1H), 3.86 (bs, 1H), 2.89–2.69 (m, 2H), 1.99–1.91 (m, 1H), 1.58–1.45 (m, 3H). ES-MS: calcd. for C$_{10}$H$_{12}$FN$_3$O (209.1); found: 242.3 [M+K].

EXAMPLE 10

1-{2-R-[(formyl-hydroxy-amino)-methyl]-hexanoyl}-pyrrolidine-2-S-carboxylic acid-(4,6-di-methyl-1-oxy-pyridin-2-yl)-amide

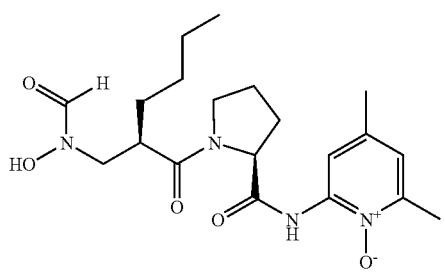

The title compound is prepared according to General Procedure A from 2-[(benzyloxy-formyl-amino)-methyl]- hexanoic acid A-7 (R=n-butyl) and pyrrolidine-2-carboxylic acid (4,6-di-methyl-1-oxy-pyridin-2-yl)-amide A-8 [X=CH$_2$, n=1, R$_1$=2-(4,6-di-methyl-1-oxy)-pyridyl].

1H NMR (DMSO-d$_6$): δ 8.29 (bs, 1H), 7.99 (bs, 1H), 7.24 (bs, 1H), 4.86–4.83 (d, J=7.692 Hz, 1H), 3.82–3.70 (m, 2H), 3.53–3.5 (m, 2H), 3.24 (bs, 1H), 2.57 (bs, 3H), 2.47 (bs, 3H), 2.3–2.12 (m, 4H), 1.97–1.43 (m, 6H), 1.01 (bs, 3H). ES-MS: calcd. for C$_{20}$H$_{30}$N$_4$O$_5$ (406.48); found: 407.3 [M+H].

Pyrrolidine-2-S-carboxylic Acid (4,6-di-methyl-1-oxy-pyridin-2-yl) amide hydrobromic acid salt

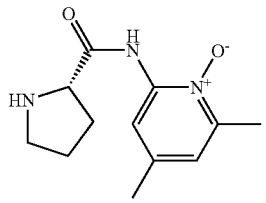

2-chlorocarbonyl-pyrrolidine-1-carboxylic acid benzyl ester and 4,6-di-methyl-pyridin-2-ylamine is reacted to give amide intermediate as described for the synthesis of 2-S-(pyridin-2-yl-carbamoyl)-pyrrolidine-1-carboxylic acid benzyl ester in Example 1. This intermediate on oxidation with MCPBA followed by treatment with HBr—AcOH provides the title compound.

1H NMR (DMSO-d$_6$): δ 8.2–8.19 (d, J=1.92 Hz, 1H), 7.34–7.33 (d, J=1.92 Hz, 1H), 4.98–4.96 (d, J=9.87 Hz, 1H), 3.48–3.46 (d, J=6.49 Hz, 2H), 2.60 (bs, 4H), 2.55 (bs, 3H), 2.2–2.09 (m, 3H). ES-MS: calcd. for C$_{12}$H$_{17}$N$_3$O (235.13); found: 258.3 [M+Na].

EXAMPLE 11

1-{2-R-[(formyl-hydroxy-amino)-methyl]-hexanoyl}-pyrrolidine-2-S-carboxylic acid-(4-methyl-1-oxy-pyridin-2-yl)-amide

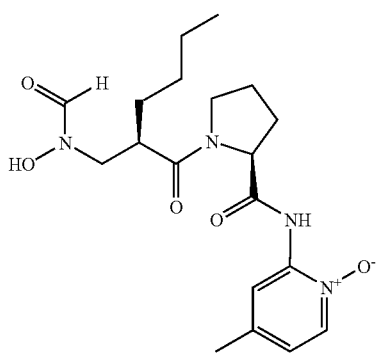

The title compound is prepared according to General Procedure A from 2-[(benzyloxy-formyl-amino)-methyl]-hexanoic acid A-7 (R=n-butyl) and pyrrolidine-2-carboxylic acid (4-methyl-1-oxy-pyridin-2-yl)-amide A-8 [X=CH$_2$, n=1, R$_1$=2-(4-methyl-1-oxy)-pyridyl].

1H NMR (DMSO-d$_6$): δ 8.45–8.42 (d, J=6.32 Hz, 1H), 8.3 (bs, 1H), 7.17–7.15 (d, J=6.7 Hz, 1H), 4.91–4.89 (d, J=7.42 Hz, 1H), 3.87–3.66 (m, 2H), 3.53 (bs, 2H), 3.22 (bs, 1H), 2.5 (bs, 3H), 2.34–2.33 (d, J=4.5 Hz, 2H), 2.13–2.12 (d, J=3.3 Hz, 2H), 1.68–1.45 (m, 6H), 1.02 (bs, 3H). ES-MS: calcd. for C$_{19}$H$_{28}$N$_4$O$_5$ (392.46); found: 393.3 [M+H].

Pyrrolidine-2-S-carboxylic acid (4-methyl-1-oxy-pyridin-2-yl) amide hydrobromic acid salt

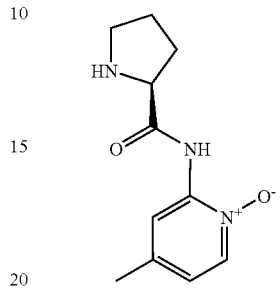

2-chlorocarbonyl-pyrrolidine-1-carboxylic acid benzyl ester and 4-methyl-pyridin-2-ylamine is reacted to give amide intermediate as described for the synthesis of 2-S-(pyridin-2-yl-carbamoyl)-pyrrolidine-1-carboxylic acid benzyl ester in Example 1. This intermediate on oxidation with MCPBA followed by treatment with HBr—AcOH provides the title compound.

1H NMR (DMSO-d$_6$): δ 8.54–8.53 (d, J=6.6 Hz, 1H), 8.32–8.315 (d, J=2.2 Hz, 1H), 7.31–7.28 (m, 1H), 4.98–4.96 (d, J=6.77 Hz, 1H), 3.48–3.46 (d, J=4.39 Hz, 2H), 2.62–2.54 (m, 4H), 2.2–2.07 (m, 3H). ES-MS: calcd. for C$_{11}$H$_{15}$N$_3$O$_2$ (221.12); found: 222.3 [M+H].

EXAMPLE 12

1-{2-R-[(formyl-hydroxy-amino)-methyl]-hexanoyl}-azetidine-2-S-carboxylic acid-pyridin-2-ylamide

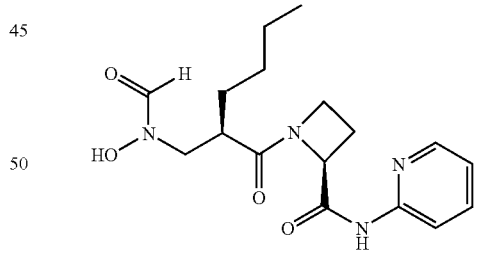

The title compound is prepared according to General Procedure A from 2-[(benzyloxy-formyl-amino)-methyl]-hexanoic acid A-7 (R=n-butyl) and azetidine-2-carboxylic acid (pyridin-2-yl)-amide A-8 [X=CH$_2$, n=1, R$_1$=2-pyridyl].

1H NMR (DMSO-d$_6$): δ 10.74 (bs, 1H), 8.52 (bs, 1H), 8.29 (bs, 1H), 8.01 (bs, 1H), 7.32 (bs, 1H), 5.11 (bs, 1H), 4.35 (bs, 1H), 3.75–3.55 (m, 4H), 2.71–2.44 (m, 2H), 1–46 (bs, 6H), 1.06 (bs, 3H). ES-MS: calcd. for C$_{17}$H$_{24}$N$_4$O$_4$ (348.40); found: 349.3 [M+H].

A-8 is prepared from azetidine-1,2-dicarboxylic acid 1-tert butyl ester and pyridin-2-ylamine as described below.

2-S-(pyridin-2-ylcarbamoyl)-azetidine-1-carboxylic acid tert butyl ester

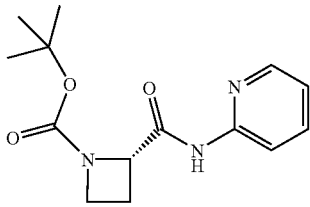

Boc-protected azetidine carboxylic acid is prepared by reacting the free amino acid with Boc-anhydride in the presence of NaHCO$_3$, THF:water (1:1 v/v). The protected amino acid is coupled to 2-amino pyridine using HATU/DIEA/DMF to yield the protected amide.

1H NMR (CDCl$_3$): δ 8.52–8.49 (m, 2H), 8.02–7.96 (m, 1H), 7.32–7.28 (dd, 1H), 5.02–4.97 (t, J=8.42 & 8.24 Hz, 1H), 4.2–4.06 (m, 2H), 2.75–2.7 (t, J=6.04 & 8.24 Hz, 2H), 1.73–1.63 (m, 9H). ES-MS: calcd. for C$_{14}$H$_{19}$N$_3$O$_3$ (277.32); found: 278.5 [M+H].

Azetidine-2-S-carboxylic acid pyridin-2-yl-amide hydrochloric acid salt

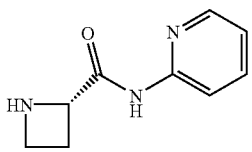

The protected amide is treated with 4.0 M HCl-dioxane to give HCl salt of A-8.

1H NMR (DMSO-d$_6$): δ 8.56–8.54 (dd, 1H), 8.29–8.26 (d, J=7.97 Hz, 1H), 8.10–8.05 (dd, 1H), 7.41–7.37 (dd, 1H), 5.32 (s, 1H), 4.17–3.9 (m, 2H), 2.94–2.85 (m, 2H). ES-MS: calcd. for C$_9$H$_{11}$N$_3$O (177.2); found: 178.4 [M+H].

EXAMPLE 13

1-{2-R-[(formyl-hydroxy-amino)-methyl]-hexanoyl}-pyrrolidine-2-S-carboxylic acid-(4,6-di-methyl-pyridin-2-yl)-amide

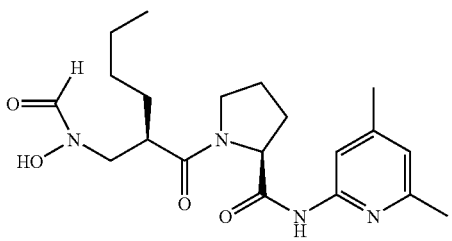

The title compound is prepared according to General Procedure A from 2-[(benzyloxy-formyl-amino)-methyl]-hexanoic acid A-7 (R=n-butyl) and pyrrolidine-2-carboxylic acid (4,6-di-methyl-pyridin-2-yl)-amide A-8 [X=CH$_2$, n=1, R$_1$=2-(5-trifluoromethyl)pyridyl].

1H NMR (DMSO-d$_6$, rotamers): δ 10.5 (s, 1H), 10.3 (s, 0.4H), 9.87 (s, 0.6H), 8.44 (s, 0.5H), 7.97 (s, 0.5H), 7.89 (s, 1H), 6.98 (s, 1H), 4.74–4.72 (m, 1H), 3.84–3.45 (m, 4H), 3.32 (bs, 1H), 2.54 (s, 3H), 2.43 (s, 3H), 2.29–2.05 (m, 4H), 1.64–1.46 (m, 6H), 1.11–0.925 (m, 3H). ES-MS: calcd. for C$_{20}$H$_{30}$N$_4$O$_4$ (390.48); found: 391.4 [M+H].

Pyrrolidine-2-S-carboxylic Acid (4,6-di-methyl-pyridin-2-yl) amide hydrobromic acid salt

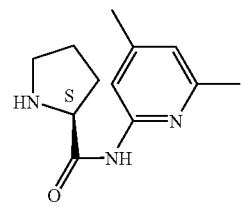

2-chlorocarbonyl-pyrrolidine-1-carboxylic acid benzyl ester and 4,6-di-methyl-pyridin-2-ylamine are reacted to give amide intermediate as described for the synthesis of 2-S-(pyridin-2-yl-carbamoyl)-pyrrolidine-1-carboxylic acid benzyl ester in Example 1. This intermediate on with treatment with HBr-AcOH provides the title compound.

1H NMR (DMSO-d$_6$): δ 11.3 (s, 1H), 10.2 (bs, 1H), 7.87 (s, 1H), 7.17 (s, 1H), 4.61 (s, 1H), 2.60 (s, 3H), 2.58 (bs, 1H), 2.50 (s, 3H), 2.17–2.06 (m, 3H). ES-MS: calcd. for C$_{12}$H$_{17}$N$_3$O*2HBr (219.28); found: 220.5 [M+H] free base.

EXAMPLE 14

Synthesis of 1-{2-R-[(formyl-hydroxy-amino)-methyl]-hexanoyl}-pyrrolidine-2-S-carboxylic acid-(4-ethyl-pyridin-2-yl)-amide

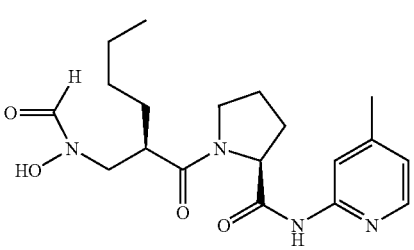

The title compound is prepared according to General Procedure A from 2-[(benzyloxy-formyl-amino)-methyl]-hexanoic acid A-7 (R=n-butyl) and pyrrolidine-2-carboxylic acid (4-ethyl-pyridin-2-yl)-amide A-8 [X=CH$_2$, n=1, R$_1$=2-(4-ethyl)pyridyl].

1H NMR (DMSO-d$_6$, rotamers): δ 10.6 (bs, 1H), 10.23 (s, 0.4H), 9.87 (s, 0.6H), 8.38–8.36 (m, 1H), 8.12 (bs, 1H), 7.99 (bs, 1H), 7.16–7.14 (m, 1H), 4.75 (bs, 1H), 3.75 (bs, 4H), 3.20 (bs, 1H), 2.82–2.75 (q, J=7.56 Hz, 2H), 2.05 (bs, 4H), 1.65–1.45 (m, 6H), 1.38–1.33 (t, J=7.56 Hz, 3H), 1.04 (bs, 3H). ES-MS: calcd. for C$_{20}$H$_{30}$N$_4$O$_4$ (390.48); found: 391.4 [M+H].

A-8 is prepared from 2-chlorocarbonyl-pyrrolidine-1-carboxylic acid benzyl ester and 4-ethyl-pyridin-2-ylamine as described for the synthesis of pyrrolidine-2-carboxylic acid pyridine-2-yl-amide (hydrobromic acid salt) in Example 1.

2-S-(4-ethyl-pyridin-2-ylcarbamoyl)-pyrrolidine-1-carboxylic acid benzyl ester

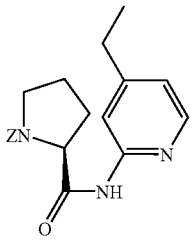

1H NMR (DMSO-d$_6$): δ 10.8–10.7 (d, J=15.1 Hz, 1H), 8.39–8.36 (M, 1H), 8.16 (S, 1H), 7.57–7.25 (m, 5H), 7.18–7.17 (m, 1H), 5.27–5.25 (m, 2H), 4.74–4.68 (m, 1H), 3.68–3.61 (m, 2H), 2.83–2.77 (q, J=6.50 Hz, 2H), 2.43–2.29 (m, 1H), 2.13–1.98 (m, 3H), 1.40–1.35 (t, J=7.55 Hz, 3H). ES-MS: calcd. for C$_{20}$H$_{23}$N$_3$O$_3$ (353.42); found: 354.2 [M+H].

Pyrrolidine-2-S-carboxylic Acid (4-ethyl-pyridin-2-yl)-amide Hydrobromic Acid Salt

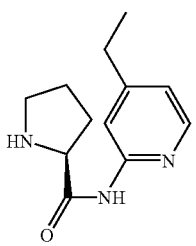

1H NMR (DMSO-d$_6$): δ 11.43 (s, 1H), 8.47–8.45 (m, 1H), 8.24 (bs, 1H), 8.08 (s 1H), 7.33–7.30 (m, 1H), 4.64 (s, 1H), 3.49–3.47 (m, 2H), 2.89–2.82 (q, J=7.51 Hz, 2H), 2.65–2.55 (m, 1H), 2.33–2.07 (m, 3H), 1.40–1.35 (t, J=7.56 Hz, 3H). ES-MS: calcd. for C$_{12}$H$_{17}$N$_3$O*2HBr (219.28); found: 220.3 [M+H] free base.

EXAMPLE 15

1-{2-R-[(formyl-hydroxy-amino)-methyl]-hexanoyl}-pyrrolidine-2-S-carboxylic Acid (3-hydroxy-pyridin-2-yl)-amide

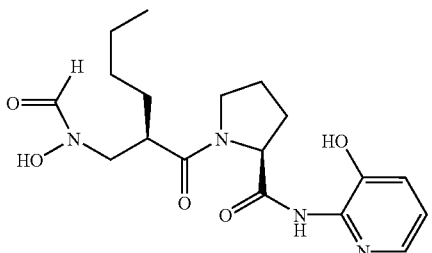

The title compound is prepared according to General Procedure A from 2-[(benzyloxy-formyl-amino)-methyl]-hexanoic acid A-7 (R=n-butyl) and pyrrolidine-2-carboxylic acid (3-benzyloxy-pyridin-2-yl)-amide A-8 [X=CH$_2$, n=1, R$_1$=2-(3-benzyloxy)pyridyl].

1H NMR (DMSO-d$_6$, rotamers): δ 10.94 (bs, 1H), 10.34 (bs, 1H), 9.88 (bs, 1H), 8.10–8.09 (m, 1H), 7.99 (s, 1H), 7.49–7.47 (m, 1H), 7.37–7.33 (m, 1H), 4.85 (bs, 1H), 3.87–3.74 (m, 4H), 3.21 (s, 1H), 2.29 (bs, 1H), 2.19–211 (m, 3H), 1.65–1.44 (m, 6H), 1.03 (bs, 3H). ES-MS: calcd. for C$_{18}$H$_{26}$N$_4$O$_5$ (378.42); found: 379.2 [M+H].

A-8 is prepared from 2-chlorocarbonyl-pyrrolidine-1-carboxylic acid benzyl ester and 3-benzyloxy-pyridin-2-ylamine as described for the synthesis of pyrrolidine-2-carboxylic acid pyridine-2-yl-amide (hydrobromic acid salt) in Example 1.

2-S-(3-benzyloxy-pyridin-2-ylcarbamoyl)-pyrrolidine-1-carboxylic Acid Benzyl Ester

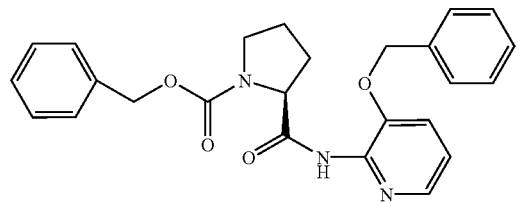

1H NMR (DMSO-d$_6$): δ 10.1–10.0 (d, J=18.1 Hz, 1H), 8.21–8.16 (m, 1H), 7.73–7.40 (m, 12H), 5.32–5.26 (m, 4H), 4.66–4.64 (m, 1H), 3.67–3.54 (m, 2H), 2.38–2.23 (m, 1H), 2.06–1.93 (m, 3H). ES-MS: calcd. for C$_{25}$H$_{25}$N$_3$O$_4$ (431.48); found: 432.3 [M+H].

Pyrrolidine-2-S-carboxylic Acid (3-benzyloxy-pyridin-2-yl)-amide Hydrobromic Acid Salt

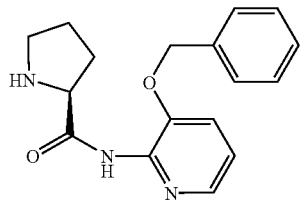

1H NMR (DMSO-d$_6$): δ 10.9 (bs, 1H), 8.88 (s, 1H), 8.24–8.21 (m, 1H), 7.91–7.88 (m, 1H), 7.68–7.51 (m, 6H), 5.42 (s, 2H), 4.71 (bs, 1H), 3.51–3.40 (m, 2H), 2.65–2.47 (m, 1H), 2.19–1.93 (m, 3H). ES-MS: calcd. for C$_{17}$H$_{19}$N$_3$O$_2$.2HBr (297.35); found: 298.3 [M+H] free base.

1-{2-R-[(benzyloxy-formyl-amino)-methyl]-hexanoyl}-pyrrolidine-2-S-carboxylic Acid (3-benzyloxy-pyridin-2-yl)-amide

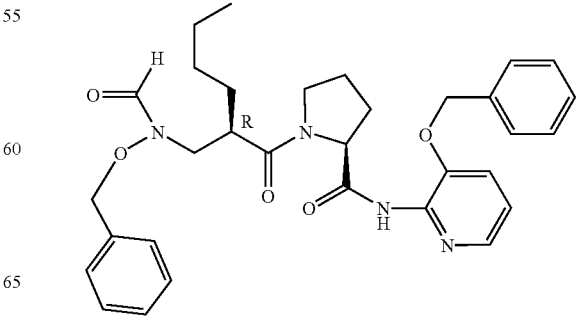

1H NMR (DMSO-d$_6$): δ 9.95 (bs, 1H), 8.42 (bs, 1H), 8.16–8.14 (m, 2H), 7.76–7.39 (m, 1H), 5.33 (bs, 2H), 5.06 (bs, 2H), 3.88–3.85 (m, 2H), 3.65–3.63 (m, 2H), 3.15–3.09 (m, 1H), 2.01–1.89 (m, 4H), 1.49–1.39 (m, 6H), 1.03–0.976 (m, 3H). ES-MS: calcd. for C$_{32}$H$_{38}$N$_4$O$_5$ (558.67); found: 559.3 [M+H].

EXAMPLE 16

1-{2-R-[(formyl-hydroxy-amino)-methyl]-hexanoyl}-pyrrolidine-2-S-carboxyic Acid Isoquinolin-1-ylamide

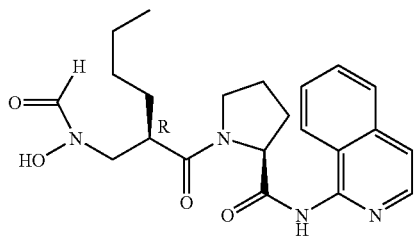

The title compound is prepared according to General Procedure A from 2-[(benzyloxy-formyl-amino)-methyl]-hexanoic acid A-7 (R=n-butyl) and pyrrolidine-2-carboxylic acid (isoquinolin-1-ylamide A-8 [X=CH$_2$, n=1, R$_1$=1-isoquinolinyl].

1H NMR (DMSO-d$_6$, rotamers): δ 10.78 (bs, 1H), 10.26 (s, 0.4H), 9.90 (s, 0.6H), 8.51–9.49 (m, 1H), 8.29–8.26 (m, 1H), 8.17–8.14 (m, 1H), 8.03 (s, 1H), 7.98–7.91 (m, 2H), 7.79–7.74 (m, 1H), 4.82 (bs, 1H), 3.20 (bs, 1H), 2.28–2.12 (m, 4H), 1.53–1.40 (m, 6H), 0.944 (bs, 3H). ES-MS: calcd. for C$_{22}$H$_{28}$N$_4$O$_4$ (412.48); found: 413.4 [M+H].

A-8 is prepared from 2-chlorocarbonyl-pyrrolidine-1-carboxylic acid benzyl ester and 1-amino-isoquinoline as described for the synthesis of pyrrolidine-2-carboxylic acid pyridine-2-yl-amide (hydrobromic acid salt) in Example 1.

Pyrrolidine-2-S-carboxylic Acid isoquinolin-1-yl) Amide Hydrobromic Acid Salt

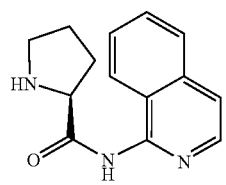

1H NMR (DMSO-d$_6$): δ 8.97 (bs, 1H), 8.72–8.68 (d, J=8.241 Hz, 1H), 8.48–8.46 (d, J=6.044 Hz, 1H), 8.32–8.2 (t, J=8.24 and 8.93 Hz, 1H), 8.18–8.15 (d, J=7.98 Hz, 1H), 8.07–8.0 (m, 1H), 4.92 (bs, 1H), 3.52 (bs, 2H), 2.4–2.31 (m, 1H), 2.23–2.1 (m, 3H). ES-MS: calcd. for C$_{14}$H$_{15}$N$_3$O (241.12); found: 242.3 [M+H].

1-{2-R-[(benzyloxy-formyl-amino)-methyl]-hexanoyl}-pyrrolidine-2-S-carboxylic Acid isoquinolin-1-ylamide

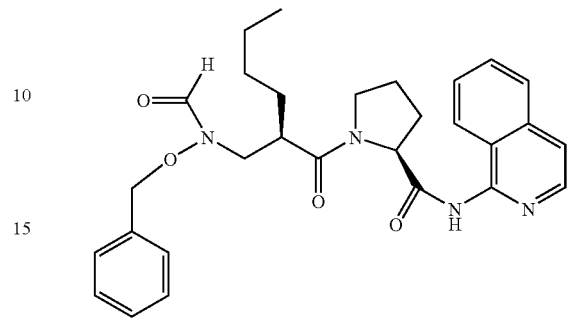

1H NMR (DMSO-d$_6$): δ 10.8 (S, 1H), 8.50 (S, 1H), 8.49 (S, 1H), 8.28–8.25 (m, 1H), 8.16–8.14 (m, 1H), 7.97–7.91 (m, 2H), 7.79–7.74 (m, 1H), 7.63–7.59 (m, 5H), 5.08 (bs, 2H), 4,81 (bs, 1H), 3.90 (bs, 2H), 3.78 (bs, 2H), 3.14 (s, 1H), 2.35–2.26 (m, 2H), 2.19–2.10 (m, 2H), 1.51–1.36 (m, 6H), 0.946–0.901 (t, J=6.87 Hz, 3H). ES-MS: calcd. for C$_{29}$H$_{34}$N$_4$O$_4$ (502.60); found: 503.4 [M+H].

EXAMPLE 17

1-{2-R-[(formyl-hydroxy-amino)-methyl]-hexanoyl}-pyrrolidine-2-S-carboxyic Acid quinolin-3-ylamide

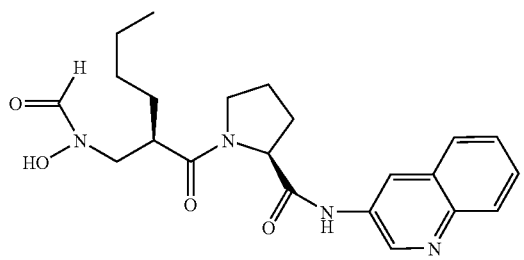

The title compound is prepared according to General Procedure A from 2-[(benzyloxy-formyl-amino)-methyl]-hexanoic acid A-7 (R=n-butyl) and pyrrolidine-2-carboxylic acid quinolin-3-yl-amide A-8 [X=CH$_2$, n=1, R$_1$=3-quinolinyl].

1H NMR (DMSO-d$_6$, rotamers): δ 10.82 (bs, 1H), 10.25 (s, 0.3H), 9.98 (s, 0.7H), 9.34 (s, 1H), 8.61 (s, 1H), 8.26–8.23 (m, 1H), 8.09–8.06 (m, 1H), 7.99 (s, 1H), 7.92–7.87 (m, 1H), 7.74–7.79 (m, 1H), 4.84 (bs, 1H), 3.83–3.72 (m, 4H), 3.24 (s, 1H), 2.25–2.10 (m, 4H), 1.67–1.48 (m, 6H), 1.06 (bs, 3H). ES-MS: calcd. for C$_{22}$H$_{28}$N$_4$O$_4$ (412.48); found: 413.3 [M+H].

A-8 is prepared from 2-chlorocarbonyl-pyrrolidine-1-carboxylic acid benzyl ester and 3-amino-quinoline as described for the synthesis of pyrrolidine-2-carboxylic acid pyridine-2-yl-amide (hydrobromic acid salt) in Example 1.

2-S-(quinolin-3-ylcarbamoyl)-pyrrolidine-1-carboxylic acid benzyl ester

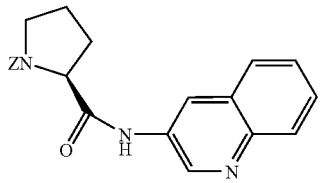

1H NMR (DMSO-d$_6$): δ 11.0–10.9 (d, J=15.9 Hz, 1H), 9.34–9.33 (m, 1H), 8.66–8.65 (m, 1H), 8.27–8.24 (m, 1H), 8.10–8.05 (m, 1H), 7.94–7.88 (m, 1H), 7.77–7.70 (m, 1H), 7.58–7.49 (m, 2H), 7.41–7.39 (m, 1H), 7.29–7.17 (m, 2H), 5.28–5.27 (m, 2H), 4.82–4.74 (m, 1H), 3.76–3.64 (m, 2H), 2.55–2.33 (m, 1H), 2.15–2.01 (m, 3H). ES-MS: calcd. for C$_{22}$H$_{21}$N$_3$O$_3$ (375.42); found: 376.3 [M+H].

Pyrrolidine-2-S-carboxylic acid quinolin-3-yl) Amide Hydrobromic Acid Salt

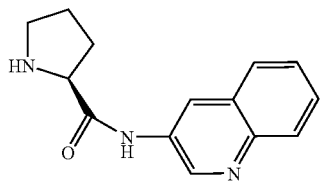

1H NMR (DMSO-d$_6$): δ 11.4 (s, 1H), 9.40 (s, 1H), 8.93–8.92 (bs, 1H), 8.63 (s, 1H), 8.30–8.28 (s, 1H), 8.15–8.12 (s, 1H), 8.01–7.92 (m, 1H), 7.80–7.75 (m, 1H), 4.68–4.66 (m, 1H), 3.53–3.48 (m, 2H), 2.66–2.59 (m, 1H), 2.26–2.09 (m, 3H). ES-MS: calcd. for C$_{14}$H$_{15}$N$_3$O*2HBr (241.29); found: 242.2 [M+H] free base.

1-{2-R-[(benzyloxy-formyl-amino)-methyl]-hexanoyl}-pyrrolidine-2-S-carboxylic Acid quinolin-3-ylamide

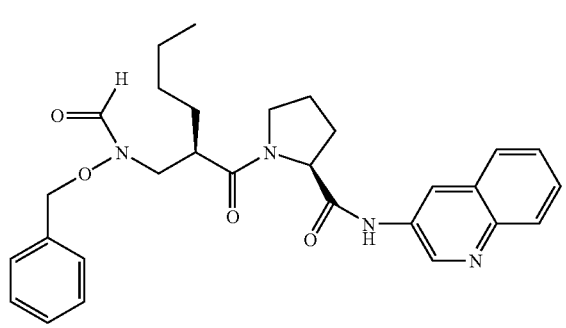

1H NMR (DMSO-d$_6$): δ 10.82 (bs, 1H), 9.33 (bs, 1H), 8.60 (bs, 1H), 8.42 (bs, 1H), 8.25–8.22 (m, 1H), 8.08–8.05 (m, 1H), 7.91–7.86 (m, 1H), 7.73–7.69 (m, 1H), 7.63 (bs, 5H), 5.07 (bs, 2H), 4.84 (bs, 1H), 3.92–3.82 (m, 2H), 3.76–3.67 (m, 2H), 3.14(bs, 1H), 2.33–2.17 (m, 2H), 2.12–2.06 (m, 2H), 1.67–1.45 (m, 6H), 1.04 (m, 3H). ES-MS: calcd. for C$_{29}$H$_{34}$N$_4$O$_4$ (502.60); found: 503.4 [M+H].

EXAMPLE 18

1-{2-R-[(formyl-hydroxy-amino)-methyl]-hexanoyl}-azetidine-2-S-carboxylic Acid-4-methyl-pyridin-2-ylamide

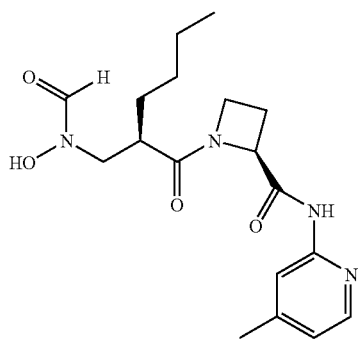

The title compound is prepared according to General Procedure A from 2-[(benzyloxy-formyl-amino)-methyl]-hexanoic acid A-1 (R=n-butyl) and azetidine-2-carboxylic acid (4-methyl-pyridin-2-yl)-amide A-8 [X=CH$_2$, n=1, R$_1$=2-(4-Me-pyridyl)].

1H NMR (DMSO-d$_6$): δ 8.36–8.35 (d, J=4.12 Hz, 1H), 8.14–8.03 (d, J=23 Hz, 1H), 7.16–7.15 (d, J=3.85 Hz, 1H), 5.06 (bs, 1H), 4.39–4.30 (m, 2H), 3.75–3.72 (d, J=7.42 Hz, 1H), 3.53 (bs, 2H), 2.51 (bs, 3H), 2.41 (bs, 2H), 1.44 (bs, 6H), 1.03 (bs, 3H). ES-MS: calcd. for C$_{18}$H$_{26}$N$_4$O$_4$ (362.43); found: 363.3 [M+H].

A-8 is prepared from azetidine-1,2-dicarboxylic acid 1-tert butyl ester and 4-methyl-pyridin-2-ylamine as described below.

Azetidine 2-S-(4-methyl-pyridin-2-ylcarbamoyl)amide

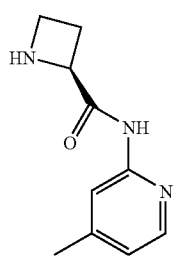

The N-Boc protected amino acid is coupled to 2-amino pyridine using HATU/DIEA/DMF to yield the protected amide. The protected amide is treated with 4.0 M HCl-dioxane to give HCl salt of A-8.

1H NMR (DMSO-d$_6$): δ 8.41 (bs, 1H), 8.17–8.14 (d, J=8.24 Hz, 1H), 7.99–7.96 (d, J=8.24 Hz, 1H), 5.33 (bs, 1H), 4.2–4.12 (m, 1H), 3.99–3.95 (m, 1H), 2.93–2.84 (m, 2H), 2.47 (s, 3H). ES-MS: calcd. for C$_{10}$H$_{13}$N$_3$O (191.11); found: 192.3 [M+H].

EXAMPLE 19

1-{2-R-[(formyl-hydroxy-amino)-methyl]-hexanoyl}-azetidine-2-S-carboxylic Acid-5-methyl-pyridin-2-ylamide

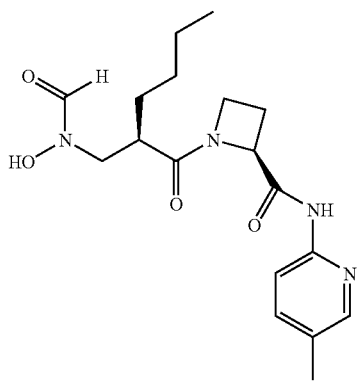

The title compound is prepared according to General Procedure A from 2-[((benzyloxy-formyl-amino)-methyl]-hexanoic acid A-7 (R=n-butyl) and azetidine-2-carboxylic acid (5-methyl-pyridin-2-yl)-amide A-8 [X=CH$_2$, n=1, R$_1$=2-(5-Me-pyridyl)].

1H NMR (DMSO-d$_6$): δ 8.07 (bs, 1H), 7.94–7.91 (d, J=8.24 Hz, 1H), 7.56–7.53 (d, J=8.52 Hz, 1H), 4.79 (bs, 1H), 4.13–4.04 (m, 2H), 3.48 (bs, 1H), 3.37 (bs, 2H), 2.28 (bs, 1H), 2.17 (bs, 4H), 1.18 (bs, 6H), 0.77 (bs, 3H). ES-MS: calcd. for C$_{18}$H$_{26}$N$_4$O$_4$ (362.43); found: 363.3 [M+H].

A-8 is prepared from azetidine-1,2-dicarboxylic acid 1-tert butyl ester and 5-methyl-pyridin-2-ylamine as described below.

Azetidine 2-S-(5-methyl-pyridin-2-ylcarbamoyl)amide

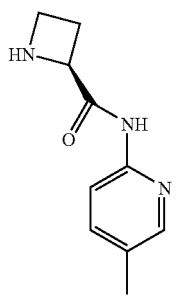

The N-Boc protected amino acid is coupled to 2-amino pyridine using HATU/DIEA/DMF to yield the protected amide. The protected amide is treated with 4.0 M HCl-dioxane to give HCl salt of A-8.

1H NMR (DMSO-d$_6$): δ 8.41 (bs, 1H), 8.17–8.14 (d, J=8.24 Hz, 1H), 7.99–7.96 (d, J=8.24 Hz, 1H), 5.33 (bs, 1H), 4.2–4.12 (m, 1H), 3.99–3.95 (m, 1H), 2.93–2.84 (m, 2H), 2.47 (s, 3H). ES-MS: calcd. for C$_{10}$H$_{13}$N$_3$O (191.11); found: 192.3 [M+H].

EXAMPLE 20

1-{2-R-[(formyl-hydroxy-amino)-methyl]-hexanoyl}-azetidine-2-S-carboxylic Acid-5-fluoro-pyridin-2-ylamide

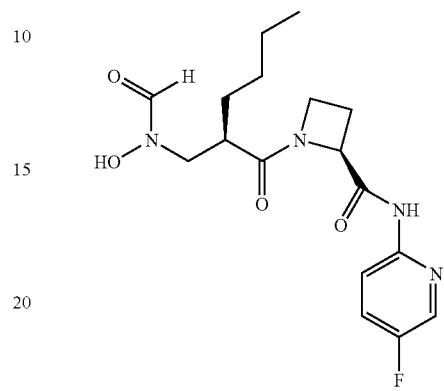

The title compound is prepared according to General Procedure A from 2-[(benzyloxy-formyl-amino)-methyl]-hexanoic acid A-7 (R=n-butyl) and azetidine-2-carboxylic acid (5-fluoro-pyridin-2-yl)-amide A-8 [X=CH$_2$, n=1, R$_1$=2-(5-F-pyridyl)].

1H NMR (DMSO-d$_6$): δ 8.52 (bs, 1H), 8.36–8.33 (t, J=3.3 & 5.2 Hz, 1H), 8.0–7.93 (dd, J=4.95 & 8.52 Hz, 1H), 5.08 (bs, 1H), 4.33 (bs, 2H), 3.74 (bs, 1H), 3.53 (bs, 2H), 2.41 (bs, 2H), 1.42 (bs, 6H), 1.03 (bs, 3H). ES-MS: calcd. for C$_{17}$H$_{23}$FN$_4$O$_4$ (366.69); found: 367.2 [M+H].

A-8 is prepared from azetidine-1,2-dicarboxylic acid 1-tert butyl ester and 5-methyl-pyridin-2-ylamine as described below.

Azetidine 2-S-(5-fluoro-pyridin-2-ylcarbamoyl)amide

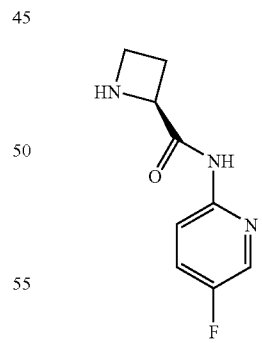

The N-Boc protected amino acid is coupled to 2-amino pyridine using HATU/DIEA/DMF to yield the protected amide. The protected amide is treated with 4.0 M HCl-dioxane to give HCl salt of the free amine.

1H NMR (DMSO-d$_6$): δ 8.58–8.57 (d, J=3.02 Hz, 1H), 8.32 (bs, 1H), 8.06–7.9 (m, 1H), 5.32 (bs, 1H), 4.17–3.98 (m, 2H), 2.93–2.74 (m, 2H). ES-MS: calcd. for C$_9$H$_{10}$FN$_3$O (195.08); found: 196.2 [M+H].

EXAMPLE 21

1-{2-R-[(formyl-hydroxy-amino)-methyl]-hexanoyl}-pyrrolidine-2-S-carboxylic Acid-(5-trifluoromethyl-1-oxy-pyridin-2-yl)-amide

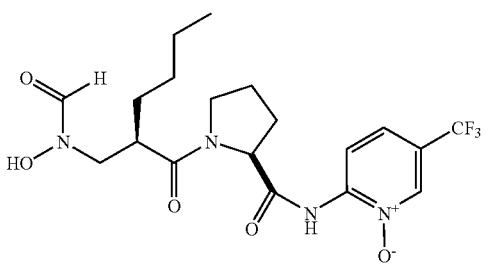

The title compound is prepared according to General Procedure A from 2-[(benzyloxy-formyl-amino)-methyl]-hexanoic acid A-1 (R=n-butyl) and pyrrolidine-2-carboxylic acid (5-trifluoromethyl-1-oxy-pyridin-2-yl)-amide A-8 [X=CH$_2$, n=1, R$_1$=2-(5-trifluoromethyl-1-oxy)-pyridyl].

1H NM R (DMSO-d$_6$): δ 9.15 (bs, 1H), 8.64–8.62 (d, J=8.79 Hz, 1H), 7.98–7.96 (d, J=9.34 Hz, 1H), 5.04–5.0 (m, 1H), 3.87–3.73 (m, 2H), 3.65 (bs, 2H), 3.49–3.48 (m, 1H), 2.34 (bs, 2H), 2.13–2.12 (d, J=2.47 Hz, 2H), 1.67–1.45 (m, 6H), 1.03 (bs, 3H). ES-MS: calcd. for C$_{19}$H$_{25}$F$_3$N$_4$O$_5$ (446.43); found: 447.3 [M+H].

A-8 is prepared from 2-chlorocarbonyl-pyrrolidine-1-carboxylic acid benzyl ester and 3-amino-quinoline as described for the synthesis of pyrrolidine-2-carboxylic acid pyridine-2-yl-amide (hydrobromic acid salt) in Example 1.

2-S-(5-trifluoromethyl-1-oxy-pyridin-2-ylcarbamoyl)-pyrrolidine-1-carboxylic Acid Benzyl Ester

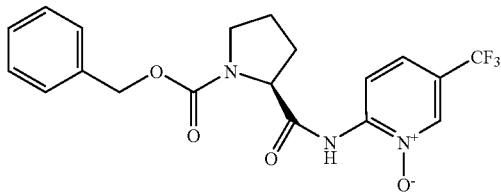

2-chlorocarbonyl-pyrrolidine-1-carboxylic acid benzyl ester and 5-trifluoromethyl-pyridin-2-ylamine is reacted to give amide intermediate as described for the synthesis of 2-S-(pyridin-2-yl-carbamoyl)-pyrrolidine-1-carboxylic acid benzyl ester in Example 1. This intermediate on oxidation with MCPBA provides the title compound.

1H NMR (DMSO-d$_6$): δ 9.15 (bs, 1H), 8.67–8.58 (dd, J=8.79 & 9.07 Hz, 1H), 7.98 (bs, 1H), 7.57 (bs, 2H), 7.37–7.34 (d, J=8.065 Hz, 2H), 5.29–5.26 (d, J=9.9 Hz, 2H), 5.1–5.0 (m, 1H), 3.68–3.53 (m, 2H), 2.63–2.57 (m, 2H), 2.2–2.05 (m, 2H). ES-MS: calcd. for C$_{19}$H$_{18}$F$_3$N$_3$O$_4$ (409.12); found: 410.2 [M+H].

Pyrrolidine-2-S-carboxylic Acid (5-trifluoromethyl-1-oxy-pyridin-2-yl) Amide Hydrobromic Acid Salt

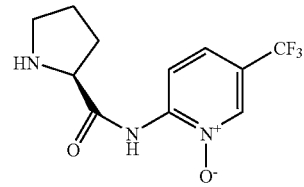

The treatment of the above N-protected intermediate with HBr—AcOH provides the title compound.

1H NMR (DMSO-d$_6$): δ 9.21 (bs, 1H), 8.66–8.63 (d, J=8.79 Hz, 1H), 8.06–8.02 (dd, J=1.37 Hz, 1H), 5.05–5.0 (t, J=6.58 & 7.14 Hz, 1H), 3.58–3.47 (m, 2H), 2.63–2.57 (m, 2H), 2.23–2.1 (m, 2H). ES-MS: calcd. for C$_{11}$H$_{12}$F$_3$N$_3$O$_2$ (275.09); found: 276.1 [M+H].

EXAMPLE 22

1-{2-R-[(formyl-hydroxy-amino)-methyl]-hexanoyl}-pyrrolidine-2-S-arboxylic Acid-(4-ethyl-1-oxy-pyridin-2-yl)-amide

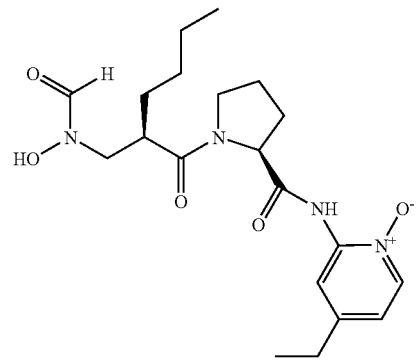

The title compound is prepared according to General Procedure A from 2-[(benzyloxy-formyl-amino)-methyl]-hexanoic acid A-7 (R=n-butyl) and pyrrolidine-2-carboxylic acid (4-ethyl-1-oxy-pyridin-2-yl)-amide A-8 [X=CH$_2$, n=1, R$_1$=2-(4-ethyl-1-oxy)-pyridyl].

1H NMR (DMSO-d$_6$): δ 8.47–8.45 (d, J=6.593 Hz, 1H), 8.35–8.34 (d, J=2.2 Hz, 1H), 7.22–7.20 (m, 1H), 4.92–4.89 (t, J=4.7 & 3.02 Hz, 1H), 3.85–3.80 (t, J=6.49 & 8.24 Hz, 2H), 3.53 (bs, 2H), 3.22 (bs, 1H), 2.85–2.71 (m, 2H), 2.35–2.13 (m, 4H), 1.68–1.36 (m, 6H), 1.02 (bs, 3H). ES-MS: calcd. for C$_{20}$H$_{30}$N$_4$O$_5$ (406.48); found: 407.3 [M+H].

2-S-(4-ethyl-1-oxy-pyridin-2-ylcarbamoyl)-pyrrolidine-1-carboxylic Acid Benzyl Ester

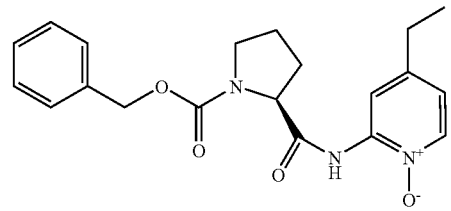

2-chlorocarbonyl-pyrrolidine-1-carboxylic acid benzyl ester and 4-ethyl-pyridin-2-ylamine is reacted to give amide intermediate as described for the synthesis of 2-S-(pyridin-2-yl-carbamoyl)-pyrrolidine-1-carboxylic acid benzyl ester in Example 1. This intermediate on oxidation with MCPBA provides the title compound.

1H NMR (CDCl₃): δ 8.8–8.12 (m, 1H), 7.4–7.2 (m, 1H), 6.85–6.83 (d, J=6.59 Hz, 1H), 5.3–5.1 (m, 2H), 4.57 (bs, 1H), 3.71–3.54 (m, 2H), 2.7–2.63 (dd, J=7.42 Hz, 2H), 2.24–1.73 (m, 4H), 1.3–1.2 (m, 3H). ES-MS: calcd. for C₂₀H₂₃N₃O₄ (369.17); found: 370.2 [M+H].

Pyrrolidine-2-S-carboxylic Acid (4-ethyl-1-oxy-pyridin-2-yl) Amide Hydrobromic Acid Salt

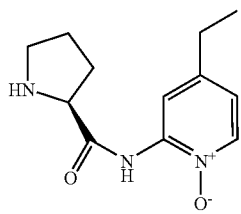

The treatment of the above N-protected intermediate with HBr—AcOH provides the title compound.

1H NMR (DMSO-d₆): δ 8.56–8.53 (d, J=6.6 Hz, 1H), 8.36–8.35 (d, J=2.3 Hz, 1H), 7.33–7.3 (dd, J=2.37 & 2.47 Hz, 1H), 5.0–4.96 (t, J=8.24 & 5.49 Hz, 1H), 3.39–3.42 (m, 2H), 2.88–2.81 (dd, J=7.7 Hz, 2H), 2.64–2.55 (m, 1H), 2.2–2.05 (m, 3H), 1.29–1.25 (t, J=7.14 & 6.87 Hz, 3H). ES-MS: calcd. for C₁₂H₁₇N₃O₂ (235.13); found: 236.2 [M+H].

EXAMPLE 23

1-{2-R-[(formyl-hydroxy-amino)-methyl]-hexanoyl}-pyrrolidine-2-S-carboxylic Acid-(4-phenyl-pyridin-2-yl)-amide

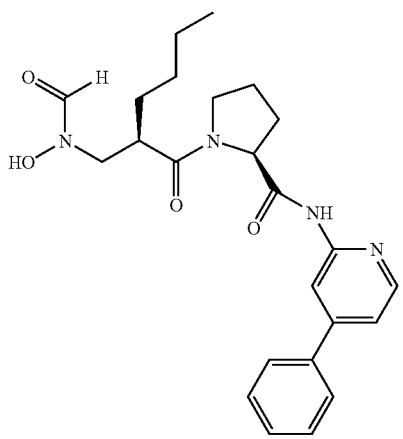

The title compound is prepared according to General Procedure A from 2-[(benzyloxy-formyl-amino)-methyl]-hexanoic acid A-7 (R=n-butyl) and pyrrolidine-2-carboxylic acid (4-phenyl-pyridin-2-yl)-amide A-8 [X CH₂, n=1, R₁=2-(4-phenyl)pyridyl].

1H NMR (DMSO-d₆): δ 8.6–8.45 (m, 1H), 8.3–7.6 (m, 5H), 4.8 (bs, 1H), 3.85–3.71 (m, 2H), 3.31 (bs, 1H), 2.32–1.98 (m, 4H), 1.76–1.43 (m, 6H), 1.04 (bs, 3H). ES-MS: calcd. for C₂₄H₃₀N₄O₄ (438.53); found: 439.4 [M+H].

A-8 is prepared from 2-chlorocarbonyl-pyrrolidine-1-carboxylic acid benzyl ester and 4-phenyl-pyridin-2-ylamine as described for the synthesis of pyrrolidine-2-carboxylic acid pyridine-2-yl-amide (hydrobromic acid salt) in Example 1.

2-S-(4-phenyl-pyridin-2-yl-carbamoyl)-pyrrolidine-1-carboxylic Acid Benzyl Ester

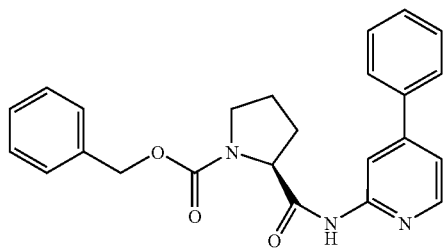

1H NMR (CDCl₃): δ 8.8–8.12 (m, 1H), 7.4–7.2 (m, 1H), 6.85–6.83 (d, J=6.59 H), 5.3–5.1 (m, 2H), 4.57 (bs, 1H), 3.71–3.54 (m, 2H), 2.7–2.63 (dd, J=7.42 Hz, 2H), 2.24–1.73 (m, 4H), 1.3–1.2 (m, 3H). ES-MS: calcd. for C₂₀H₂₃N₃O₄ (369.17); found: 370.2 [M+H].

Pyrrolidine-2-S-carboxylic acid (4-phenyl-pyridin-2-yl) Amide Hydrobromic Acid Salt

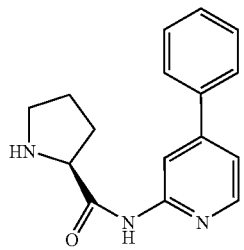

1H NMR (DMSO-d₈): δ 8.64–8.63 (d, J=5.22 Hz, 1H), 8.53 (s, 1H), 7.94–7.91 (dd, J=1.65 & 1.1 Hz, 1H), 7.78–7.67 (m, 5H), 4.68 (bs, 1H), 3.5–3.46 (m, 2H), 2.65–2.58 (m, 1H), 2.24–2.09 (m, 3H). ES-MS: calcd. for C₁₆H₁₇N₃O (267.14); found: 268.3 [M+H].

EXAMPLE 24

1-{2-R-[(formyl-hydroxy-amino)-methyl]-hexanoyl}-pyrrolidine-2-S-carboxylic acid-(4-phenyl-1-oxy-pyridin-2-yl)-amide

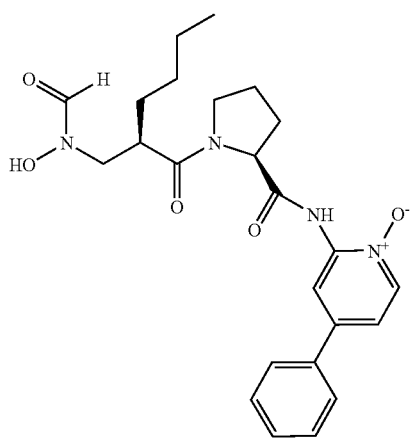

The title compound is prepared according to General Procedure A from 2-[(benzyloxy-formyl-amino)-methyl]-hexanoic acid A-7 (R=n-butyl) and pyrrolidine-2-carboxylic acid (4-phenyl-1-oxy-pyridin-2-yl)-amide A-8 [X=CH₂, n=1, R₁=2-(4-phenyl-1-oxy)-pyridyl].

1H NMR (DMSO-d₆): δ 8.78–8.79 (d, J=2.47 Hz, 1H), 8.64–8.62 (d, J=6.87 Hz, 1H), 7.9–7.6 (m, 5H), 4.99–4.96 (t, J=4.67 & 3.3 Hz, 1H), 3.88–3.76 (m, 1H), 3.53 (bs, 2H), 3.24 (bs, 1H), 2.35–2.15 (m, 4H), 1.68–1.45 (m, 6H), 1.05–1.03 (d, J=6.59 Hz, 3H). ES-MS: calcd. for C₂₄H₃₀N₄O₅ (454.53); found: 455.3 [M+H].

2-S-(4-phenyl-1-oxy-pyridin-2-ylcarbamoyl)-pyrrolidine-1-carboxylic Acid Benzyl Ester

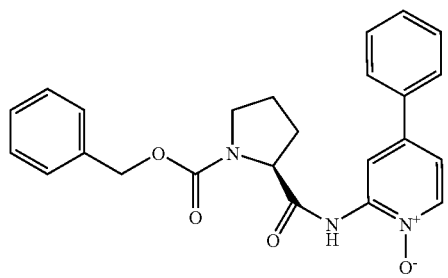

2-chlorocarbonyl-pyrrolidine-1-carboxylic acid benzyl ester and 4-phenyl-pyridin-2-ylamine is reacted to give amide intermediate as described for the synthesis of 2-S-(pyridin-2-yl-carbamoyl)-pyrrolidine-1-carboxylic acid benzyl ester in Example 1. This intermediate on oxidation with MCPBA provides the title compound.

1H NMR (CDCl₃): δ 8.3–8.2 (m, 1H), 7.96–7.13 (m, 12H), 5.73–5.12 (m, 2H), 4.7–4.4 (m, 1H), 3.8–3.5 (m, 2H), 2.5–2.01 (m, 4H). ES-MS: calcd. for C₂₄H₂₃N₃O₄ (417.17); found: 418.1 [M+H].

Pyrrolidine-2-S-carboxylic acid (4-phenyl-1-oxy-pyridin-2-yl) Amide Hydrobromic Acid Salt

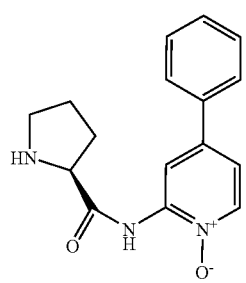

The treatment of the above N-protected intermediate with HBr—AcOH provides the title compound.

1H NMR (DMSO-d₆): δ 8.79–8.78 (d, J=2.47 Hz, 1H), 8.7–8.67 (d, J=6.87 Hz, 1H), 7.94–7.89 (m, 1H), 7.79–7.64 (m, 5H), 5.03–4.97 (dd, J=6.59 Hz, 1H), 3.53–3.44 (m, 2H), 2.64–2.55 (m, 1H), 2.28–2.09 (m, 3H). ES-MS: calcd. for C₁₆H₁₇N₃O₂ (283.13); found: 284.2 [M+H].

EXAMPLE 25

1-{2-R-[(formyl-hydroxy-amino)-methyl]-hexanoyl}-pyrrolidine-2-S-carboxylic Acid-(4-trifluoromethyl-pyridin-2-yl)-amide

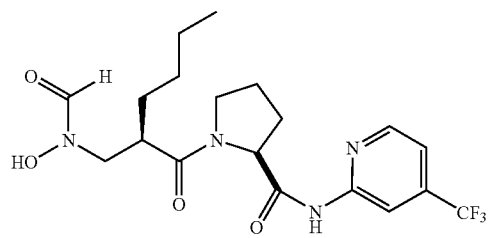

The title compound is prepared according to General Procedure A from 2-[(benzyloxy-formyl-amino)-methyl]-hexanoic acid A-7 (R=n-butyl) and pyrrolidine-2-carboxylic acid (4-trifluoromethyl-pyridin-2-yl)-amide A-8 [X=CH₂, n=1, R₁=2-(4-trifluoromethyl)pyridyl].

1H NMR (DMSO-d₆): δ 8.8–8.78 (d, J=5.22 Hz, 1H), 7.97 (bs, 1H), 7.66–7.65 (d, J=4.67 Hz, 1H), 4.8–4.77 (t, J=4.12 & 4.4 Hz, 1H), 3.86–3.7 (m, 2H), 3.52 (bs, 2H), 3.2 (bs, 1H), 2.33–2.1 (m, 4H), 1.64–1.45 (m, 6H), 1.06–1.04 (d, J=6.32 Hz, 3H). ES-MS: calcd. for C₁₉H₂₅F₃N₄O₄ (430.43); found: 431.3 [M+H].

A-8 is prepared from 2-chlorocarbonyl-pyrrolidine-1-carboxylic acid benzyl ester and 4-trifluoromethyl-pyridin-2-ylamine as described for the synthesis of pyrrolidine-2-carboxylic acid pyridine-2-yl-amide (hydrobromic acid salt) in Example 1.

Pyrrolidine-2-S-carboxylic acid (4-trifluoromethyl-pyridin-2-yl) Amide Hydrobromic Acid Salt

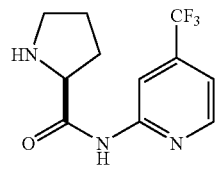

1H NMR (DMSO-d₆): δ 8.93–8.85 (m, 2H), 7.77–7.75 (m, 1H), 4.67–4.65 (d, J=6.593 Hz, 1H), 3.49–3.44 (m, 2H), 2.65–2.56 (m, 1H), 2.24–2.09 (m, 3H). ES-MS: calcd. for C₁₁H₁₂F₃N₃O (259.1); found: 260.2 [M+H].

EXAMPLE 26

1-2{-R-[(formyl-hydroxy-amino)-methyl]-hexanoyl}-pyrrolidine-2-S-carboxylic Acid-(4-trifluoromethyl-1-oxy-pyridin-2-yl)-amide

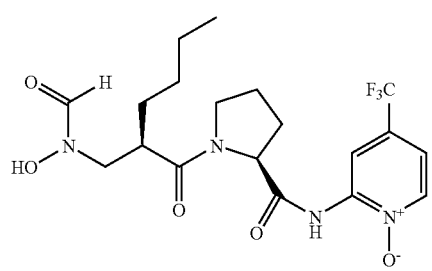

The title compound is prepared according to General Procedure A from 2-[(benzyloxy-formyl-amino)-methyl]-hexanoic acid A-7 (R=n-butyl) and pyrrolidine-2-carboxylic acid (4-trifluoromethyl-1-oxy-pyridin-2-yl)-amide A-8 [X=CH$_2$, n=1, R$_1$=2-(4-trifluoromethyl-1-oxy)-pyridyl].

1H NMR (DMSO-d$_6$): 8.79–8.76 (m, 1H), 7.98 (bs, 1H), 7.73–7.65 (m, 1H), 5.04–5.0 (m, 1H), 3.84–3.72 (m, 2H), 3.52 (bs, 2H), 3.3 (bs, 1H), 2.32–2.13 (m, 2H), 1.77–1.44 (m, 6H), 1.04–1.02 (d, J=6.04 Hz, 3H). ES-MS: calcd. for C$_{19}$H$_{25}$F$_3$N$_4$O$_5$ (446.43); found: 447.3 [M+H].

Pyrrolidine-2-S-carboxylic acid (4-trifluoromethyl-1-oxy-pyridin-2-yl) Amide Hydrobromic Acid Salt

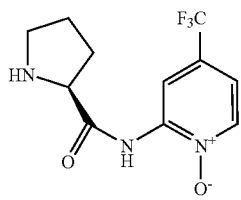

2-chlorocarbonyl-pyrrolidine-1-carboxylic acid benzyl ester and 4-trifluoromethyl-pyridin-2-ylamine is reacted to give amide intermediate as described for the synthesis of 2-S-(pyridin-2-yl-carbamoyl)-pyrrolidine-1-carboxylic acid benzyl ester in Example 1. This intermediate on oxidation with MCPBA followed by the removal of N-benzyloxycarbonyl group with HBr—AcOH provides the title compound.

1H NMR (DMSO-d$_6$): δ 8.94–8.74 (m, 2H), 7.83–7.8 (m, 1H), 5.02–4.97 (t, J=6.22 & 8.52 Hz, 1H), 3.5–3.42 (m, 2H), 2.61–2.52 (m, 1H), 2.27–2.06 (m, 3H). ES-MS: calcd. for C$_{11}$H$_{12}$F$_3$N$_3$O$_2$ (275.09); found: 276.1 [M+H].

EXAMPLE 27

1-{2-R-[(formyl-hydroxy-amino)-methyl]-hexanoyl}-pyrrolidine-2-S-carboxylic Acid-(8-hydroxy-quinolin-2-yl)-amide

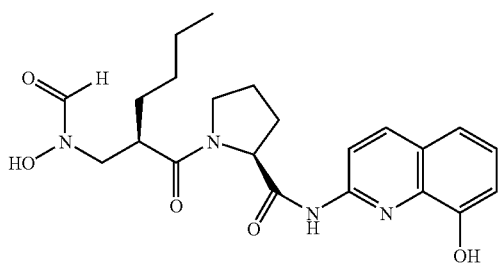

The title compound is prepared according to General Procedure A from 2-[(benzyloxy-formyl-amino)-methyl]-hexanoic acid A-7 (R=n-butyl) and pyrrolidine-2-carboxylic acid (8-benzyloxy-quinolin-2-yl)-amide A-8 [X=CH$_2$, n=1, R$_1$=2-(8-benzyloxy)quinolinyl].

1H NMR (DMSO-d$_6$): δ 8.5–8.35 (m, 2H), 7.98 (bs, 1H), 7.55–7.46 (m, 1H), 7.28–7.26 (m, 1H), 4.83–4.82 (d, J=4.4 Hz, 1H), 3.86–3.68 (m, 4H), 3.27 (bs, 1H), 2.38–2.06 (m, 4H), 1.68–1.42 (bs, 6H), 1.06–1.04 (d, J=6.32 Hz, 3H). ES-MS: calcd. for C$_{22}$H$_{28}$N$_4$O$_5$ (428.48); found: 429.3 [M+H].

2-S-(8-benzyloxy-quinolin-2-ylcarbamoyl)-pyrrolidine-1-carboxylic Acid Benzyl Ester

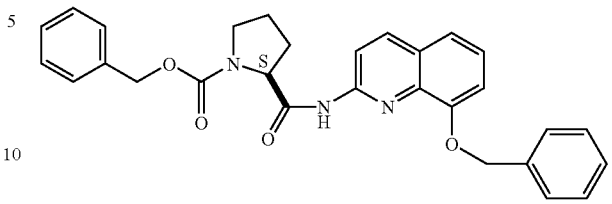

2-chlorocarbonyl-pyrrolidine-1-carboxylic acid benzyl ester and 8-hydroxy-quinolin-2-ylamine is reacted to give bis-proline intermediate as described for the synthesis of 2-S-(pyridin-2-yl-carbamoyl)-pyrrolidine-1-carboxylic acid benzyl ester in Example 1. This intermediate on treatment with lithium hydroxide in THF:water (4:1) provides the corresponding 8-hydroxy derivative which on O-benzylation with benzyl bromide in DMF-K$_2$CO$_3$ yields the desired compound.

1H NMR (DMSO-d$_6$): δ 11.2–11.1 (m, 1H), 8.49 (s, 1H), 7.73–7.23 (m, 14H), 5.50 (s, 2H), 5.31–5.22 (m, 2H), 4.83 (bs, 1H), 3.73–3.61 (m, 2H), 2.52–2.36 (m, 1H), 2.18–2.03 (m, 3H). ES-MS: calcd. for C$_{29}$H$_{27}$N$_3$O$_4$ (481.54); found: 482.2 [M+H].

Pyrrolidine-2-S-carboxylic Acid (8-benzyloxy-quinolin-2-yl)-amide Hydrobromic Acid Salt

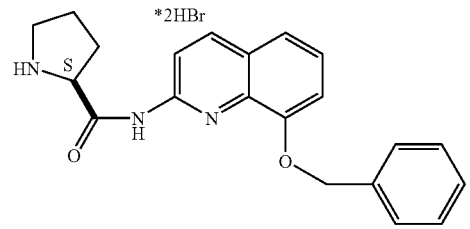

1H NMR (DMSO-d$_6$): δ 11.6 (bs, 1H), 8.91 (bs, 1H), 8.60–8.57 (m, 1H), 7.73–7.31 (m, 9H), 5.52 (s, 2H), 4.68 (bs, 1H), 3.55–3.46 (m, 2H), 2.68–2.63 (m, 1H), 2.18–2.09 (m, 3H). ES-MS: calcd. for C$_{21}$H$_{21}$N$_3$O$_2$.2HBr (347.41); found: 348.3 [M+H].

EXAMPLE 28

1-{2-R-[(formyl-hydroxy-amino)-methyl]-hexanoyl}-pyrrolidine-2-S-carboxylic Acid-(3-methoxy-6-methyl-pyridin-2-yl)-amide

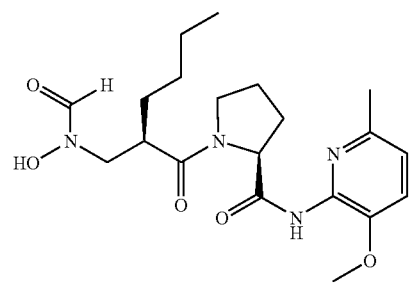

The title compound is prepared according to General Procedure A from 2-[(benzyloxy-formyl-amino)-methyl]- hexanoic acid A-7 (R=n-butyl) and pyrrolidine-2-carboxylic acid (3-methoxy-6-methyl-pyridin-2-yl)-amide A-8 [X=CH$_2$, n=1, R$_1$=2-(3-methoxy-6-methyl)pyridyl].

1H NMR (DMSO-d$_6$): δ 7.54–7.51 (d, J=8.24 Hz, 1H), 7.24–7.21 (d, J=8.24 Hz, 1H), 4.79 (bs, 1H), 3.94 (bs, 3H), 3.86–3.52 (m, 2H), 3.51 (bs, 2H), 3.27 (bs, 1H), 2.69 (bs, 3H), 2.26–2.01 (m, 4H), 1.64–1.42 (bs, 6H), 1.04–1.0 (t, J=5.77 & 6.04 Hz, 3H). ES-MS: calcd. for C$_{20}$H$_{30}$N$_4$O$_5$ (406.48); found: 407.3 [M+H].

A-8 is prepared from 2-chlorocarbonyl-pyrrolidine-1-carboxylic acid benzyl ester and 3-methoxy-6-methyl-pyridin-2-ylamine as described for the synthesis of pyrrolidine-2-carboxylic acid pyridine-2-yl-amide (hydrobromic acid salt) in Example 1.

Pyrrolidine-2-S-carboxylic Acid (3-methoxy-6-methyl-pyridin-2-yl) Amide Hydrobromic Acid Salt

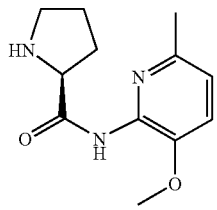

1H NMR (DMSO-d$_6$): δ 7.79–7.76 (d, J=8.24 Hz, 1H), 7.45–7.42 (d, J=8.24 Hz, 1H), 4.68 (bs, 1H), 4.01 (bs, 3H), 3.47–3.43 (t, J=5.49 Hz, 2H), 2.7 (bs, 3H), 2.2–2.08 (m, 4H). ES-MS: calcd. for C$_{12}$H$_{17}$N$_3$O$_2$ (235.13); found: 236.2 [M+H].

EXAMPLE 29

1-{2-R-[(formyl-hydroxy-amino)-methyl]-hexanoyl}-pyrrolidine-2-S-carboxylic Acid (4-methoxy-pyridin-2-yl)-amide

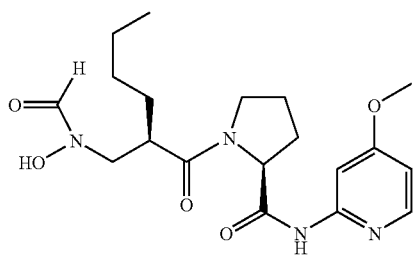

The title compound is prepared according to General Procedure A from 2-[(benzyloxy-formyl-amino)-methyl]-hexanoic acid A-7 (R=n-butyl) and pyrrolidine-2-carboxylic acid (4-methoxy-pyridin-2-yl)-amide A-8 [X=CH$_2$, n=1, R$_1$=2-(4-methoxy)pyridyl].

1H NMR (DMSO-d$_6$, rotamers): δ 10.7 (bs, 1H), 10.2 (s, 0.3H), 9.87 (s, 0.7H), 8.44 (s, 0.6H), 8.32–8.30 (d, J=5.77 Hz, 1H), 7.98 (s, 0.4H), 7.86 (s, 1H), 6.91–6.88 (m, 1H), 4.75–4.73 (m, 1H), 3.99 (s, 3H), 3.87–3.67 (m, 4H), 3.30–3.10 (bs, 1H), 2.30–2.06 (m, 4H), 1.65–1.36 (m, 6H), 1.11–0.926 (m, 3H). ES-MS: calcd. for C$_{19}$H$_{28}$N$_4$O$_5$ (392.45); found: 393.3 [M+H].

A-8 is prepared from 2-chlorocarbonyl-pyrrolidine-1-carboxylic acid benzyl ester and 4-methoxy-pyridin-2-ylamine as described for the synthesis of pyrrolidine-2-carboxylic acid pyridine-2-yl-amide (hydrobromic acid salt) in Example 1.

2-S-(4-methoxy-pyridin-2-ylcarbamoyl)-pyrrolidine-1-carboxylic Acid Benzyl Ester

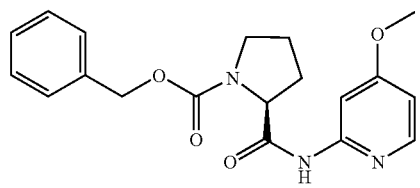

1H NMR (DMSO-d$_6$): δ 10.8–10.7 (d, J=15.9 Hz, 1H), 8.32–8.31 (d, J=5.7 Hz, 1H), 7.91 (s, 1H), 7.58–7.27 (m, 5H), 6.92–6.89 (m, 1H), 5.32–5.16 (m, 2H), 4.75–4.68 (m, 1H), 4.00 (s, 3H), 3.76–3.53 (m, 2H), 2.44–1.98 (m, 4H). ES-MS: calcd. for C$_{19}$H$_{21}$N$_3$O$_4$ (355.39); found: 356.3 [M+H].

Pyrrolidine-2-S-carboxylic Acid (4-methoxy-pyridin-2-yl)-amide Hydrobromic Acid Salt

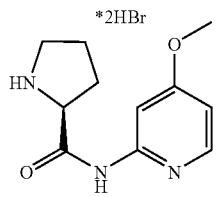

1H NMR (DMSO-d$_6$): δ 11.9 (bs, 1H), 8.98 (bs, 1H), 8.48–8.47 (d, J=6.32 Hz, 1H), 7.67 (bs, 1H), 7.22–7.19 (m, 1H), 4.70–4.69 (m, 1H), 4.12 (s, 3H), 3.51–3.47 (m, 2H), 2.66–2.57 (m, 1H), 2.28–2.10 (m, 3H). ES-MS: calcd. for C$_{11}$H$_{15}$N$_3$O$_2$*2HBr (221.26); found: 222.2 [M+H] free base.

1-{2-R-[(benzyloxy-formyl-amino)-methyl]-hexanoyl}-pyrrolidine-2-S-carboxylic Acid (4-methoxy-pyridin-2-yl)-amide

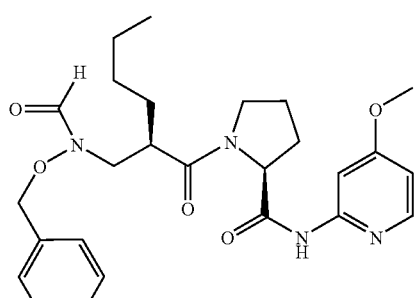

1H NMR (DMSO-d$_6$, rotamers): δ 10.7 (s, 1H), 8.41 (s, 0.5H), 8.33–8.31 (m, 1H), 8.06 (s, 0.5H), 7.85 (s, 1H), 7.62–7.59 (m, 5H), 6.91–6.88 (m, 1H), 5.06 (s, 2H), 4.77 (s, 1H), 3.99 (s, 3H), 3.85–3.67 (m, 4H), 3.10 (bs, 1H), 2.28–2.06 (m, 4H), 1.65–1.44 (m, 6H), 1.05–1.01 (m, 3H). ES-MS: calcd. for C$_{26}$H$_{34}$N$_4$O$_5$ (482.57); found: 483.3 [M+H].

EXAMPLE 30

1-{2-R-[(formyl-hydroxy-amino)-methyl]-hexanoyl}-pyrrolidine-2-S-carboxylic Acid (3-methoxy-pyridin-2-yl)-amide

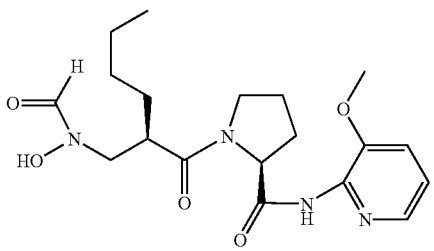

The title compound is prepared according to General Procedure A from 2-[(benzyloxy-formyl-amino)-methyl]-hexanoic acid A-7 (R=n-butyl) and pyrrolidine-2-carboxylic acid (3-methoxy-pyridin-2-yl)-amide A-8 [X CH$_2$, n=1, R$_1$=2-(3-methoxy)pyridyl].

1H NMR (DMSO-d$_6$): δ 9.83 (s, 1H), 8.45 (s, 1H), 8.13–8.11 (m, 1H), 7.98 (s, 1H), 7.65–7.62 (m, 1H), 7.40–7.36 (m, 1H), 4.83 (bs, 1H), 4.00 (s, 3H), 3.70–3.83 (m, 4H), 3.20 (bs, 1H), 2.35–2.205 (m, 4H), 1.75–1.43 (m, 6H), 1.15–1.00 (m, 3H). ES-MS: calcd. for C$_{19}$H$_{28}$N$_4$O$_5$ (392.45); found: 393.3 [M+H].

A-8 is prepared from 2-chlorocarbonyl-pyrrolidine-1-carboxylic acid benzyl ester and 3-methoxy-pyridin-2-ylamine as described for the synthesis of pyrrolidine-2-carboxylic acid pyridine-2-yl-amide (hydrobromic acid salt) in Example 1.

2-S-(3-methoxy-pyridin-2-ylcarbamoyl)-pyrrolidine-1-carboxylic Acid Benzyl Ester

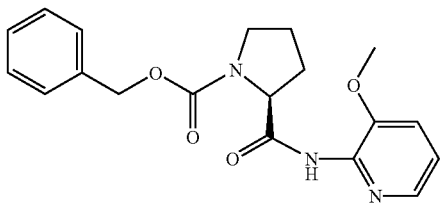

1H NMR (DMSO-d$_6$): δ 9.96–9.90 (d, J=17.8 Hz, 1H), 8.17–8.13 (m, 1H), 7.66–7.39 (m, 7H), 5.28–5.19 (m, 2H), 4.72 (bs, 1H), 3.94 (s, 3H), 3.69–3.53 (m, 2H), 2.49–2.31 (m, 1H), 2.18–2.04 (m, 3H)s. ES-MS: calcd. for C$_{19}$H$_{21}$N$_3$O$_4$ (355.39); found: 356.3 [M+H].

Pyrrolidine-2-S-carboxylic Acid (3-methoxy-pyridin-2-yl)-amide Hydrobromic Acid Salt

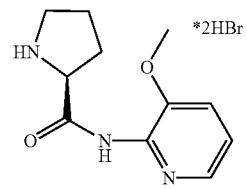

1H NMR (DMSO-d$_6$): δ 10.8 (bs, 1H), 8.89 (bs, 1H), 8.23–8.21 (m, 1H), 7.87–7.85 (m, 1H), 7.60–7.56 (m, 1H), 4.73 (bs, 1H), 4.07 (s, 3H), 3.54–3.45 (m, 2H), 2.64–2.57 (m, 1H), 2.24–2.14 (m, 3H). ES-MS: calcd. for C$_{11}$H$_{15}$N$_3$O$_2$*2HBr (221.26); found: 222.2 [M+H] free base.

1-2{-R-[(benzyloxy-formyl-amino)-methyl]-hexanoyl}-pyrrolidine-2-S-carboxylic Acid (3-methoxy-pyridin-2-yl)-amide

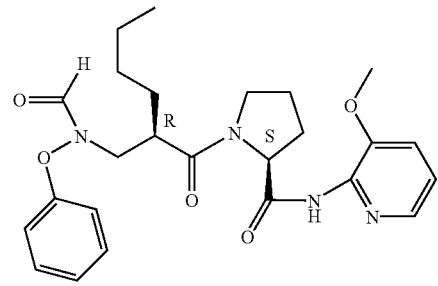

1H NMR (DMSO-d$_6$): δ 9.82 (s, 1H), 8.42 (s, 1H), 8.13–8.11 (m, 1H), 7.65–7.59 (m, 6H), 7.40–7.36 (m, 1H), 5.06 (s, 2H), 4.81 (bs, 1H), 4.00 (s, 3H), 3.88–3.70 (m, 4H), 3.10 (bs, 1H), 2.13–2.01 (m, 4H), 1.65–1.41 (m, 6H), 1.03–0.968 (m, 3H). ES-MS: calcd. for C$_{26}$H N$_4$O$_5$ (482.57); found: 483.3 [M+H].

EXAMPLE 31

1-2{-R-[(formyl-hydroxy-amino)-methyl]-hexanoyl}-pyrrolidine-2-S-carboxylic Acid (6-hydroxy-pyridin-2-yl)-amide

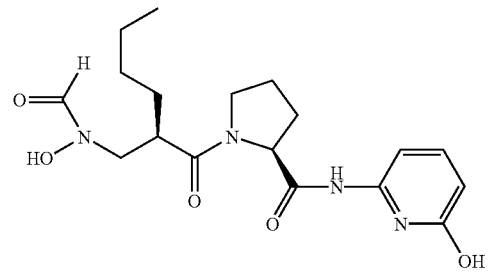

The title compound is prepared according to General Procedure A from 2-[(benzyloxy-formyl-amino)-methyl]-hexanoic acid A-7 (R=n-butyl) and pyrrolidine-2-carboxylic acid (6-benzyloxy-pyridin-2-yl)-amide A-8 [X=CH$_2$, n=1, R$_1$=2-(3-benzyloxy)pyridyl].

1H NMR (DMSO-d$_6$, rotamers): δ 10.4 (bs, 1H), 10.24 (s, 1H), 9.87 (s, 1H), 8.44 (s, 1H), 7.97 (s, 1H), 7.74–7.69 (m, 1H), 6.43 (bs, 1H), 4.70 (bs, 1H), 3.85–3.70 (m, 4H), 3.21 (bs, 1H), 2.27–2.06 (m, 4H), 1.65–1.43 (m, 6H), 1.03 (bs, 3H). ES-MS: calcd. for C$_{18}$H$_{26}$N$_4$O$_5$ (378.42); found: 379.2 [M+H].

A-8 is prepared from 2-chlorocarbonyl-pyrrolidine-1-carboxylic acid benzyl ester and 6-hydroxy-pyridin-2-ylamine to give bis-proline derivative which on basic hydrolysis followed by O-benzylation provides the desired amine as described for the synthesis of pyrrolidine-2-carboxylic acid pyridine-2-yl-amide (hydrobromic acid salt) in Example 1.

2-S-(6-hydroxy-pyridin-2-ylcarbamoyl)-pyrrolidine-1-carboxylic Acid Benzyl Ester

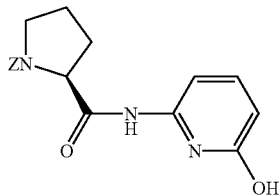

1H NMR (DMSO-d$_6$): δ 10.9 (bs, 1H), 10.5 (bs, 1H), 7.77–7.70 (m, 1H), 7.56–7.30 (m, 6H), 6.48–6.46 (m, 1H), 5.27–5.26 (m, 2H), 4.67–4.62 (m, 1H), 3.72–3.57 (m, 2H), 2.47–1.98 (m, 4H). ES-MS: calcd. for C$_{18}$H$_{19}$N$_3$O$_4$ (341.36); found: 342.3 [M+H].

2-S-(6-benzyloxy-pyridin-2-ylcarbamoyl)-pyrrolidine-1-carboxylic Acid Benzyl Ester

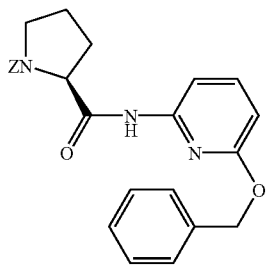

The hydroxy compound (0.920 g, 2.70 mmol, 1 equiv.) is dissolved in DMF (9 mL) and cooled to 0° C. K$_2$CO$_3$ (1.12 g, 8.09 mmol, 3 equiv.) is added followed by benzyl bromide (385 μL, 3.23 mmol, 1.2 equiv.). The resulting mixture is stirred at 0° C. for 1 hour, then at rt for 3 hours. The reaction mixture is diluted with EtOAc, washed with brine, and saturated NaHCO$_3$. The organic layer is dried over anhydrous Na$_2$SO$_4$, filtered and concentrated. Purification by FC (hexane:EtOAc=2:1) gives the title compound as a colorless oil.

1H NMR (DMSO-d$_6$): δ 10.6–10.5 (m, 1H), 7.92–7.86 (m, 1H), 7.69–7.52 (m, 9H), 7.41–7.26 (m, 2H), 6.81–6.75 (m, 1H), 5.54–5.51 (m, 2H), 5.28–5.24 (m, 2H), 4.79–4.68 (m, 1H), 3.69–3.59 (m, 2H), 2.46–2.07 (m, 4H). ES-MS: calcd. for C$_{25}$H$_{25}$N$_3$O$_4$ (431.48); found: 432.3 [M+H].

Pyrrolidine-2-S-carboxylic Acid (6-benzyloxy-pyridin-2-yl)-amide Hydrobromic Acid Salt

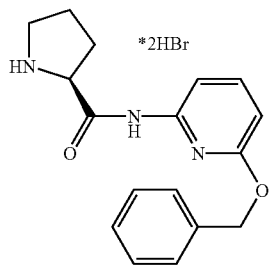

1H NMR (DMSO-d$_6$, rotamers): δ 11.1 (s, 0.6H), 11.0 (s, 0.4H), 8.88 (bs, 1H), 7.99–7.94 (m, 0.4H), 7.86–7.80 (m, 0.6H), 7.67–7.47 (m, 6H), 6.85–6.83 (m, 0.6H), 6.63–6.60 (m, 0.4H), 5.54–5.53 (s, 2H), 4.67–4.62 (m, 1H), 3.51–3.46 (m, 2H), 2.65–2.53 (m, 1H), 2.21–2.03 (m, 3H). ES-MS: calcd. for C$_{17}$H$_{19}$N$_3$O$_2$*2HBr (297.35); found: 298.3 [M+H] free base.

1-{2-R-[(benzyloxy-formyl-amino)-methyl]-hexanoyl}-pyrrolidine-2-S-carboxylic Acid (6-benzyloxy-pyridin-2-yl)-amide

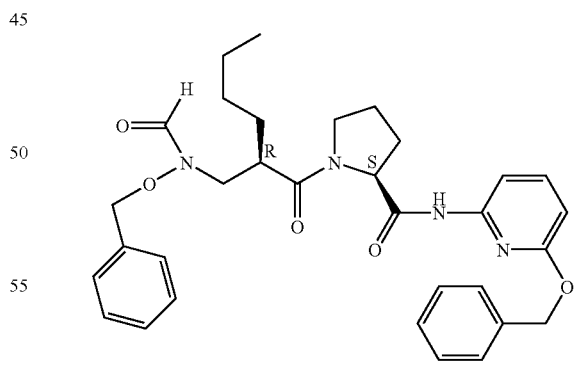

1H NMR (DMSO-d$_6$): δ 10.5 (s, 1H), 8.05 (s, 1H), 7.88–7.80 (m, 2H), 7.64–7.52 (m, 10H), 6.76–6.74 (m, 11H), 5.53 (s, 2H), 5.06 (s, 2H), 4.79 (bs, H), 3.84–3.74 (m, 4H), 3.13 (bs, 1H), 2.22–1.92 (m, 4H), 1.65–1.43 (m, 6H), 1.04–0.976 (m, 3H). ES-MS: calcd. for C$_{32}$H$_{38}$N$_4$O$_5$ (558.67); found: 559.3 [M+H].

EXAMPLE 32

1-{2-R-[(formyl-hydroxy-amino)-methyl]-hexanoyl}-pyrrolidine-2-S-carboxylic Acid (3-hydroxy-1-oxy-pyridin-2-yl)-amide

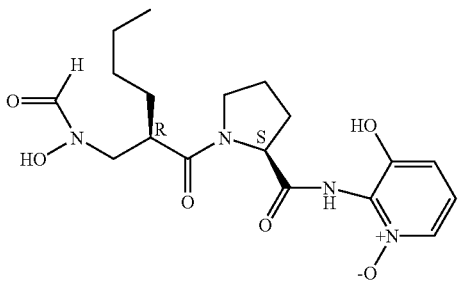

The title compound is prepared according to General Procedure A described below from PFP ester of 2-[(benzyloxy-formyl-amino)-methyl]-hexanoic acid A-7 (R=n-butyl) and pyrrolidine-2-carboxylic acid (3-benzyloxy-1-oxy-pyridin-2-yl)-amide A-8 [X CH$_2$, n=1, R$_1$=2-(3-benzyloxy-1-oxy)-pyridyl].

1H NMR (DMSO-d$_6$): δ 10.2–10.2 (m, 1H), 9.62 (s, 1H), 8.17 (s, 1H), 7.86–7.82 (m, 1H), 7.73 (s, 1H), 7.09–7.03 (m, 1H), 6.85–6.82 (m, 1H), 4.65–4.61 (m, 1H), 3.56–3.45 (m, 4H), 2.96 (bs, 1H), 2.20–1.85 (m, 4H), 1.39–1.17 (m, 6H), 0.753 (bs, 3H). ES-MS: calcd. for C$_{18}$H$_{26}$N$_4$O$_6$ (394.42); found: 395.2 [M+H].

2-S-(3-benzyloxy-1-oxy-pyridin-2-ylcarbamoyl)-pyrrolidine-1-carboxylic Acid Benzyl Ester

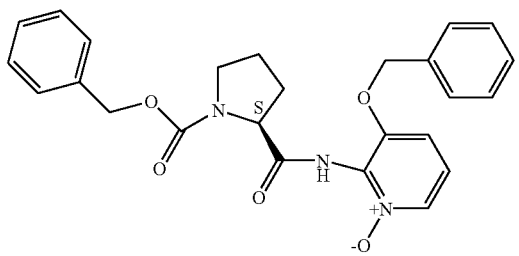

2-chlorocarbonyl-pyrrolidine-1-carboxylic acid benzyl ester and 3-benzyloxy-pyridin-2-ylamine is reacted to give amide intermediate as described for the synthesis of 2-S-(pyridin-2-yl-carbamoyl)-pyrrolidine-1-carboxylic acid benzyl ester in Example 1. This intermediate on oxidation with MCPBA provides the title compound.

1H NMR (DMSO-d$_6$): δ 10.2–10.1 (m, 1H), 8.21–8.16 (m, 1H), 7.65–7.35 (m, 12H), 5.37–5.21 (m, 4H), 4.78–4.70 (m, 1H), 3.63–3.60 (m, 2H), 2.30–1.84 (m, 4H). ES-MS: calcd. for C$_{25}$H$_{25}$N$_3$O$_5$ (447.46); found: 448.2 [M+H].

Pyrrolidine-2-S-carboxylic Acid (3-benzyloxy-1-oxy-pyridin-2-yl)-amide Hydrobromic Acid Salt

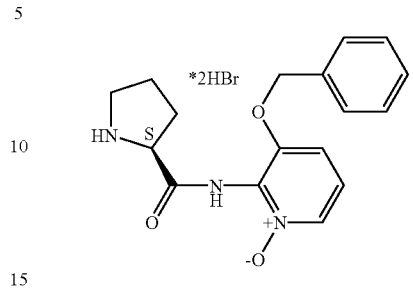

The removal of N-benzyloxycarbonyl group with HBr—AcOH from above intermediate furnished the desired compound.

1H NMR (DMSO-d$_6$): δ 10.8 (s, 1H), 8.90–8.88 (m, 1H), 8.26–8.23 (m, 1H), 7.65–7.45 (m, 7H), 5.39 (s, H), 4.72–4.67 (m, 1H), 3.46–3.34 (m, 2H), 2.54–1.75 (m, 4H). ES-MS: calcd. for C$_{17}$H$_{19}$N$_3$O$_3$*2HBr (313.35); found: 314.3 [M+H] free base.

1-{2-R-[(benzyloxy-formyl-amino)-methyl]-hexanoyl}-pyrrolidine-2-S-carboxylic Acid (3-benzyloxy-1-oxy-pyridin-2-yl)-amide

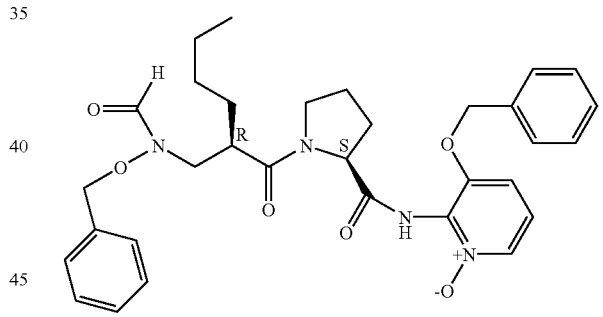

To a solution of pentafluorophenyl ester of A-7 (0.920 g, 2.13 mmol, 1 equiv.) in dry DMF (11 mL) at 0° C. under nitrogen is added Hunig's base (1.9 ml, 10.7 mmol, 5.0 equiv.) followed by amine (1.52 g, 3.20 mmol, 1.5 equiv.). The resulting mixture is stirred at rt for 23 hours. The reaction mixture is partitioned between EtOAc and 10% citric acid. The organic layer is washed with brine and saturated NaHCO$_3$, dried over anhydrous Na$_2$SO$_4$, filtered and concentrated. The residue is purified by FC (CH$_2$Cl$_2$: methanol=100:0 to 96:4) to give the title compound as a white solid.

1H NMR (DMSO-d$_6$): δ 10.08 (s, 1H), 8.19–8.16 (m, H), 7.65–7.36 (m, 13H), 5.3 (s, 2H), 5.06–5.05 (m, 2H), 3.88–3.59 (m, 4H), 3.07 (bs, 1H), 2.10–1.78 (m, 4H), 1.65–1.39 (m, 6H), 1.03–0.945 (m, 3H). ES-MS: calcd. for C$_{32}$H$_{38}$N$_4$O$_6$ (574.67); found: 575.4 [M+H].

EXAMPLE 33

1-{2-R-[(formyl-hydroxy-amino)-methyl]-hexanoyl}-pyrrolidine-2-S-carboxylic Acid (benzo[1,3]dioxol-5-yl)-amide

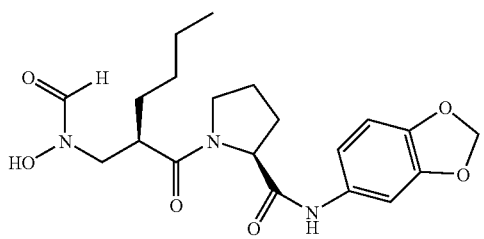

The title compound is prepared according to General Procedure A from 2-[(benzyloxy-formyl-amino)-methyl]-hexanoic acid A-7 (R=n-butyl) and pyrrolidine-2-carboxylic acid (benzo[1,3]dioxol-5-yl)-amide A-8 [X=CH$_2$, n=1, R$_1$=5-(benzo[1,3]dioxol)].

1H NMR (DMSO-d$_6$): δ 7.47–7.46 (d, J=1.65 Hz, 1H), 7.15–7.02 (m, 2H), 6.17–6.16 (d, J=3.85 Hz, 2H), 4.54 (bs, 1H), 3.86–3.7 (m, 2H), 3.52 (bs, 2H), 2.28–2.05 (m, 4H), 1.64–1.45 (m, 6H), 1.06–1.04 (d, J=6.32 Hz, 3H). ES-MS: calcd. for C$_{20}$H$_{27}$N$_3$O$_6$ (405.45); found: 406.3 [M+H].

A-8 is prepared from 2-chlorocarbonyl-pyrrolidine-1-carboxylic acid benzyl ester and 5-amino-(benzo[1,3]dioxol as described for the synthesis of pyrrolidine-2-carboxylic acid pyridine-2-yl-amide (hydrobromic acid salt) in Example 1.

2-S-(benzo[1,3]dioxol-5-yl-carbamoyl)-pyrrolidine-1-carboxylic Acid Benzyl Ester

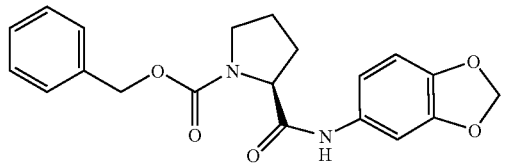

1H NMR (DMSO-d$_6$): δ 7.6–7.3 (m, 6H), 7.2–7.02 (m, 2H), 6.17–6.16 (d, J=1.47 Hz, 2H), 5.31–5.11 (m, 2H), 4.5–4.45 (m, 1H), 3.7–3.6 (m, 2H), 2.5–2.34 (m, 1H), 2.14–1.98 (m, 3H). ES-MS: calcd. for C$_{20}$H$_{20}$N$_2$O$_5$ (368.14); found: 369.2 [M+H].

Pyrrolidine-2-S-carboxylic acid (benzo[1,3]dioxol-5-yl)-amide Hydrobromic Acid Salt

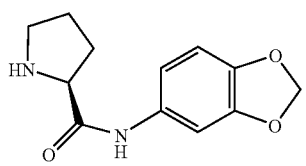

1H NMR (DMSO-d$_6$): δ 7.49–7.48 (d, J=2.2 Hz, 1H), 7.2–7.17 (m, 1H), 7.11–7.08 (d, J=8.24 Hz, 1H), 6.2 (bs, 2H), 4.5–4.48 (t, J=7.1 & 6.3 Hz, 1H), 3.46–3.45 (d, J=5.22 Hz, 2H), 2.58–2.54 (t, J=8.24 & 6.6 Hz, 1H), 2.18–2.1 (m, 3H). ES-MS: calcd. for C$_{12}$H$_{14}$N$_2$O$_3$ (234.1); found: 235.2 [M+H].

EXAMPLE 34

1-{2-R-[(formyl-hydroxy-amino)-methyl]-hexanoyl}-pyrrolidine-2-S-carboxylic acid (2,2-difluoro-benzo[1,3]dioxol-5-yl)-amide

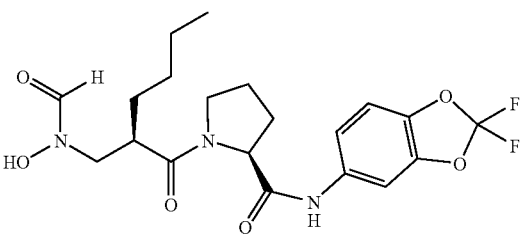

The title compound is prepared according to General Procedure A from 2-[(benzyloxy-formyl-amino)-methyl]-hexanoic acid A-7 (R=n-butyl) and pyrrolidine-2-carboxylic acid (2,2-difluoro-benzo[1,3]dioxol-5-yl)-amide A-8 [X=CH$_2$, n=1, R$_1$=5-((2,2-difluoro-benzo[1,3]dioxol].

1H NMR (DMSO-d$_6$): δ 7.96–7.93 (m, 1H), 7.56–7.42 (m, 2H, 4.56–4.55 (d, J=3.57 Hz, 1H), 3.86–3.6 (m, 2H), 3.53 (bs, 2H), 3.28 (bs, 1H), 2.31–2.02 (m, 4H), 1.63–1.45 (m, 6H), 1.04 (bs, 3H). ES-MS: calcd. for C$_{20}$H$_{25}$F$_2$N$_3$O$_6$ (441.43); found: 442.3 [M+H].

A-8 is prepared from 2-chlorocarbonyl-pyrrolidine-1-carboxylic acid benzyl ester and 5-amino-(2,2-difluoro-benzo[1,3]dioxol) as described for the synthesis of pyrrolidine-2-carboxylic acid pyridine-2-yl-amide (hydrobromic acid salt) in Example 1.

2-S-(2,2-difluoro-benzo[1,3]dioxol-5-yl-carbamoyl)-pyrrolidine-1-carboxylic Acid Benzyl Ester

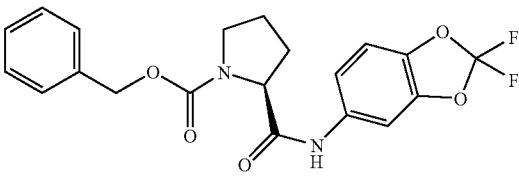

1H NMR (DMSO-d$_6$): δ 7.97–7.87 (dd, 1H), 7.57–7.3 (m, 7H), 5.31–5.10 (m, 2H), 4.6–4.48 (m, 1H), 3.73–3.6 (m, 2H), 2.46–2.38 (m, 1H), 2.15–2.02 (m, 3H). ES-MS: calcd. for C$_{20}$H$_{18}$F$_2$N$_2$O$_5$ (404.12); found: 427.2 [M+Na].

Pyrrolidine-2-S-carboxylic Acid (2,2-difluoro-benzo[1,3]dioxol-5-yl)-amide (Hydrobromic Acid Salt)

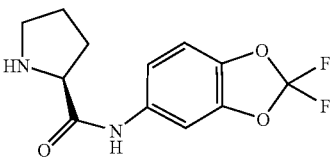

1H NMR (DMSO-d$_6$): δ 7.63–7.33 (m, 3H), 4.56 (bs, 1H), 3.59 (bs, 2H), 2.63–2.56 (m, 1H), 2.2–2.13 (m, 3H). ES-MS: calcd. for C$_{12}$H$_{12}$F$_2$N$_2$O$_3$ (270.08); found: 271.2 [M+H].

EXAMPLE 35

1-{2-R-[(formyl-hydroxy-amino)-methyl]-hexanoyl}-pyrrolidine-2-S-carboxylic Acid (phenoxy-phenyl-3-yl)-amide

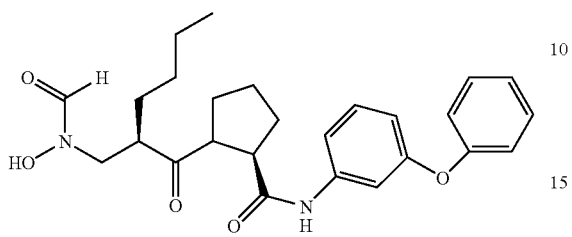

The title compound is prepared according to General Procedure A from 2-[(benzyloxy-formyl-amino)-methyl]-hexanoic acid A-7 (R=n-butyl) and pyrrolidine-2-carboxylic acid 3-phenoxy-phenyl-3-yl)-amide A-8 [X=CH$_2$, n=1, R$_1$=3-(phenoxy-phenyl).

1H NMR (DMSO-d$_6$): δ 7.95 (bs, 1H), 7.60–7.19 (m, 7H), 6.89 (bs, 1H), 4.55 (bs, 1H), 3.8–3.71 (m, 2H), 3.53 (bs, 2H), 3.27 (bs, 1H), 2.27–2.05 (m, 4H), 1.42 (bs, 6H), 1.01 (bs, 3H). ES-MS: calcd. for C$_{25}$H$_{31}$N$_3$O$_5$ (453.54); found: 454.3 [M+H].

A-8 is prepared from 2-chlorocarbonyl-pyrrolidine-1-carboxylic acid benzyl ester and 3-phenoxy-aniline as described for the synthesis of pyrrolidine-2-carboxylic acid pyridine-2-yl-amide (hydrobromic acid salt) in Example 1.

2-S-(phenoxy-phenyl-3-yl-carbamoyl)-pyrrolidine-1-carboxylic Acid Benzyl Ester

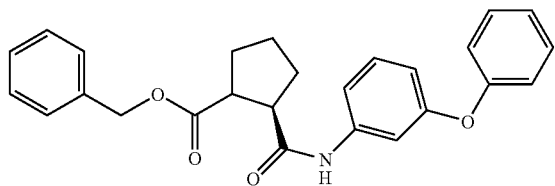

1H NMR (DMSO-d$_6$): δ 7.62–7.19 (m, 13H), 6.95–6.9 (m, 1H), 5.28–5.09 (m, 2H), 4.54–4.46 (m, 1H), 4.2–3.58 (m, 2H), 2.42–2.39 (m, 1H), 2.12–1.99 (m, 3H). ES-MS: calcd. for C$_{25}$H$_{24}$N$_2$O$_4$ (416.17); found: 417.3 [M+H].

Pyrrolidine-2-S-carboxylic Acid (phenoxy-phenyl-3-yl)-amide Hydrobromic Acid Salt

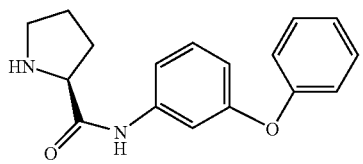

1H NMR (DMSO-d$_6$): δ 7.64–7.21 (m, 8H), 7.01–6.97 (m, $_1$H), 4.51 (bs, 1H), 3.60–3.43 (m, 2H), 2.61–2.52 (m, 1H), 2.16–2.05 (m, 3H). ES-MS: calcd. for C$_{17}$H$_{18}$N$_2$O$_2$ (282.14); found: 283.3 [M+H].

EXAMPLE 36

1-{2-R-[(formyl-hydroxy-amino)-methyl]-hexanoyl}-pyrrolidine-2-S-carboxylic acid (5-fluoro-1-oxy-pyridin-2-yl)-amide

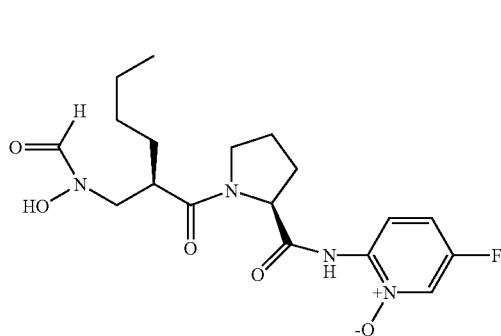

The title compound is prepared according to General Procedure A from 2-[(benzyloxy-formyl-amino)-methyl]-hexanoic acid A-7 (R=n-butyl) and pyrrolidine-2-carboxylic acid (5-fluoro-pyridin-2-yl)-amide A-8 [X=CH$_2$, n=1, R$_1$=2-(5-fluoro)-pyridyl] followed by the oxidation with with MCPBA.

1H NMR (DMSO-d$_6$): δ 10.6 (s, 1H), 9.85 (s, 1H), 8.71 (s, 1H), 8.28 (m, 1H), 7.80 (s, 1H), 7.45 (m, 1H), 4.75 (m, 1H), 3.52–3.80 (m, 2H), 3.32 (m, 2H), 3.05 (m, 1H), 2.14 (m, 1H), 1.94 (m, 3H), 1.50 (m, 1H), 1.35 (m, 2H), 1.26 (m, 3H), d 0.84 (m, 3H). ES-MS calcd. for C$_{18}$H$_{25}$FN$_4$O$_5$ (396.42); found: 397.2 [M+H].

A-8 is prepared from 2-chlorocarbonyl-pyrrolidine-1-carboxylic acid benzyl ester and 5-fluoro-pyridin-2-ylamine as described for the synthesis of pyrrolidine-2-carboxylic acid pyridine-2-yl-amide (hydrobromic acid salt) in Example 1.

1-{2-R-[(benzyloxy-formyl-amino)-methyl]-hexanoyl}-pyrrolidine-2-S-carboxylic Acid (5-fluoro-pyridin-2-yl)-amide

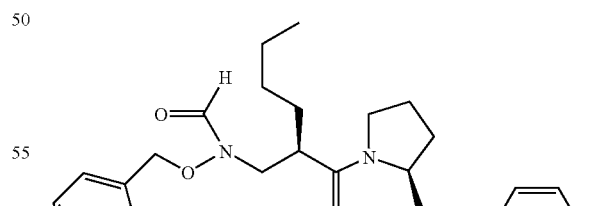

1H NMR (DMSO-d$_6$): δ 10.66 (s, 1H), 8.33 (m, 1H), 8.10 (m, 1H), d 7.75 (m, 1H), 7.44 (m, 5H), 7.14 (m, 1H), 4.88 (s, 2H), 4.59 (m, 1H), 3.67 (m, 2H), 3.55 (m, 2H), 2.94 (m, 1H), 1.72–2.12 (m, 4H), 1.48 (m, 1H), 1.34 (m, 1H), 1.26 (m, 4H), 0.86 (m, 3H). ES-MS calcd. for C$_{25}$H$_{31}$FN$_4$O$_4$ (470.55); found 471.4 [M+H].

1-{2-R-[(benzyloxy-formyl-amino)-methyl]-hexanoyl}-pyrrolidine-2-S-carboxylic Acid (5-fluoro-1-oxy-pyridin-2-yl)-amide

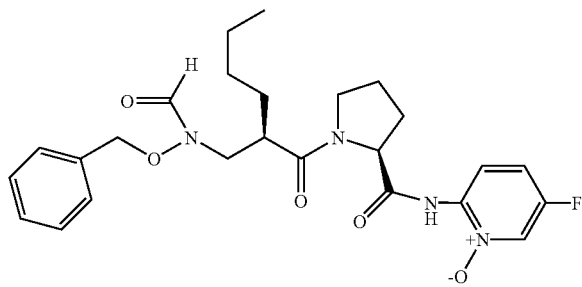

1H NMR (DMSO-d₆): δ 10.61 (s, 1H), 8.73 (m, 1H), 8.26 (m, 1H), 7.90 (m, 1H), d 7.42 (m, 5H), 7.11–7.30 (m, 1H), 4.86 (s, 2H), 4.78 (m, 1H), 3.67 (m, 2H), 3.56 (m, 2H), 2.92 (m, 1H), d 2.01 (m, 1H), 1.91 (m, 2H), 1.82 (m, 1H), 1.48 (m, 1H), 1.36 (m, 1H), 1.24 (m, 4H), d 0.83 (m, 3H). ES-MS calcd. for $C_{25}H_{31}FN_4O_5$ (486.55); found: 487.4 [M+H].

EXAMPLE 37

6-[1-{2-R-[(formyl-hydroxy-amino)-methyl]-hexanoyl}-S-pyrrolidine-2-carbonyl)-amino] Nicotinic Acid Methyl Ester

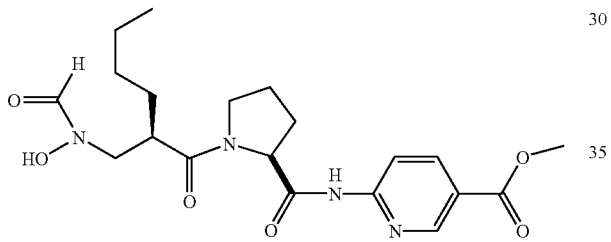

The title compound is prepared according to General Procedure A from 2-[(benzyloxy-formyl-amino)-methyl]-hexanoic acid A-7 (R=n-butyl) and 6-[(pyrrolidine-2-S-carbonyl)-amino]-nicotinic acid methyl ester A-8 [X=CH₂, n=1, R₁=6-amino-nicotinic acid methyl ester].

1H NMR (DMSO-d₆): δ 10.60 (s, 1H), 8.83 (s, 1H), 8.26 (1, d), 8.13 (d, 1H), 4.65 (1, m), 3.88 (s, 3H), 3.70 (m, 1H), 3.62 (m, 2H), 3.43 (m, 1H), 3.06 (m, 1H), 2.14 (m, 1H), 1.86–2.04 (m, 3H), 1.54 (m, 1H), 1.43 (m, 1H), 1.22–1.38 (m, 4H), 0.86 (t, 3H). ES-MS calcd. for $C_{20}H_{28}N_4O_6$ (420.46); found: 421.4 [M+H].

EXAMPLE 38

1-{2-R-[(formyl-hydroxy-amino)-methyl]-hexanoyl}-4-R-hydroxypyrrolidine-2-S-carboxylic Acid (5-methyl-pyridine-2-yl)-amide

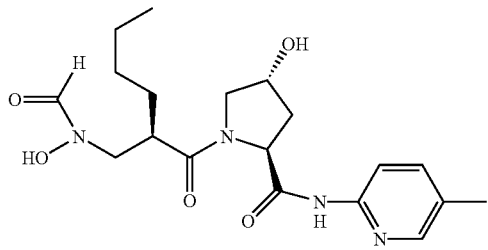

The title compound is prepared according to General Procedure A from 2-[(benzyloxy-formyl-amino)-methyl]-hexanoic acid A-7 (R=n-butyl) and 4-R-benzyloxy-pyrrolidine-2-carboxylic acid (5-methyl-pyridin-2-yl)-amide A-8 [X=(R)—CH—OH, n=1, R₁=2-(5-methyl)pyridyl].

1H NMR (DMSO-d₆): δ 8.4–8.3 (m, 1H), 8.17–8.01 (m, 1H), 7.86–7.75 (m, 1H), 5.36 (bs, 1H), 4.83–4.78 (t, J=8.42 & 7.67 Hz, 1H), 4.56 (bs, 1H), 3.89–3.73 (m, 2H), 3.52 (bs, 2H), 3.14 (bs, 1H), 2.69 (bs, 3H), 2.26–2.09 (m, 4H), 1.63–1.44 (m, 6H), 1.03 (bs, 3H). ES-MS: calcd. for $C_{19}H_{28}N_4O_5$ (392.46); found: 393.5 [M+H].

A-8 is prepared from 4-R-benzyloxy-pyrrolidine-1-carboxylic acid tert-butyl ester and 5-methyl-pyridin-2-ylamine under HATU condition to give proline amide derivative which on treatment with 4 M HCl in dioxane provides the desired amine as described for the synthesis of azetidine-2-S-(4-methyl-pyridin-2-yl)-amide hydrochloric acid salt in Example 18.

4-R-benzyloxy-pyrrolidine-2-S-carboxylic acid (5-methyl-pyridine-2-yl)-amide

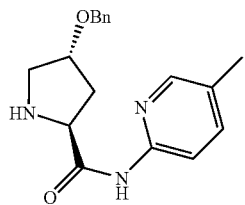

1H NMR (DMSO-d₆): δ 8.42 (bs, 1H), 8.15–8.12 (d, J=8.24 Hz, 1H), 7.96–7.92 (m, 1H), 7.61–7.47 (m, 5H), 4.77–4.56 (m, 4H), 3.68–3.58 (m, 2H), 2.97–2.90 (m, 1H), 2.69 (bs, 3H), 2.27–2.17 (m, 1H). ES-MS: calcd. for $C_{18}H_{21}N_3O_2$ (311.38); found: 312.5 [M+H].

4-R-benzyloxy-1-{2-R-[(formyl-hydroxy-amino)-methyl]-hexanoyl}-pyrrolidine-2-S-carboxylic Acid (5-methyl-pyridine-2-yl)-amide

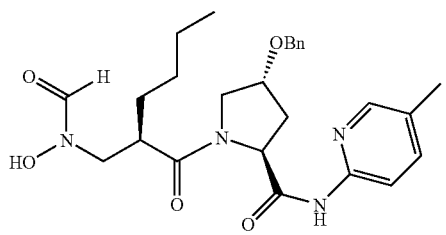

1H NMR (DMSO-d₆): δ 8.4–8.3 (m, 1H), 8.14–8.01 (m, 1H), 7.8–7.76 (d, J=8.52 Hz, 1H), 7.56–7.48 (m, 5H), 4.85–4.8 (t, J=7.42 & 7.69 Hz, 1H), 4.75–4.46 (m, 2H), 4.05 (bs, 1H), 4.0–3.68 (m, 2H), 3.54 (bs, 2H), 3.16 (bs, 1H), 2.69 (bs, 3H), 2.49–2.23 (m, 4H), 1.64–1.44 (m, 6H), 1.04 (bs, 3H). ES-MS: calcd. for $C_{26}H_{34}N_4O_5$ (482.57); found: 483.5 [M+H].

EXAMPLE 39

1-{2-R-[(formyl-hydroxy-amino)-methyl]-hexanoyl}-4-S-hydroxypyrrolidine-2-S-carboxylic Acid (5-methyl-pyridine-2-yl)-amide

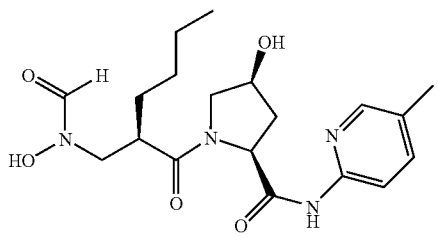

The title compound is prepared according to General Procedure A from 2-[(benzyloxy-formyl-amino)-methyl]-hexanoic acid A-7 (R=n-butyl) and 4-S—O-benzoyl-pyrrolidine-2-carboxylic acid (5-methyl-pyridin-2-yl)-amide A-8 [X=(R)—CH—OH, n=1, $R_1$=2-(5-methyl)pyridyl].

1H NMR (DMSO-$d_6$): δ 8.31–8.38 (d, J=7.42 Hz, 1H), 8.16–8.11 (m, 1H), 7.8–7.76 (m, 1H), 5.51–5.5 (d, J=4.95 Hz, 1H), 4.63 (bs, 1H), 4.52–4.35 (d, J=4.95 Hz, 1H), 4.02–3.68 (m, 2H), 3.52 (bs, 2H), 2.70 (bs, 1H), 2.69 (bs, 3H), 2.21–1.97 (m, 4H), 1.64–1.42 (m, 6H), 1.05–1.03 (d, J=6.04 Hz, 3H). ES-MS: calcd. for $C_{19}H_{28}N_4O_5$ (392.46); found: 393.5 [M+H].

4-S—O-benzoyl-pyrrolidine-2-S-carboxylic Acid (5-methyl-pyridine-2-yl)-amide

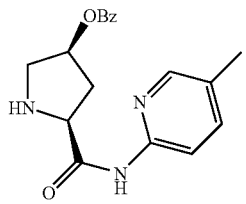

A-8 is prepared by the inversion of 4-R-hydroxy-pyrrolidine-1-carboxylic acid butyl (5-methyl-pyridin-2-yl)-am under Mitsunobu condition to give 4-S—O-benzyloxy proline amide derivative which on treatment with 4 M HCl in dioxane provides the desired amine as described for the synthesis of azetidine-2-S-(4-methyl-pyridin-2-yl)-amide hydrochloric acid salt in Example 18.

1H NMR (DMSO-$d_6$): δ 8.38 (bs, 1H), 8.15–8.06 (m, 2H), 7.92–7.8 (m, 4H), 7.66–7.61 (t, J=7.69 Hz, 1H), 5.74 (bs, 1H), 4.89 (bs, 1H), 3.83 (bs, 2H), 3.03–2.94 (m, 1H), 2.7–2.45 (m, 4H). ES-MS: calcd. for $C_{18}H_{19}N_3O_3$ (325.37); found: 326.4 [M+H].

EXAMPLE 40

1-{2-R-[(formyl-hydroxy-amino)-methyl]-hexanoyl}-4-R-hydroxypyrrolidine-2-S-carboxylic Acid (4-ethyl-pyridine-2-yl)-amide

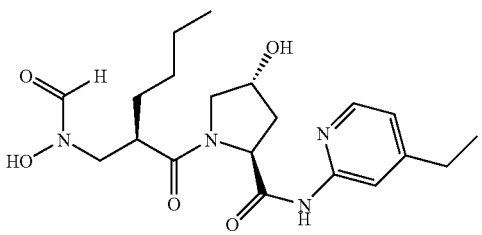

The title compound is prepared according to General Procedure A from 2-[(benzyloxy-formyl-amino)-methyl]-hexanoic acid A-7 (R=n-butyl) and pyrrolidine-2-carboxylic acid (4-ethyl-pyridin-2-yl)-amide A-8 [X=(R)—CH—OH, n=1, $R_1$=2-(4-ethyl)pyridyl].

1H NMR (DMSO-$d_6$): δ 8.38–8.36 (d, J=4.945 Hz, 1H), 8.12–8.01 (m, 1H), 7.16–7.14 (m, 1H), 5.37–5.36(d, J=2.3 Hz, 1H), 4.85–4.8 (t, J=7.69 Hz, 1H), 4.57 (bs, 1H), 3.89–3.55 (m, 2H), 3.52 (bs, 2H), 3.14 (bs, 1H), 2.82–2.6 (m, 2H), 2.26–2.09 (m, 4H), 1.63–1.33 (m, 9H), 1.04 (bs, 3H). ES-MS: calcd. for $C_{20}H_{30}N_4O_5$ (406.48); found: 407.5 [M+H].

A-8 is prepared from 4-R-benzyloxy-pyrrolidine-1-carboxylic acid tert-butyl ester and 4-ethyl-pyridin-2-ylamin under HATU condition to give proline amide derivative which on treatment with 4 M HCl in dioxane provides the desired amine as described for the synthesis of azetidine-2-S-(4-methyl-pyridin-2-yl)-amide hydrochloric acid salt in Example 18.

4-R-benzyloxy-pyrrolidine-2-S-carboxylic Acid (4-ethyl-pyridine-2-yl)-amide

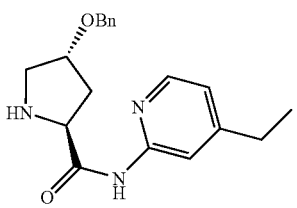

1H NMR (DMSO-$d_6$): δ 8.48–8.46 (d, J=5.22 Hz, 1H), 8.11 (bs, 1H), 7.62–7.34 (m, 8H), 4.81–4.56 (m, 4H), 3.69–3.59 (m, 2H), 2.98–2.83 (m, 3H), 2.29–2.19 (m, 1H), 1.41–1.38 (t, J=5.49 & 2.2 Hz, 3H). ES-MS: calcd. for $C_{19}H_{23}N_3O_2$ (325.41); found: 326.3 [M+H].

EXAMPLE 41

1-{2-R-[(formyl-hydroxy-amino)-methyl]-hexanoyl}-4-R-hydroxypyrrolidine-2-S-carboxylic Acid (5-trifluoromethyl-pyridine-2-yl)-amide

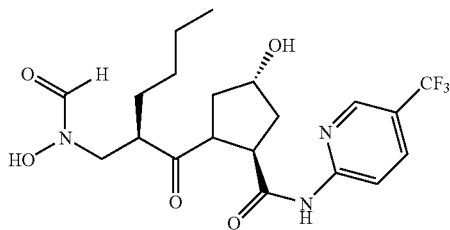

The title compound is prepared according to General Procedure A from 2-[(benzyloxy-formyl-amino)-methyl]-hexanoic acid A-7 (R=n-butyl) and pyrrolidine-2-carboxylic acid (5-trifluoromethyl-pyridin-2-yl)-amide A-8 [X=(R)—CH—OH, n=1, $R_1$=2-(5-trifluomethylethyl)-pyridyl.

1H NMR (DMSO-$d_6$): δ 8.44–8.3 (m, 2H), 8.01 (bs, 1H), 4.88–4.83 (t, J=7.69 Hz, 1H), 4.57 (bs, 1H), 3.91–3.66 (m, 4H), 3.15 (bs, 1H), 2.3–2.13 (m, 2H), 1.63–1.45 (m, 6H), 1.03 (bs, 3H). ES-MS: calcd. for $C_{19}H_{25}F_3N_4O_5$ (446.43); found: 447.3 [M+H].

A-8 is prepared from 4-R-benzyloxy-pyrrolidine-1-carboxylic acid tert-butyl ester and 5-trifluoromethyl-pyridin-2-ylamine under HATU condition to give proline amide derivative which on treatment with 4 M HCl in dioxane provides the desired amine as described for the synthesis of azetidine-2-S-(4-methyl-pyridin-2-yl)-amide hydrochloric acid salt in Example 18.

4-R-benzyloxy-pyrrolidine-2-S-carboxylic acid (5-trifluoromethyl-pyridine-2-yl)-amide

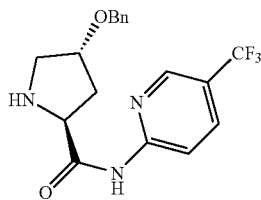

1H NMR (DMSO-$d_6$): δ 8.98 (bs, 1H), 8.5–8.42 (m, 2H), 7.62–7.47 (m, 5H), 4.84–4.56 (m, 4H), 3.69–3.61 (m, 2H), 2.97–2.91 (m, 1H), 2.3–2.21 (m, 1H). ES-MS: calcd. for $C_{18}H_{18}F_3N_3O_2$ (365.36); found: 366.3 [M+H].

EXAMPLE 42

4-S-fluoro-1-{2-R-[(formyl-hydroxy-amino)-methyl]-hexanoyl}-pyrrolidine-2-S-carboxylic Acid (5-methyl-pyridine-2-yl)-amide

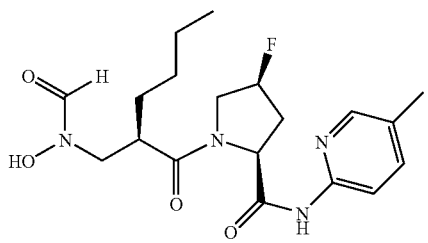

The title compound is prepared according to General Procedure A from 2-[(benzyloxy-formyl-amino)-methyl]-hexanoic acid A-7 (R=n-butyl) and 4-S-fluoro-pyrrolidine-2-carboxylic acid (5-methyl-pyridin-2-yl)-amide A-8 [X=(S)—CH—F, n=1, $R_1$=2-(5-methyl)-pyridyl.

1H NMR (DMSO-$d_6$): δ 8.34–8.32 (bs, 1H), 8.1–8.05 (m, 1H), 7.83–7.80 (d, J=8.52 Hz, 1H), 5.63–5.45 (d, J=54.1 Hz, 1H), 4.9–4.86 (d, J=9.89 Hz, 1H), 4.22–3.5 (m, 4H), 3.18 (bs, 1H), 2.69 (bs, 3H), 2.59–2.44 (m, 2H), 1.69–1.32 (m, 6H), 1.08–1.03 (t, J=6.87 Hz, 3H). ES-MS: calcd. for $C_{19}H_{27}FN_4O_4$ (394.44); found: 395.4 [M+H].

4-R-hydroxy-pyrrolidine-2-S-carboxylic acid (5-methyl-pyridine-2-yl)-amide

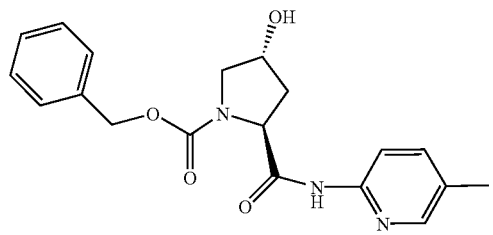

The coupling of O-tert butyl protected proline (1 mmol) with 5-picoline (1.5 mmol) in DMF (5 mL) under HATU (1.3 mmol) and N,N-diisopropylethyl amine (5 mmol) condition followed by removal of O-tert butyl with TFA-dichloroethane (1:1) provides the title compound.

1H NMR (DMSO-$d_6$): δ 8.34–8.32 (t, J=1.5 & 3.3 Hz, 1H), 8.18–8.14 (m, 1H), 7.82–7.77 (m, 1H), 7.57–7.24 (m, 5H), 5.95–5.1 (m, 3H), 4.83–4.72 (m, 1H), 4.5 (bs, 1H), 3.75–3.59 (m, 4H), 2.7–2.67 (m, 3H), 2.38–2.31 (m, 1H), 2.18–2.1 (m, 1H). ES-MS: calcd. for $C_{19}H_{21}N_3O_4$ (355.15); found: 356.4 [M+H].

4-S-fluoro-pyrrolidine-2-S-carboxylic Acid (5-methyl-pyridine-2-yl)-amide

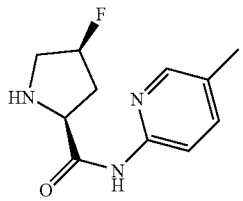

The above hydroxy compound (2 mmol) in methylenechloride (20 mL) is treated with N'N-diethylamino sulphur trifluoride (DAST; 4 mmol) at −70° C. Then, reaction mixture is stirred at rt for 16 hours and washed with cold aq. NaHCO$_3$ solution, dried and concentrated under reduced pressure. It is purified on silica gel column chromatography to give N-protected derivative which on treatment with HBr—AcOH provides amino compound.

1H NMR (DMSO-$d_6$): δ 8.41 (bs, 1H), 8.11–8.09 (d, J=8.24 Hz, 1H), 7.92–7.05 (m, 1H), 5.71–5.53 (d, J=52.47 Hz, 1H), 4.8 (bs, 1H), 3.84–3.67 (m, 2H), 3.04–2.81 (m, 1H), 2.69 (bs, 3H), 2.68–2.09 (m, 1H). ES-MS: calcd. for $C_{11}H_{14}FN_3O$ (223.25); found: 224.4 [M+H].

EXAMPLE 43

4-R-fluoro-1-{2-R-[(formyl-hydroxy-amino)-methyl]-hexanoyl}-pyrrolidine-2-S-carboxylic Acid (5-methyl-pyridine-2-yl)-amide

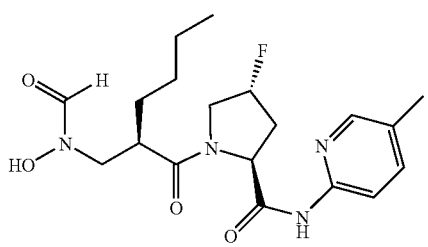

The title compound is prepared according to General Procedure A from 2-[(benzyloxy-formyl-amino)-methyl]-hexanoic acid A-7 (R=n-butyl) and 4-R-fluoro-pyrrolidine-2-carboxylic acid (5-methyl-pyridin-2-yl)-amide A-8 [X=(R)—CH—F, n 1, $R_1$=2-(5-methyl)-pyridyl.

1H NMR (DMSO-$d_6$): δ 8.34–8.31 (d, J=7.42 Hz, 1H), 8.15–8.12 (d, J=8.51 Hz, 1H), 7.99–7.73 (m, 1H), 5.66–5.48 (d, J=52.7 Hz, 1H), 4.87–4.81 (t, J=8.52 & 8.24 Hz, 1H), 4.26–3.56 (m, 2H), 3.52 (bs, 2H), 3.14 (bs, 1H), 2.69–2.68 (t, J=1.92 & 1.65 Hz, 3H), 2.49–2.17 (m, 2H), 1.64–1.42 (m, 6H), 1.08–1.04 (bs, 3H). ES-MS: calcd. for $C_{19}H_{27}FN_4O_4$ (394.44); found: 395.4 [M+H].

4-S-hydroxy-pyrrolidine-1,2-dicarboxylic acid 1-tert-butyl ester-2-methyl Ester

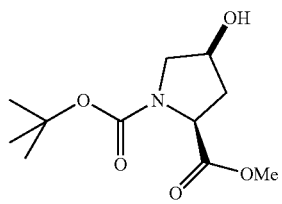

To a solution of trans-4-hydroxy compound (1 mmol), triphenyl phosphine (1.5 mmol) and benzoic acid (1.5 mmol) in THF (10 mL) is added N,N-diisopropyl-azo dicarboxylate (1.5 mmol) in THF (5 mL) dropwise at 0° C. It is stirred at rt for 16 hours. The solvent is removed under reduced pressure and residue is dissolved in ether. It is ice cooled to precipitate phosphine oxide which is removed by filtration and filtrate is concentrated under reduced pressure. The crude material is treated with methanolic sodium methoxide for 2 hours at 0° C. to give title cis-hydroxy compound.

1H NMR (DMSO-$d_6$) δ 4.43–4.35 (m, 2H), 3.80 (bs, 3H), 3.69 (m, 1H), 3.34–3.26 (m, 1H), 2.54–2.50 (m, 1H), 2.04–1.97 (m, 1H), 1.55 (bs, 9H). ES-MS: calcd. for $C_{11}H_{17}NO_5$ (245.44); found: 246.3 [M+H].

4-R-fluoro-pyrrolidine-2-S-carboxylic acid (5-methyl-pyridine-2-yl)-amide

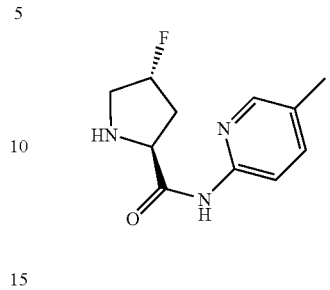

The fluorination of the above cis-hydroxy under similar reaction condition as described in Example 42 provides the trans-4-fluoro derivative which on saponification gives the corresponding acid. The amide is prepared from 4-R-fluoro-pyrrolidine-1-carboxylic acid tert-butyl ester and 5-methyl-pyridin-2-ylamine under HATU condition to give proline amide derivative which on treatment with 4 M HCl in dioxane provides the desired amine as described for the synthesis of azetidine-2-S-(4-methyl-pyridin-2-yl)-amide hydrochloric acid salt in Example 18.

1H NMR (DMSO-$d_6$): δ 8.418–8.416 (t, J=0.82 Hz, 1H), 8.14–8.11 (d, J=8.52 Hz, 1H), 7.97–7.94 (m, 1H), 5.78–5.59 (d, J=55.77 Hz, 1H), 4.83 (bs, 1H), 3.89–3.69 (m, 2H), 3.04–2.91 (m, 1H), 2.68 (bs, 3H), 2.44–2.29 (m, 1H). ES-MS: calcd. for $C_{11}H_{14}FN_3O$ (223.25); found: 224.4 [M+H].

EXAMPLE 44

4,4-difluoro-1-{2-R-[(formyl-hydroxy-amino)-methyl]-hexanoyl}-pyrrolidine-2-S-carboxylic Acid (5-methyl-pyridine-2-yl)-amide

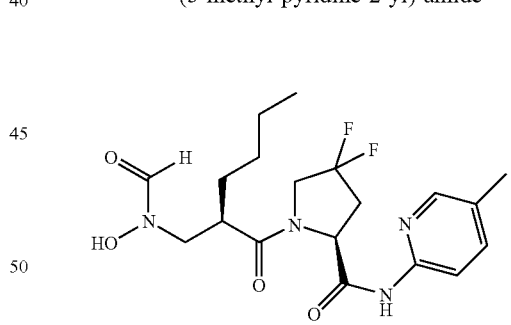

The title compound is prepared according to General Procedure A from 2-[(benzyloxy-formyl-amino)-methyl]-hexanoic acid A-7 (R=n-butyl) and 4-difluoro-pyrrolidine-2-carboxylic acid (5-methyl-pyridin-2-yl)-amide A-8 [X=CF$_2$, n=1, $R_1$=2-(5-methyl)-pyridyl.

1H NMR (DMSO-$d_6$): δ 8.34 (bs, 1H), 8.13–8.1 (d, J=8.24 Hz, 1H), 7.87–7.78 (m, 1H), 4.94–4.91 (d, J=8.24 Hz, 1H), 4.49–4.16 (m, 1H), 3.75–3.3 (m, 3H), 2.97 (bs, 1H), 2.94–2.88 (m, 1H), 2.75–2.66 (m, 4H), 1.65–1.45 (m, 6H), 1.06–1.04 (d, J=6.04 Hz, 3H). ES-MS: calcd. for $C_{19}H_{26}F_2N_4O_4$ (412.44); found: 413.5 [M+H].

4-oxo-pyrrolidine-1,2-dicarboxylic Acid 1-tert-butyl ester-2-methyl Ester

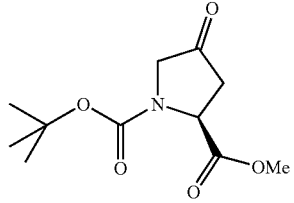

To a solution of oxalyl chloride (1.3 mmol) in methylene chloride (5 mL) is added DMSO (2.6 mmol) dropwise at −70° C. After 20 minutes, a solution of trans-hydroxy compound (1 mmol) in methylene chloride (5 mL) is added to reaction mixture. The reaction mixture is warmed to −60° C. and triethylamine is added to it. The reaction mixture is warmed up to 0° C. and diluted with more methylene chloride. It is washed with saline, 10% aq. citric acid, dried and concentrated under reduced pressure. The purification over silica gel with 20–30% EtOAc in hexane gives the 4-oxo compound.

1H NMR (CDCl$_3$): δ 4.83–4.71 (m, 1H), 3.91–3.79 (m, 2H), 3.77 (bs, 3H), 2.98–2.88 (m, 1H), 2.62–2.56 (m, 1H), 1.48 (bs, 9H). ES-MS: calcd. for C$_{11}$H$_{17}$NO$_5$ (243.44); found: 244.3 [M+H].

4-di-fluoro-pyrrolidine-2-S-carboxylic acid (5-methyl-pyridine-2-yl)-amide

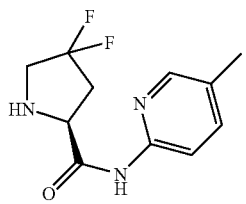

The fluorination of the above 4-oxo compound under similar reaction condition as described in Example 42 provides the 4-di-fluoro derivative which on saponification gives the corresponding acid. A-8 is prepared from 4-di-fluoro-pyrrolidine-1-carboxylic acid tert-butyl ester and 5-methyl-pyridin-2-ylamine under HATU condition to give proline amide derivative which on treatment with 4 M HCl in dioxane provides the desired amine as described for the synthesis of azetidine-2-S-(4-methyl-pyridin-2-yl)-amide hydrochloric acid salt in Example 18.

1H NMR (DMSO-d$_6$): δ 8.41–8.407 (t, J=0.82 Hz, 1H), 8.13–8.10 (d, J=8.52 Hz, 1H), 7.94–7.91 (m, 1H), 4.98–4.93 (t, J=8.24 Hz, 1H), 4.02–3.93 (m, 2H), 3.26–3.2 (m, 1H), 2.94–2.84 (m, 1H), 2.69–2.68 (t, J=1.92 & 1.65 Hz, 3H). ES-MS: calcd. for C$_{11}$H$_{13}$F$_2$N$_3$O (241.24); found: 242.4 [M+H].

EXAMPLE 45

1-{2-R-[(formyl-hydroxy-amino)-methyl]-hexanoyl}-4-R-methoxy-pyrrolidine-2-S-carboxylic Acid (5-methyl-pyridin-2-yl)-amide

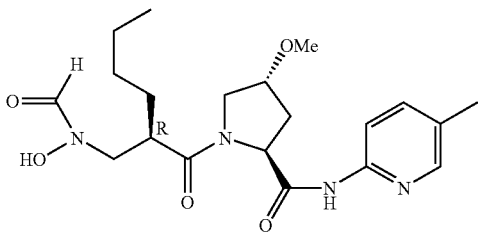

The title compound is prepared according to General Procedure A from 2-[(benzyloxy-formyl-amino)-methyl]-hexanoic acid A-7 (R=n-butyl) and 4-trans-methoxy-pyrrolidine-2-carboxylic acid (5-methyl-pyridin-2-yl)-amide A-8 [X=4-trans-CH—OMe, n=1, R$_1$=2-(5-methyl)-pyridyl.

1H NMR (DMSO-d$_6$): δ 10.6 (s, 1H), 9.90 (s, 1H), 8.33–8.32 (m, 1H), 8.14–8.11 (m, 1H), 7.79–7.77 (m, 1H), 4.78–4.72 (m, 1H), 4.24 (bs, 1H), 3.97–3.78 (m, 2H), 3.69–3.67 (m, 1H), 3.52–3.34 (m, 4H), 3.15 (bs, 1H), 2.49–2.36 (m, 4H), 2.24–2.12 (m, 1H), 1.64–1.44 (m, 6H), 1.10–0.993 (m, 3H). ES-MS: calcd. for C$_{20}$H$_{30}$N$_4$O$_5$ (406.48); found: 407.5 [M+H].

A-8 is prepared from 4-R-hydroxy-pyrrolidine-1,2-dicarboxylic acid 1-tert-butyl ester and 5-methyl-pyridin-2-ylamine as described below.

4-R-methoxy-pyrrolidine-1,2-dicarboxylic Acid 1-tert-butyl Ester 2-methyl Ester

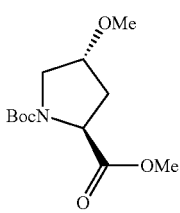

To a DMF solution (70 mL) of 4-R-hydroxy-pyrrolidine-1,2-dicarboxylic acid 1-tert-butyl ester (5.0 g, 20.4 mmol, 1 equiv.) are successively added Ag$_2$O (14.2 g, 61 mmol, 3 equiv.) and methyl iodide (7.0 mL, 102 mmol, 5 equiv.) at 0° C. The reaction mixture is allowed to come to rt overnight. The reaction mixture is diluted with excess EtOAc, and the insoluble salts are removed by filtration through Celite. The reaction mixture is washed with water, sat. NaHCO$_3$ and 10% sodium thiosulfate. The organic layer is dried over anhydrous Na$_2$SO$_4$, filtered and concentrated to give a light yellow oil.

1H NMR (DMSO-d$_6$): δ 4.37–4.30 (m, 1H), 4.15–4.11 (m, 1H), 3.85–3.82 (m, 3H), 3.60–3.58 (m, 2H), 3.40 (s, 3H), 2.54–2.47 (m, 1H), 2.18–2.08 (m, 1H), 1.58 (s, 3H), 1.51 (m, 6H). ES-MS: calcd. for C$_{12}$H$_{21}$NO$_5$ (259.30); found: 282.4 [M+Na].

4-R-methoxy-pyrrolidine-1,2-dicarboxylic Acid 1-tert-butyl Ester

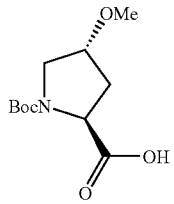

The above methyl ester (5.0 g, 19.2 mmol, 1 equiv.) is taken in a 3:1 solution of THF/water (180 mL/60 mL) and cooled to 0° C. A solution of lithium hydroxide (1 M solution in water, 38 mL, 38 mmol, 2 equiv.) is added, and the resulting mixture is stirred at 0° C. for 2 hours and at rt for 2 hours. The basic reaction mixture is quenched with Amberlite IR-120 resin (H+) to pH 4–5 at 0° C. The resin is filtered off and rinsed with EtOAc, and the mixture is concentrated to remove solvents. The residual oil is co-evaporated twice with toluene, and concentrated to give a light yellow oil.

1H NMR (DMSO-$d_6$): δ 12.8 (bs, 1H), 4.32–4.20 (m, 1H), 4.13 (bs, 1H), 3.59–3.33 (m, 5H), 2.52–2.42 (m, 1H), 2.17–2.06 (m, 1H), 1.58–1.53 (m, 9H). ES-MS: calcd. for $C_{11}H_{19}NO_5$ (245.27); found: 2.44 [M–H].

4-R-methoxy-2-S-(5-methyl-pyridin-2-ylcarbamoyl)-pyrrolidine-1-carboxylic Acid tert-butyl Ester

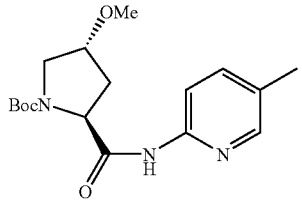

To a DMF solution (35 mL) of above carboxylic acid (4.20 g, 17.1 mmol, 1 equiv.) are successively added Hunig's base (15 mL, 86 mmol, 5 equiv.), 2-amino-5-picoline (2.78 g, 26 mmol, 1.5 equiv.), and HATU (9.77 g, 26 mmol, 1.5 equiv.) at 0° C. The resulting mixture is stirred at rt for 18 hours. The mixture is partitioned between excess EtOAc and 10% citric acid. The organic layer is washed with brine and saturated NaHCO₃, dried over anhydrous Na₂SO₄, filtered and concentrated. The residue is purified by FC (hexane:EtOAc=100% to 50%:50%) to give the title compound as a white solid.

1H NMR (DMSO-$d_6$): δ 10.7–10.6 (m, 1H), 8.33 (s, 1H), 8.21–8.14 (m, 1H), 7.82–7.77 (m, 1H), 4.63–4.54 (m, 1H), 4.15 (bs, 1H), 3.65–3.61 (m, 2H), 3.41 (s, 3H), 2.52–2.43 (m, 4H), 2.18–2.08 (m, 1H), 1.58–1.42 (m, 9H). ES-MS: calcd. for $C_{17}H_{25}N_3O_4$ (335.40); found: 336.5 [M+H].

4-R-methoxy-pyrrolidine-2-S-carboxylic Acid (5-methyl-pyridin-2-yl)-amide (Hydrochloric Acid Salt)

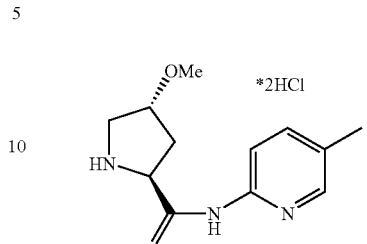

The Boc-prolineaminopicoline (2.78 g, 8.29 mmol, 1 equiv.) is charged with 4 N HCl/dioxane (21 mL, 83 mmol, 10 equiv.) at rt and allowed to stir for 18 hours. The mixture is concentrated, and the residue is co-evaporated twice with toluene, and concentrated to give a pink solid.

1H NMR (DMSO-$d_6$): δ 11.4 (bs, 1H), 10.4 (bs, 1H), 8.41–8.40 (m, 1H), 8.15–8.12 (m, 1H), 7.92–7.88 (m, 1H), 4.69–4.63 (m, 1H), 4.36–4.33 (m, 1H), 3.69–3.56 (m, 1H), 3.53–3.44 (m, 4H), 2.87–2.80 (m, 1H), 2.46 (s, 1H), 2.20–2.11 (m, 1H). ES-MS: calcd. for $C_{12}H_{17}N_3O_2$*2HCl (235.28); found: 236.4 [M+H] free base.

1-{2-R-[(benzyloxy-formyl-amino)-methyl]-hexanoyl}-4-R-methoxy-pyrrolidine-2-S-carboxylic Acid (5-methyl-pyridin-2-yl)-amide

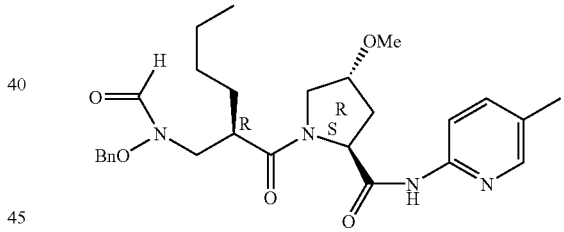

To a DMF solution (6 mL) of trans-methoxyprolineaminopicoline HCl salt (679 mg, 2.20 mmol, 1.5 equiv.), are successively added Hunig's base (1.3 ml, 7.34 mmol, 5 equiv.), Versiacid VRI 172 (410 mg, 1.47 mmol, 1 equiv.), and HATU (837 mg, 2.20 mmol, 1.5 equiv) at 0° C. The resulting mixture is stirred at rt for 18 hours. The mixture is partitioned between excess EtOAc and 10% citric acid. The organic layer is washed with brine and saturated NaHCO₃, dried over anhydrous Na₂SO₄, filtered and concentrated. The residue is purified by FC (CH₂Cl₂:ACE =100% to 50%:50%) to give the title compound as a colorless oil.

1H NMR (DMSO-$d_6$): δ 10.6 (s, 1H), 8.37–8.33 (m, 1H), 8.14–8.05 (m, 1H), 7.79–7.76 (m, 1H), 7.61–7.57 (m, 6H), 5.06 (s. 2H), 4.79–4.70 (m, 1H), 4.21 (m, 1H), 3.85–3.83 (m, 2H), 3.65 3.45 (m, 2H), 3.36 (bs, 3H), 4.14 (bs, 1H), 2.49–2.40 (m, 4H), 2.19–2.11 (m, 1H), 1.63–1.33 (m, 6H), 1.05–0.992 (m, 3H). ES-MS: calcd. for $C_{27}H_{36}N_4O_5$ (496.60); found: 497.7 [M+H].

EXAMPLE 46

1-{2-R-[(formyl-hydroxy-amino)-methyl]-hexanoyl}-4-S-methoxy-pyrrolidine-2-S-carboxylic Acid (5-methyl-pyridin-2-yl)-amide

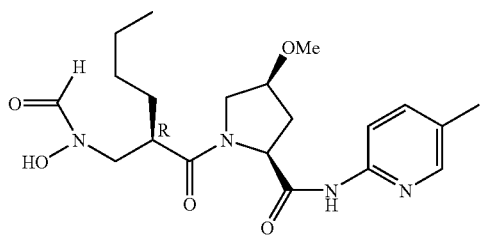

The title compound is prepared according to General Procedure A from 2-[(benzyloxy-formyl-amino)-methyl]-hexanoic acid A-7 (R=n-butyl) and 4-cis-methoxy-pyrrolidine-2-carboxylic acid (5-methyl-pyridin-2-yl)-amide A-8 [X=4-cis-CH—OMe, n=1, R$_1$=2-(5-methyl)-pyridyl].

1H NMR (DMSO-d$_6$): δ 10.3 (bs, 1H), 9.89 (bs, 1H), 8.30 (bs, 1H), 8.13–8.10 (m, 1H), 7.99 (bs, 1H), 7.80–7.77 (m, 1H), 4.66 (bs, 1H), 4.44–4.14 (m, 2H), 3.74–3.52 (m, 5H), 3.41–3.28 (m, 2H), 2.56–2.42 (m, 4H), 2.24–2.12 (m, 1H), 1.66–1.46 (m, 6H), 1.05–1.03 (m, 3H). ES-MS: calcd. for C$_{20}$H$_{30}$N$_4$O$_5$ (406.48); found: 407.5 [M+H].

A-8 is prepared from 4-S-hydroxy-pyrrolidine-1,2-dicarboxylic acid 1-tert-butyl ester and 5-methyl-pyridin-2-ylamine as described for the corresponding trans methoxy compound (Example 45).

4-S-methoxy-pyrrolidine-1,2-dicarboxylic Acid 1-tert-butyl Ester 2-methyl Ester

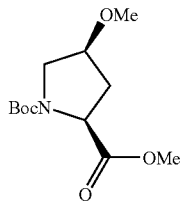

1H NMR (CDCl$_3$): δ 4.45–4.33 (m, 2H), 3.96–3.91 (m, 1H), 3.73 (s, 3H), 3.68–3.45 (m, 1H), 3.28 (s, 3H), 2.33–2.22 (m, 2H), 1.48–1.42 (m, 9H). ES-MS: calcd. for C$_{12}$H$_{21}$NO$_5$ (259.30); found: 282.4 [M+Na].

4-S-methoxy-pyrrolidine-1,2-dicarboxylic acid 1-tert-butyl Ester

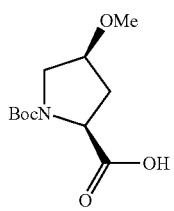

1H NMR (DMSO-d$_6$): δ 12.8 (bs, 1H), 4.36–4.29 (m, 1H), 4.10–4.07 (m, 1H), 3.75–3.68 (m, 1H), 3.41–3.35 (m, 4H), 2.58–2.49 (m, 1H), 2.21–2.14 (m, 1H), 1.58–1.53 (m, 9H). ES-MS: calcd. for C$_{11}$H$_{19}$NO$_5$ (245.27); found: 2.44 [M−H].

4-S-methoxy-2-S-(5-methyl-pyridin-2-ylcarbamoyl)-pyrrolidine-1-carboxylic Acid tert-butyl Ester

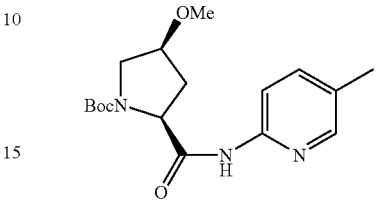

1H NMR (DMSO-d$_6$): δ 10.3–10.2 (m, 1H), 8.32–8.31 (m, 1H), 8.18–8.15 (m, 1H), 7.81–7.78 (m, 1H), 4.51–4.46 (m, 1H), 4.18–4.11 (m, 1H), 3.52 (s, 3H), 3.47–3.35 (m, 1H), 2.64–2.56 (m, 1H), 2.43 (s, 3H), 2.20–2.05 (m, 1H), 1.59–1.44 (m, 9H). ES-MS: calcd. for C$_{17}$H$_{25}$N$_3$O$_4$ (335.40); found: 336.5 [M+H].

4-S-methoxy-pyrrolidine-2-S-carboxylic Acid (5-methyl-pyridin-2-yl)-amide (Hydrochloric Acid Salt)

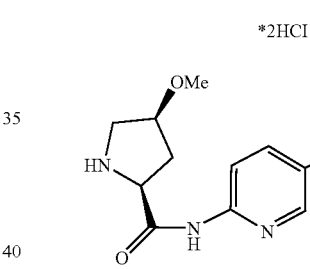

1H NMR (DMSO-d$_6$): δ 11.3 (bs, 1H), 10.6 (bs, 1H), 8.40–8.39 (m, 1H), 8.11–8.08 (m, 1H), 7.92–7.88 (m, 1H), 4.65–4.57 (m, 1H), 4.29–4.25 (m, 1H), 3.52–3.39 (m, 2H), 3.37 (s, 3H), 2.81–2.71 (m, 1H), 2.59–2.33 (m, 4H). ES-MS: calcd. for C$_{12}$H$_{17}$N$_3$O$_2$*2HCl (235.28); found: 236.4 [M+H] free base.

1-{2-R-[(benzyloxy-formyl-amino)-methyl]-hexanoyl}-4-S-methoxy-pyrrolidine-2-S-carboxylic acid (5-methyl-pyridin-2-yl)-amide

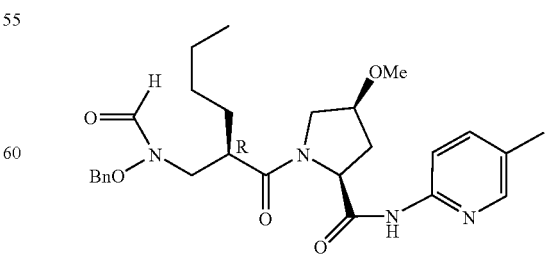

1H NMR (DMSO-d$_6$): δ 10.1 (bs, 1H), 8.43 (bs, 1H), 8.34–8.31 (m, 1H), 8.11–8.09 (m, 1H), 7.79–7.76 (m, 1H), 7.62 (m, 6H), 5.05 (s. 2H), 4.79 (bs, 1H), 4.62 (bs, 1H), 4.01–3.98 (m, 1H), 3.90–3.83 (m, 1H), 3.54–3.34 (m, 5H), 3.17 (bs, 1H), 2.46–2.42 (m, 4H), 2.13–2.09 (m, 1H), 1.50–1.39 (m, 6H), 1.15–0.992 (m, 3H). ES-MS: calcd. for $C_{27}H_{36}N_4O_5$ (496.60); found: 497.7 [M+H].

Preferred compounds according to the invention are e.g. the compounds of Examples 6, 8, 9, 14, 15, 21, 22, 28, 29 or 36. Even more preferred are those of Examples 14 or 36.

The compounds of the invention, e.g., the compounds of formula (I), in free form or in pharmaceutically acceptable salt from or a prodrug thereof, exhibit valuable pharmacological properties, e.g., as anti-infectious agents, e.g., as indicated in in vitro and in vivo tests and are therefore indicated for therapy.

A. Inhibition of Peptide Deformylase Activity

The PDF/FDH coupled assay (see Lazennec et al., Anal. Biochem., Vol. 224, pp. 180–182 (1997)) is used. In this coupled assay, the formate released by PDF from its substrate fMAS is oxidized by the coupling enzyme FDH, reducing one molecule of $NAD^+$ to NADH, which causes an increase in absorption at 340 nM. All assays are carried out at rt in a buffer of 50 mM HEPES, pH 7.2, 10 mM NaCl, 0.2 mg/mL BSA, in half-area 96-well microtiter plates (Corning). The reaction is initiated by adding a mixture of 0.5 U/mL FDH, 1 mM $NAD^+$ and fMAS at the desired concentration. To determine the concentration needed to inhibit 50% of enzyme activity ($IC_{50}$) values, PDF is pre-incubated for 10 minutes with varying concentrations of the inhibitor, and the deformylation reaction is initiated by the addition of reaction mixture containing 4 mM fMAS. The initial reaction velocity, y, is measured as the initial rate of absorption increase at 340 nM using a SpectraMax plate reader (Molecular Devices, Sunnyvale, Calif.). The inhibitor concentration [In] at which 50% of the enzyme activity is inhibited, $IC_{50}$, is calculated using the following formula:

$$y = y_o/(1+[In]/IC_{50})$$

where $y_o$ is the reaction velocity in the absence of inhibitor. Solving this equation for $IC_{50}$ at the [In] when $y = y_o/2$ yields $IC_{50}$. The $IC_{50}$ is calculated based on a nonlinear least-square regression fit using a commercial software package (Deltapoint, Inc., Chicago, Ill.).

Using this assay, the $IC_{50}$ of various compounds of the invention is determined. The $IC_{50}$ for the various compounds is determined against deformylase enzyme containing nickel and zinc as the metal ion. The $IC_{50}$ values of preferred compounds of formula (I) determined for the zinc-containing deformylase range from about 0.001 μM to about 0.2 μM. The $IC_{50}$ values of preferred compounds of formula (I) determined for the nickel-containing deformylase ranged from about 0.005 μM to about 3 μM.

B. Assay for Testing Antimicrobial Activity

Minimum inhibitory concentrations (MICs) are determined using the microdilution method in 96-well format plates. Compounds are suspended in DMSO at 5 or 10 mg/mL and stored at 4° C. until used. They are diluted in Mueller-Hinton Broth (MHB) or Trypticase Soy Broth (TSB) and used for MIC determination. The range of concentrations tested is 64–0.0625 μg/mL final concentration using a two-fold dilution system.

The inoculum is prepared from cells grown on Trypticase Soy Agar (TSA) and incubated overnight at 35° C., 5–10 colonies are used to inoculate MHB or TSB broths, and the culture is incubated overnight at 35° C. The overnight culture is diluted 1:10, incubated for 1 hour at 35° C., diluted to the appropriate inoculum size and applied to the wells containing broth and test compound. Inoculum sizes are $2 \times 10^4$ CFU/mL.

Plates are incubated at 35° C. for 48 hours and MIC are recorded after 18 hours of incubation for bacteria. MIC is defined as the lowest concentration of a compound of the invention that does not produce visible growth after incubation.

Minimum inhibitory concentration for various preferred compounds of formula (I) ranges from about 0.25 μg/mL to about 32 μg/mL against *H. influenza* (four strains), from about 0.001 μg/mL to greater than 8 μg/mL against *S. aureus* (four strains), from about 0.016 μg/mL to about 16 μg/mL against *S. pneumonia* (four strains), and from about 0.008 μg/mL to about 16 μg/mL against *M. catarrhalis*. The deformylase enzyme is obtained from *E. coli*.

C. Demonstration of Selective Inhibition of PDF Compared to Matrilysin (MMP-7)

As noted previously, inhibitors which are selective for peptidyl deformylase over MMPs are desirable in order to avoid side effects.

In order to test the compounds of the invention for possible inhibitory effects on MMPs, the following assay for MMP-7 is used.

MMP-7 Assay

MMP-7 activity is assayed using a thio-peptide (Pro-Leu-Gly-S-Leu-Leu-Gly) as substrate. Upon enzyme hydrolysis, the thiolate is released as a product. The thiolate thus generated reacts with DTNB (dithionitrobenzene), giving rise to a yellow color which is monitored at 405 nM. The assay is carried out at rt; the assay buffer contains 50 mM Tricine, pH 7.5, 0.2 M NaCl, 10 mM $CaCl_2$, and 0.05% Brij, in a half-area 96-well microtiter plate. The reaction is initiated by adding a mixture of 200 TM DTNB and 100 TM thiopeptide in buffer. To determine $IC_{50}$ values, MMP-7 is preincubated for 10 minutes with varying concentrations of compounds of the invention, and the hydrolysis initiated by the addition of reaction mixture containing thiopeptide and DTNB. The reaction rate is recorded as the absorbance increase in $OD_{405}$ over 30 minutes using a SpectraMax plate reader (Molecular Devices, Sunnyvale, Calif.). The inhibitor concentration [In] at which 50% of the enzyme activity is inhibited, $IC_{50}$, is calculated using the following formula:

$$y = y_o/(1+[In]/IC_{50})$$

where $y_o$ is the reaction velocity in the absence of inhibitor. Solving this equation for $IC_{50}$ at the [In] when $y = y_o/2$ yields $IC_{50}$.

Using this assay, the $IC_{50}$ of various compounds of the invention are determined. The $IC_{50}$ of various preferred compounds of formula (I) against MMP-7 ranges from greater than 10 μM to greater than 100 μM, whereas the $IC_{50}$ of these same compounds against zinc-containing PDF ranges from about 0.005 μM to about 5 μM, and against nickel-containing PDF ranged from about 0.001 μM to about 0.3 μM. Accordingly, compounds of the invention have superior selectivity for PDF as compared to their activity against MMP-7. Similar selectivity of the compounds for peptidyl deformylase over MMP-1, MMP-2, MMP-3, MMP-9, MMP-13, MT-MMP-1, and tissue necrosis factor converting enzyme is observed. Similar selectivity is also observed over other metalloproteinases such as angiotensin converting enzyme.

D. Mouse Septicemia Model for Determining In Vivo Efficacy

CD1 female out-bred mice (Charles River Laboratories) weighing 18–22 g each are injected intraperitoneally with 0.5 mL of a suspension containing $5 \times 10^7$ cfu of S. aureus (Smith strain) in 7% hog gastric mucosa (mucin). The mice are treated, either subcutaneously (s.c.), intravenously (i.v.) or orally (p.o.), 1 hour and 5 hours after infection. Six groups of six mice each are given different dosage levels representing two-fold dilutions of each compound to be tested (range of 100–0.1 mg/kg). Vancomycin is used as the control antibiotic and is administered s.c. Compounds of the invention are formulated in PBS and untreated controls are dosed with vehicle alone.

Deaths in each group are monitored daily for 6 days and cumulative mortality is used to determine the 50% protective doses ($PD_{50}$), which are calculated using the method of Reed and Muench. The $PD_{50}$ (s.c.) in mice against S. aureus for several preferred compound of formula (I) ranges from about 0.1 mg/kg to greater than 12 mg/kg. The $PD_{50}$ (p.o.) in mice against S. aureus for these same compounds of formula (I) ranges from 1 mg/mL to greater than 12 mg/kg.

E. Pharmacokinetics Study of PDF Inhibitors in Mice

The pharmacokinetics of PDF compounds are determined in CD1 female out-bred mice (Charles River Laboratories) weighing 20–25 g. PDF compounds are formulated in 20% cyclodextrin (Aldrich) and filtered through 0.22 µM filter for sterilization. Either single compound or mixtures of 4–6 compounds as a cassette are administered i.v. and p.o. at 10 mL/kg. The dose ranged from 3–15 mg/kg for each compound. At 0.083, 0.25, 0.5, 1, 2, 4 and 7 hours after dosing, serum samples are collected via cardiac puncture under anesthesia. Groups of four mice are used for each time point. The serum samples are stored at −80° C. until analysis.

The serum protein is precipitated by addition of acetonitrile. The samples after protein precipitation are analyzed by LC/MS/MS method. Standard curve is obtained for each compound and used for determination of compound concentration in serum. The pharmacokinetics parameters including time of maximum concentration ($T_{max}$, maximum concentration ($C_{max}$), terminal half-life ($t_{1/2}$) and area under the curve (AUC), are calculated according to standard method. The oral bioavailability is calculated as the ratio of AUC of p.o. administration versus the AUC administered i.v. The preferred compounds of formula (I) exhibit oral bioavailability greater than 70%.

The compounds of the present invention are, therefore, useful for the treatment and/or prevention of infectious disorders caused by a variety of bacterial or prokaryotic organisms. Examples include, but are not limited to, Gram positive and Gram negative aerobic and anaerobic bacteria, including Staphylococci, e.g., S. aureus and S. epidermidis; Enterococci, e.g., E. faecalis and E. faecium; Streptococci, e.g., S. pneumoniae; Haemophilus, e.g., H. influenza; Moraxella, e.g., M. catarrhalis; Bacteroides, e.g., Bacteroides fragilis, Clostridium, e.g., Clostridium difficile, Niesseria, e.g., N. meningitidis and N. gonorrhoae, Legionella, and Escherichia, e.g., E. coli. Other examples include Mycobacteria, e.g., M. tuberculosis; intercellular microbes, e.g., Chlamydia and Rickettsiae; and Mycoplasma, e.g., M. pneumoniae; and Pseudomonas, e.g., P. aeruginosa; Helicobacter pylori; and parasites, e.g., Plasmodium falciparum.

As used herein, an "infectious disorder" is any disorder characterized by the presence of a microbial infection, such as the presence of bacteria. Such infectious disorders include, for example, central nervous system infections, external ear infections, infections of the middle ear, such as acute otitis media, infections of the cranial sinuses, eye infections, infections of the oral cavity, such as infections of the teeth, gums and mucosa, upper respiratory tract infections, lower respiratory tract infections, genitourinary infections, gastrointestinal infections, gynecological infections, septicemia, bone and joint infections, skin and skin structure infections, bacterial endocarditis, burns, antibacterial prophylaxis of surgery, antibacterial prophylaxis in immunosuppressed patients, such as patients receiving cancer chemotherapy, or organ transplant patients and chronic diseases caused by infectious organisms, e.g., arteriosclerosis.

The compounds may be used to treat a subject to treat, prevent, and/or reduce the severity of an infection. Subjects include animals, plants, blood products, cultures and surfaces, such as those of medical or research equipment, such as glass, needles, surgical equipment and tubing, and objects intended for temporary or permanent implantation into an organism. Preferred animals include mammals, e.g., mice, rats, cats, dogs, cows, sheep, pigs, horses, swine, primates, such as rhesus monkeys, chimpanzees, gorillas, and most preferably humans. Treating a subject includes, but is not limited to, preventing, reducing and/or eliminating the clinical symptoms caused by an infection of a subject by a microorganism; preventing, reducing and/or eliminating an infection of a subject by a microorganism; or preventing, reducing and/or eliminating contamination of a subject by a microorganism. The microorganism involved is preferably a prokaryote, more preferably a bacterium.

For the above uses the required dosage will of course vary depending on the mode of administration, the particular condition to be treated and the effect desired. The compositions may contain, for example, from about 0.1% by weight to about 99% by weight, e.g., from about 10–60% by weight, of the active material, depending on the method of administration. Where the compositions comprise dosage units, each unit will contain, for example, from about 1–1000 mg, e.g., 1–500 mg, of the active ingredient. The dosage as employed for adult human treatment will range, for example, from about 1–3000 mg per day, for instance 1500 mg per day depending on the route and frequency of administration. Such a dosage corresponds to about 0.015–50 mg/kg per day. Suitably the dosage is, for example, from about 5–20 mg/kg per day. Suitable unit dosage forms for oral administration comprise ca. 0.25–1500 mg active ingredient.

A "pharmaceutically acceptable carrier" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable carrier" as used in the specification and claims includes both one and more than one such carriers.

The compounds may be administered by any conventional route, e.g., locally or systemically e.g., orally, topically, parenterally, subdermally, or by inhalation and may be used for the treatment of bacterial infection in a subject, such as animals, preferably, mammals, more preferably, humans.

The compounds of the invention may be formulated for administration in any convenient way for use in human or veterinary medicine, by analogy with other antibiotics. Such methods are known in the art (see, e.g., Remington's Pharmaceutical Sciences, Easton, Pa.: Mack Publishing Co.) and are not described in detail herein.

The compositions may be in any form known in the art, including but not limited to tablets, capsules, wafers, fast melts (without wafers), powders, granules, lozenges, creams or liquid preparations, such as oral or sterile parenteral solutions or suspensions. The compounds may also be administered in liposomal, micellar or microemulsion formulations. The compounds may also be administered as prodrugs, where the prodrug administered undergoes biotransformation in the treated mammal to a form which is biologically active.

The topical formulations of the present invention may be presented as, for instance, ointments, creams or lotions, solutions, salves, emulsions, plasters, eye ointments and eye or ear drops, impregnated dressings, transdermal patches, sprays and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present, for example, from about 1% up to about 99% of the formulation. For example, they may form up to about 80% of the formulation.

Tablets and capsules for oral administration may be in unit dose presentation form, and may contain conventional excipients such as binding agents, for example, syrup, acacia, gelatin, sorbitol, tragacanth, or polyvinylpyrollidone; fillers, for example, lactose, sugar, maize-starch, calcium phosphate, sorbitol or glycine; tabletting lubricants, for example, magnesium stearate, talc, polyethylene glycol or silica; disintegrants, for example, potato starch; or acceptable wetting agents, such as sodium lauryl sulphate. The tablets may be coated according to methods well-known in standard pharmaceutical practice.

Oral liquid preparations may be in the form of, for example, aqueous or oily suspensions, solutions, emulsions, syrups or elixirs, or may be presented as a dry product for reconstitution with water or another suitable vehicle before use. Such liquid preparations may contain conventional additives, such as suspending agents, for example, sorbitol, methyl cellulose, glucose syrup, gelatin, hydroxyethyl cellulose, carboxymethyl cellulose, aluminium stearate gel or hydrogenated edible fats; emulsifying agents, for example, lecithin, sorbitan monooleate, or acacia; non-aqueous vehicles (which may include edible oils), for example, almond oil, oily esters such as glycerine, propylene glycol, or ethyl alcohol; preservatives, for example, methyl or propyl p-hydroxybenzoate or sorbic acid, and, if desired, conventional flavoring or coloring agents.

For parenteral administration, fluid unit dosage forms are prepared utilizing the compound and a sterile vehicle, water being preferred. The compound, depending on the vehicle and concentration used, may be either suspended or dissolved in the vehicle or other suitable solvent. In preparing solutions, the compound may be dissolved in water for injection and filter sterilized before filling into a suitable vial or ampule and sealing. Advantageously, agents such as a local anesthetic preservative and buffering agents may be dissolved in the vehicle. To enhance the stability, the composition may be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound may be sterilized by exposure to ethylene oxide before suspending in the sterile vehicle. Advantageously, a surfactant or wetting agent is included in the composition to facilitate uniform distribution of the compound.

The compounds of the invention, e.g., the compounds of formula (I), may be administered in free form or in pharmaceutically acceptable salt form, e.g., as indicated above. Such salts may be prepared in conventional manner and exhibit the same order of activity as the free compounds.

In accordance with the foregoing the present invention further provides:

1.1. A method for treating and/or preventing an infectious disorder in a subject, such as a human or other animal subject, comprising administering to the subject an effective amount of a compound of the invention, e.g., of formula (I), a pharmaceutically acceptable salt thereof or a prodrug thereof.

1.2. A method for inhibiting peptidyl deformylase in a subject comprising administering to the subject an effective peptidyl deformylase inhibiting amount of a compound of the invention, e.g., of formula (I), a pharmaceutically acceptable salt thereof or a prodrug thereof.

2. A compound of the invention, e.g., of formula (I), in free form or in a pharmaceutically acceptable salt form for use as a pharmaceutical, e.g., in any method as indicated under 1.1 or 1.2 above.

3. A pharmaceutical composition, e.g., for use in any of the methods as in 1.1 or 1.2 above comprising a compound of the invention, e.g., of formula (I), in free form or pharmaceutically acceptable salt form, e.g., in association with a pharmaceutically acceptable diluent or carrier therefor.

4. A compound of the invention, e.g., of formula (I), a pharmaceutically acceptable salt or a prodrug thereof for use as a pharmaceutical or in the preparation of a pharmaceutical composition for use in any method as indicated under 1.1 or 1.2 above.

"Treating" or "treatment" of a disease includes:
1. preventing the disease, i.e., causing the clinical symptoms of the disease not to develop in a subject, e.g., a mammal, that may be exposed to or predisposed to the disease but does not yet experience or display symptoms of the disease;
2. Inhibiting the disease, i.e., arresting or reducing the development of the disease or its clinical symptoms; or
3. relieving the disease, i.e., causing regression of the disease or its clinical symptoms.

An "effective peptidyl deformylase inhibiting amount" means the amount of a compound, a pharmaceutically acceptable salt thereof or a prodrug thereof, that when administered to a subject for treating an infectious disorder responsive to inhibition of peptidyl deformylase or for inhibiting peptidyl deformylase, is sufficient to inhibit peptidyl deformylase. The "effective peptidyl deformylase inhibiting amount" will vary depending on the compound, salt thereof or prodrug thereof, employed, the microorganism that is inhibited in the subject, the age, weight, sex, medical condition, species, disorder and its severity, of the subject to be treated, and the route of administration, but may nevertheless be readily determined by one skilled in the art.

The compounds of the invention, e.g., of formula (I), a pharmaceutically acceptable salt thereof or prodrug thereof, may be administered alone or in combination with another therapeutic agent. Examples of such therapeutic agents include, but are not limited to, other antibacterial agents, such as β-lactams, e.g., penicillins; cephalosporins; carbapenems; ketolides; quinolones, e.g., fluoroquinolones; macrolides, e.g., clarithromycin, azithromycin or vancomycin;

rifamycins; monobactams; isoniazid; licosamides; mupirocin; sulfonamides; phenicols; fosfomycin; glycopeptides; tetracyclines; streptogramins; chloramphenicol; and oxazolidinone, anti-inflammatory agents, e.g., corticosteroids or NSAID, analgesics, e.g., narcotic or non-opioic analgesics.

In accordance with the foregoing the present invention provides in a yet further aspect:

4. A method as defined above comprising co-administration, e.g., concomitantly or in sequence, of a therapeutically effective amount of a compound of the invention, e.g., of formula (I), a pharmaceutically acceptable salt thereof or a prodrug thereof, and a second therapeutic agent.
5. A therapeutic combination, e.g., a kit, comprising: a) a compound of the invention, e.g., of formula (I), a pharmaceutically acceptable salt thereof or a prodrug thereof; and b) at least one second therapeutic agent. Component a) and component b) may be used concomitantly or in sequence. The kit may comprise instructions for its administration.

The following are representative pharmaceutical formulations containing a compound of formula (I).

EXAMPLE 1

Tablet Formulation

The following ingredients are mixed intimately and pressed into single scored tablets:

| Quantity per Ingredient | Tablet (mg) |
|---|---|
| Compound of this invention | 400 |
| Cornstarch | 50 |
| Croscarmellose sodium | 25 |
| Lactose | 120 |
| Magnesium stearate | 5 |

EXAMPLE 2

Capsule Formulation

The following ingredients are mixed intimately and loaded into a hard-shell gelatin capsule:

| Quantity per Ingredient | Capsule (mg) |
|---|---|
| Compound of this invention | 200 |
| Lactose, spray-dried | 148 |
| Magnesium stearate | 2 |

EXAMPLE 3

Suspension Formulation

The following ingredients are mixed to form a suspension for oral administration:

| Ingredient | Amount |
|---|---|
| Compound of this invention | 1.0 g |
| Fumaric acid | 0.5 g |
| Sodium chloride | 2.0 g |
| Methyl paraben | 0.15 g |
| Propyl paraben | 0.05 g |
| Granulated sugar | 25.0 g |
| Sorbitol (70% solution) | 13.00 g |
| Veegum K (Vanderbilt Co.) | 1.0 g |
| Flavoring | 0.035 mL |
| Colorings | 0.5 mg |
| Distilled water | q.s. to 100 mL |

EXAMPLE 4

Injectable Formulation

The following ingredients are mixed to form an injectable formulation:

| Ingredient | Amount |
|---|---|
| Compound of this invention | 0.2–20 mg |
| Sodium acetate buffer solution, 0.4 M | 20 mL |
| HCl (1 N) or NaOH (1 N) | q.s. to suitable pH |
| Water (distilled, sterile) | q.s. to 20 mL |

EXAMPLE 5

Suppository Formulation

A suppository of total weight 2.5 g is prepared by mixing the compound of the invention with Witepsol® H-5 (triglycerides of saturated vegetable fatty acid; Riches-Nelson, Inc., NY), and has the following composition:

| | |
|---|---|
| Compound of the invention | 500 mg |
| Witepsol ® H-15 | 2000 mg |

The present invention is not limited to the clinical use of the compounds of the invention, i.e, in the treatment of infection in a subject. The compounds of the invention are useful to inhibit bacteria wherever it is desired to inhibit bacteria by contacting the bacteria with one or more compounds of the invention. Because of their ability to inhibit bacteria, the compounds of the invention are particularly useful to prevent contamination of cell cultures. As used in this context, the term "inhibit" means the suppression, control, stasis, or kill of bacteria. Eukaryotic cells, in particular animal cells, are often cultured for various reasons such as for their ability to produce substances such as proteins. Examples of such cells include Chinese hamster ovary cells (CHO cells), African green monkey kidney cells, hybridomoas constructed by fusing a parent cell (myeloma, etc.) with a useful substance-producing normal cell (lymphocyte, etc.), and the like. Typically, the compounds of the invention are incorporated into cell culture media at a bacteria inhibiting amount, e.g., a concentration of about 0.0001 mg/mL to about 10 mg/mL, preferably about 0.0001

What is claimed is:

1. The compound of formula (I)

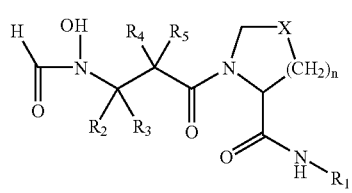

(I)

wherein X is —CH₂—, —S—, —CH(OH)—, —CH(OR)—, —CH(SH)—, —CH(SR)—, —CF₂—, —C=N(OR)— or —CH(F)—;

R is alkyl;

R$_1$ is heteroaryl or aryl;

Each of R$_2$, R$_3$, R$_4$ and R$_5$ is independently hydrogen or alkyl, or (R$_2$ or R$_3$) and (R$_4$ or R$_5$) collectively form a C$_{4-7}$ cycloalkyl; and n is 0 to 3, provided that when n is 0, X is —CH₂—;

a pharmaceutically acceptable salt thereof or a prodrug thereof.

2. The compound of formula (I) according to claim 1, wherein R$_1$ is heteroaryl, X is —CH₂—, —CH(OH)—, —CH(OR)—, —CF₂— or —CH(F)—, R$_2$, R$_3$ and R$_4$ are hydrogen, R$_5$ is alkyl and n is 1; a pharmaceutically acceptable salt thereof or a prodrug thereof.

3. The compound of formula (I) according to claim 1, wherein the heteroaryl is of formula (II)

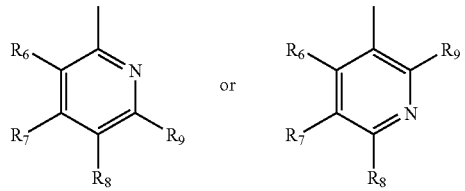

(II)

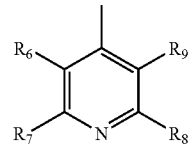

-continued

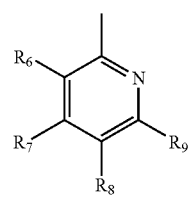

wherein R$_6$, R$_7$, R$_8$ and R$_9$ are independently hydrogen, alkyl, substituted alkyl, hydroxyl, alkoxy, acyl, acyloxy, carboxyalkyl, thiocyanate, halogen, cyano, nitro, thioalkoxy, phenyl, heteroalkylaryl, alkylsulfonyl, or formyl; a pharmaceutically acceptable salt thereof or a prodrug thereof.

4. The compound of formula (I) according to claim 3, wherein the heteroaryl of formula (II) is (II)

wherein R$_6$, R$_7$, R$_8$ and R$_9$ are as defined in claim 4; a pharmaceutically acceptable salt thereof or a prodrug thereof.

5. The compound of formula (I) according to claim 1, wherein R$_6$ is nitro, alkyl, substituted alkyl, phenyl, hydroxyl, formyl, heteroalkylaryl, alkoxy, acyl, or acyloxy; and R$_7$, R$_8$, and R$_9$ are hydrogen; a pharmaceutically acceptable salt thereof or a prodrug thereof.

6. The compound of formula (I) according to claim 5, wherein R$_6$ is alkyl, substituted alkyl, hydroxyl or alkoxy; a pharmaceutically acceptable salt thereof or a prodrug thereof.

7. The compound of formula (I) according to claim 1, wherein R$_6$, R$_8$ and R$_9$ are hydrogen, and R$_7$ is alkyl, substituted alkyl, phenyl, halogen, alkoxy or cyano; a pharmaceutically acceptable salt thereof or a prodrug thereof.

8. The compound of formula (I) according to claim 7, wherein R$_7$ is alkyl, substituted alkyl or alkoxy; a pharmaceutically acceptable salt thereof or a prodrug thereof.

9. The compound of formula (I) according to claim 1, wherein R$_6$, R$_7$, R$_9$ are hydrogen and R$_8$ is alkyl, substituted alkyl, halogen, nitro, cyano, thioalkoxy, acyloxy, phenyl, alkylsulfonyl or carboxyalkyl; a pharmaceutically acceptable salt thereof or a prodrug thereof.

10. The compound of formula (I) according to claim 9, wherein R$_8$ is alkyl, substituted alkyl, halogen or carboxyalkyl; a pharmaceutically acceptable salt thereof or a prodrug thereof.

11. The compound of formula (I) according to claim 1, wherein R$_6$, R$_7$, R$_8$ are hydrogen and R$_9$ is alkyl, halogen or hydroxyl; a pharmaceutically acceptable salt thereof or a prodrug thereof.

12. The compound of formula (I) according to claim 1, wherein R$_7$ and R$_9$ are hydrogen, and R$_6$ and R$_8$ are independently halogen, alkyl, substituted alkyl, phenyl or cyano; a pharmaceutically acceptable salt thereof or a prodrug thereof.

13. The compound of formula (I) according to claim 1, wherein R$_7$ and R$_9$ are independently alkyl or substituted alkyl and $R_6$ and $R_8$ are hydrogen; a pharmaceutically acceptable salt thereof or a prodrug thereof.

14. The compound of formula (I) according to claim 1, wherein $R_6$ and $R_9$ are hydrogen, $R_7$ is alkyl or substituted alkyl and $R_8$ is nitro; a pharmaceutically acceptable salt thereof or a prodrug thereof.

15. The compound of formula (I) according to claim 1, wherein $R_8$ and $R_9$ are hydrogen, $R_6$ is cyano, and $R_7$ is alkoxy; a pharmaceutically acceptable salt thereof or a prodrug thereof.

16. The compound of formula (I) according to claim 1, wherein $R_7$ and $R_8$ are hydrogen and $R_6$ is alkyl, substituted alkyl, alkoxy or thiocyanate and $R_9$ is alkyl or substituted alkyl; a pharmaceutically acceptable salt thereof or a prodrug thereof.

17. The compound of formula (I) according to claim 1, wherein $R_6$ and $R_7$ are hydrogen, $R_8$ is nitro or halogen and $R_9$ is alkyl or substituted alkyl; a pharmaceutically acceptable salt thereof or a prodrug thereof.

18. The compound of formula (I) according to claim 1, wherein $R_6$, $R_7$, $R_8$ and $R_9$ are hydrogen; a pharmaceutically acceptable salt thereof or a prodrug thereof.

19. The compound of formula (I) according to claim 1, wherein $R_6$ and $R_7$ combine to form phenyl and $R_8$ and $R_9$ are hydrogen; a pharmaceutically acceptable salt thereof or a prodrug thereof.

20. The compound of formula (I) according to claim 1, wherein $R_6$ and $R_7$ are hydrogen and $R_8$ and $R_9$ combine to form phenyl; a pharmaceutically acceptable salt thereof or a prodrug thereof.

21. The compound of formula (I) according to claim 20, wherein the phenyl is substituted with hydroxyl; a pharmaceutically acceptable salt thereof or a prodrug thereof.

22. The compound of formula (I) according to claim 1, wherein n is 0; a pharmaceutically acceptable salt thereof or a prodrug thereof.

23. The compound of formula (I) according to claim 22, wherein $R_6$, $R_7$, $R_8$ and $R_9$ are independently hydrogen, alkyl or halogen; a pharmaceutically acceptable salt thereof or a prodrug thereof.

24. The compound of formula (I) according to claim 23, wherein $R_6$, $R_7$, $R_8$ and $R_9$ are hydrogen; a pharmaceutically acceptable salt thereof or a prodrug thereof.

25. The compound of formula (I) according to claim 23, wherein $R_6$, $R_8$ and $R_9$ are hydrogen and $R_7$ is alkyl; a pharmaceutically acceptable salt thereof or a prodrug thereof.

26. The compound of formula (I) according to claim 23, wherein $R_6$, $R_7$ and $R_9$ are hydrogen and $R_8$ is alkyl or halogen; a pharmaceutically acceptable salt thereof or a prodrug thereof.

27. The compound according to claim 3, wherein the heteroaryl is of formula (II)

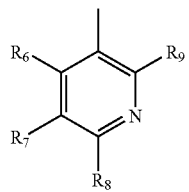

(II)

wherein $R_6$, $R_7$, $R_8$ and $R_9$ are as defined in claim 4; a pharmaceutically acceptable salt thereof or a prodrug thereof.

28. The compound of formula (II) according to claim 27, wherein $R_7$ and $R_8$ combine to form phenyl and $R_6$ and $R_9$ are hydrogen; a pharmaceutically acceptable salt thereof or a prodrug thereof.

29. The compound of formula (I) according to claim 1, wherein the heteroaryl is of formula (III)

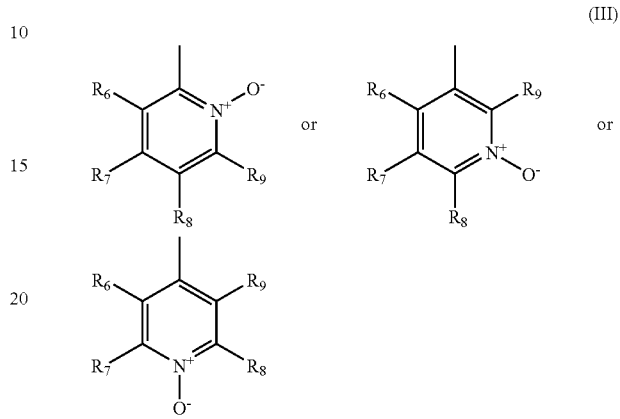

(III)

wherein $R_6$, $R_7$, $R_8$ % and $R_9$ are independently hydrogen, alkyl, substituted alkyl, phenyl, halogen, hydroxyl or alkoxy; a pharmaceutically acceptable salt thereof or a prodrug thereof.

30. The compound of formula (I) according to claim 29, wherein the heteroaryl is of the formula (III)

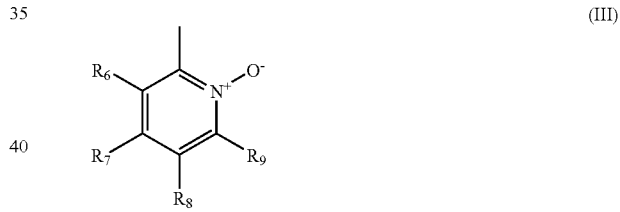

(III)

wherein $R_6$, $R_7$, $R_8$ and $R_9$ are as defined in claim 29; a pharmaceutically acceptable salt thereof or a prodrug thereof.

31. The compound of formula (III) according to claim 29, wherein $R_6$ and $R_8$ are hydrogen, $R_9$ is hydrogen or alkyl and $R_7$ is alkyl, substituted alkyl or phenyl; a pharmaceutically acceptable salt thereof or a prodrug thereof.

32. The compound of formula (III) according to claim 29, wherein $R_6$, $R_7$ and $R_9$ are hydrogen and $R_8$ is halogen, alkyl or substituted alkyl; a pharmaceutically acceptable salt thereof or a prodrug thereof.

33. The compound of formula (III) according to claim 29, wherein $R_7$, $R_8$ and $R_9$ are hydrogen and $R_6$ is hydroxyl; a pharmaceutically acceptable salt thereof or a prodrug thereof.

34. The compound of formula (I) according to claim 1, wherein $R_1$ is substituted or unsubstituted phenyl; a pharmaceutically acceptable salt thereof or a prodrug thereof.

35. The compound of formula (I) according to claim 34, wherein the phenyl is substituted with an alkoxy or aryloxy group; a pharmaceutically acceptable salt thereof or a prodrug thereof.

36. The compound of formula (I) according to claim 1, wherein the heteroaryl is of formula (IV)

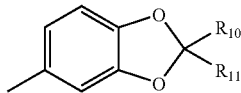

wherein $R_{10}$ and $R_{11}$ are independently hydrogen or halogen; a pharmaceutically acceptable salt thereof or a prodrug thereof.

37. The compound of formula (IV) according to claim 36, wherein $R_{10}$ and $R_{11}$ are both hydrogen or both halogen; a pharmaceutically acceptable salt thereof or a prodrug thereof.

38. A compound according to claim 1, wherein the compound is selected from the group consisting of 1-{2-R-[(formyl-hydroxy-amino)-methyl]-hexanoyl}-pyrrolidine-2-S-carboxylic acid-(5-methyl-pyridin-2-yl)-amide, 1-{2-R-[(formyl-hydroxy-amino)-methyl]-hexanoyl}-pyrrolidine-2-S-carboxylic acid-(5-trifluoromethyl-pyridin-2-yl)-amide, 1-{2-R-[(formyl-hydroxy-amino)-methyl]-hexanoyl }-pyrrolidine-2-S-carboxylic acid-(6-fluoro-pyridin-2-yl)-amide, 1-{2-R-[(formyl-hydroxy-amino)-methyl]-hexanoyl}-pyrrolidine-2-S-carboxylic acid-(4-ethyl-pyridin-2-yl)-amide, 1-{2-R-[(formyl-hydroxy-amino)-methyl]-hexanoyl}-pyrrolidine-2-S-carboxylic acid (3-hydroxy-pyridin-2-yl)-amide, 1-{2-R-[(formyl-hydroxy-amino)-methyl]-hexanoyl}-pyrrolidine-2-S-carboxylic acid-(5-trifluoromethyl-1-oxy-pyridin-2-yl)-amide, 1-{2-R-[(formyl-hydroxy-amino)-methyl]-hexanoyl}-pyrrolidine-2-S-carboxylic acid-(4-ethyl-1-oxy-pyridin-2-yl)-amide, 1-{2-R-[(formyl-hydroxy-amino)-methyl]-hexanoyl}-pyrrolidine-2-S-carboxylic acid-(3-methoxy-6-methyl-pyridin-2-yl)-amide, 1-{2-R-[(formyl-hydroxy-amino)-methyl]-hexanoyl}-pyrrolidine-2-S-carboxylic acid (4-methoxy-pyridin-2-yl)-amide and 1-{2-R-[(formyl-hydroxy-amino)-methyl]-hexanoyl}-pyrrolidine-2-S-carboxylic acid (5-fluoro-1-oxy-pyridin-2-yl)-amide; a pharmaceutically acceptable salt of any said compound or a prodrug of any said compound.

39. A pharmaceutical composition comprising a compound of formula (I), a pharmaceutically acceptable salt thereof or a prodrug thereof according to claim 1, and a pharmaceutically acceptable carrier.

40. The pharmaceutical composition according to claim 39, wherein the composition further includes another therapeutic agents selected from the group consisting of other antibacterial agents, anti-inflammatory agents and analgesics.

* * * * *